(12) United States Patent
Faust et al.

(10) Patent No.: US 9,574,043 B2
(45) Date of Patent: Feb. 21, 2017

(54) POLYISOBUTYLENE-BASED POLYURETHANES

(75) Inventors: Rudolf Faust, Lexington, MA (US); Umaprasana Ojha, Lowell, MA (US)

(73) Assignee: University of Massachusetts Lowell, Lowell, MA (US)

(*) Notice: Subject to any disclaimer, the term of this patent is extended or adjusted under 35 U.S.C. 154(b) by 0 days.

(21) Appl. No.: 12/685,858

(22) Filed: Jan. 12, 2010

(65) Prior Publication Data

US 2010/0179298 A1  Jul. 15, 2010

Related U.S. Application Data

(60) Provisional application No. 61/204,856, filed on Jan. 12, 2009, provisional application No. 61/211,310, (Continued)

(51) Int. Cl.
| | |
|---|---|
| *C08G 18/67* | (2006.01) |
| *C08G 18/32* | (2006.01) |
| *A61L 27/18* | (2006.01) |
| *A61L 27/26* | (2006.01) |
| *A61L 27/34* | (2006.01) |
| *A61L 29/04* | (2006.01) |

(Continued)

(52) U.S. Cl.
CPC ............. *C08G 18/32* (2013.01); *A61L 27/18* (2013.01); *A61L 27/26* (2013.01); *A61L 27/34* (2013.01); *A61L 29/049* (2013.01); *A61L 29/06* (2013.01); *A61L 29/085* (2013.01); *A61L 31/06* (2013.01); *A61L 31/10* (2013.01); *C08G 18/4063* (2013.01); *C08G 18/4854* (2013.01); *C08G 18/6204* (2013.01); *C08G 18/6511* (2013.01); *C08G 18/7671* (2013.01)

(58) Field of Classification Search
None
See application file for complete search history.

(56) References Cited

U.S. PATENT DOCUMENTS 3,328,372 A    6/1967  Thomas et al.
3,427,366 A *  2/1969  Verdol et al. ............... 525/126
(Continued)

FOREIGN PATENT DOCUMENTS

BR    9003841       2/1992
BR    9003841 A     2/1992
(Continued)

OTHER PUBLICATIONS

International Search Report and Written Opinion issued in PCT/US2010/047633, Jun. 17, 2011, 12 pages.
(Continued)

*Primary Examiner* — Jeffrey Washville
(74) *Attorney, Agent, or Firm* — Faegre Baker Daniels LLP

(57) ABSTRACT

An elastomeric polymer, comprising (1) a hard segment in the amount of 10% to 60% by weight of the elastomeric polymer, wherein the hard segment includes a urethane, urea or urethaneurea; and (2) a soft segment in the amount of 40% to 90% by weight of the elastomeric polymer. The soft segment comprises (a) at least 2% by weight of the soft segment of at least one polyether macrodiol, and/or at least one polycarbonate macrodiol; and (b) at least 2% by weight of the soft segment of at least one polyisobutylene macrodiol and/or diamine.

40 Claims, 16 Drawing Sheets

BDO = 1,4-butanediol,
MDI = 4,4'-methylenebis(phenylisocyanate)

Related U.S. Application Data filed on Mar. 26, 2009, provisional application No. 61/279,629, filed on Oct. 23, 2009.

(51) Int. Cl.

| | |
|---|---|
| A61L 29/06 | (2006.01) |
| A61L 29/08 | (2006.01) |
| A61L 31/06 | (2006.01) |
| A61L 31/10 | (2006.01) |
| C08G 18/40 | (2006.01) |
| C08G 18/48 | (2006.01) |
| C08G 18/62 | (2006.01) |
| C08G 18/65 | (2006.01) |
| C08G 18/76 | (2006.01) |

(56) References Cited

U.S. PATENT DOCUMENTS

| | | |
|---|---|---|
| 3,505,252 A | 4/1970 | Brotherton et al. |
| 3,642,964 A | 2/1972 | Rausch, Jr. et al. |
| 3,815,611 A | 6/1974 | Denniston, III |
| 4,043,331 A | 8/1977 | Martin et al. |
| 4,103,079 A | 7/1978 | Thaler |
| 4,118,427 A | 10/1978 | Rhein et al. |
| 4,276,394 A | 6/1981 | Kennedy et al. |
| 4,316,973 A | 2/1982 | Kennedy |
| 4,342,849 A | 8/1982 | Kennedy |
| 4,352,359 A | 10/1982 | Larimore et al. |
| 4,423,185 A | 12/1983 | Matsumoto et al. |
| 4,477,604 A | 10/1984 | Oechsle, III |
| 4,486,572 A | 12/1984 | Kennedy |
| 4,539,996 A | 9/1985 | Engel |
| 4,570,270 A | 2/1986 | Oechsle, III |
| 4,675,361 A | 6/1987 | Ward, Jr. et al. |
| 4,686,137 A | 8/1987 | Ward, Jr. et al. |
| 4,752,626 A | 6/1988 | Hoye et al. |
| 4,767,885 A | 8/1988 | Kennedy |
| 4,771,082 A | 9/1988 | Solodovnik et al. |
| 4,861,830 A | 8/1989 | Ward, Jr. |
| 4,880,883 A | 11/1989 | Grasel et al. |
| 4,888,389 A | 12/1989 | Kennedy et al. |
| 4,906,673 A | 3/1990 | Mori et al. |
| 4,928,689 A | 5/1990 | Hauser |
| 4,939,184 A | 7/1990 | Kennedy |
| 5,017,664 A | 5/1991 | Grasel et al. |
| 5,090,422 A | 2/1992 | Dahl et al. |
| 5,103,837 A | 4/1992 | Weidlich et al. |
| 5,120,813 A * | 6/1992 | Ward, Jr. .................. 528/28 |
| 5,129,404 A | 7/1992 | Spehr et al. |
| 5,149,739 A | 9/1992 | Lee |
| 5,152,299 A | 10/1992 | Soukup |
| 5,171,760 A | 12/1992 | Kaszas et al. |
| 5,194,505 A | 3/1993 | Brugel |
| 5,212,248 A | 5/1993 | Knoll et al. |
| 5,269,810 A | 12/1993 | Hull et al. |
| 5,282,844 A | 2/1994 | Stokes et al. |
| 5,322,520 A | 6/1994 | Milder |
| 5,324,324 A | 6/1994 | Vachon et al. |
| 5,330,520 A | 7/1994 | Maddison et al. |
| 5,332,791 A | 7/1994 | Knoll et al. |
| 5,340,881 A | 8/1994 | Kennedy et al. |
| 5,385,579 A | 1/1995 | Helland |
| 5,428,123 A | 6/1995 | Ward et al. |
| 5,433,730 A | 7/1995 | Alt |
| 5,442,010 A | 8/1995 | Hauenstein et al. |
| 5,442,015 A | 8/1995 | Kennedy et al. |
| 5,476,496 A | 12/1995 | Strandberg et al. |
| 5,554,178 A | 9/1996 | Dahl et al. |
| 5,589,563 A * | 12/1996 | Ward et al. .................. 528/44 |
| 5,609,622 A | 3/1997 | Soukup et al. |
| 5,637,647 A | 6/1997 | Faust |
| 5,663,234 A | 9/1997 | Kennedy et al. |
| 5,677,386 A | 10/1997 | Faust |
| 5,681,514 A | 10/1997 | Woody |
| 5,741,331 A | 4/1998 | Pinchuk |
| 5,755,762 A | 5/1998 | Bush |
| 5,766,527 A | 6/1998 | Schildgen et al. |
| 5,837,313 A | 11/1998 | Ding et al. |
| 5,849,415 A | 12/1998 | Shalaby et al. |
| 5,852,118 A | 12/1998 | Horrion et al. |
| 5,853,652 A | 12/1998 | Schildgen et al. |
| 5,861,023 A | 1/1999 | Vachon |
| 5,874,484 A | 2/1999 | Dirckx et al. |
| 5,902,329 A | 5/1999 | Hoffmann et al. |
| 5,912,302 A | 6/1999 | Gadkari et al. |
| 5,931,862 A | 8/1999 | Carson |
| 5,987,746 A | 11/1999 | Williams |
| 5,991,667 A | 11/1999 | Feith |
| 6,005,051 A | 12/1999 | Kennedy et al. |
| 6,010,715 A | 1/2000 | Wick et al. |
| 6,072,003 A | 6/2000 | Horrion et al. |
| 6,093,197 A | 7/2000 | Bakula et al. |
| 6,117,554 A | 9/2000 | Shalaby et al. |
| 6,200,589 B1 | 3/2001 | Kennedy et al. |
| 6,228,945 B1 | 5/2001 | Kennedy et al. |
| 6,236,893 B1 | 5/2001 | Thong |
| 6,242,058 B1 | 6/2001 | Bahadur et al. |
| 6,253,110 B1 | 6/2001 | Brabec et al. |
| 6,256,541 B1 | 7/2001 | Heil et al. |
| 6,284,682 B1 | 9/2001 | Troczynski et al. |
| 6,361,780 B1 | 3/2002 | Ley et al. |
| 6,363,286 B1 | 3/2002 | Zhu et al. |
| 6,365,674 B1 * | 4/2002 | Kaufhold et al. ............ 525/127 |
| 6,426,114 B1 | 7/2002 | Troczynski et al. |
| 6,444,334 B1 | 9/2002 | Doi et al. |
| 6,545,097 B2 | 4/2003 | Pinchuk et al. |
| 6,555,619 B1 | 4/2003 | Kennedy et al. |
| 6,600,956 B2 | 7/2003 | Maschino et al. |
| 6,627,724 B2 * | 9/2003 | Meijs et al. .................. 528/26 |
| 6,709,514 B1 | 3/2004 | Hossainy |
| 6,730,324 B2 | 5/2004 | Troczynski et al. |
| 6,770,325 B2 | 8/2004 | Troczynski et al. |
| 6,849,667 B2 | 2/2005 | Haseyama et al. |
| 6,870,024 B2 | 3/2005 | Haubennestel et al. |
| 6,889,092 B2 | 5/2005 | Zhu et al. |
| 6,896,965 B1 | 5/2005 | Hossainy |
| 7,013,182 B1 | 3/2006 | Krishnan |
| 7,101,956 B2 | 9/2006 | Benz et al. |
| 7,105,622 B2 | 9/2006 | Kennedy et al. |
| 7,115,300 B1 | 10/2006 | Hossainy |
| 7,174,221 B1 | 2/2007 | Chen et al. |
| 7,196,142 B2 | 3/2007 | Kennedy et al. |
| 7,247,364 B2 | 7/2007 | Hossainy et al. |
| 7,279,175 B2 | 10/2007 | Chen et al. |
| 7,292,890 B2 | 11/2007 | Whitehurst et al. |
| 7,347,751 B2 | 3/2008 | Sweeney et al. |
| 7,715,922 B1 | 5/2010 | Tan |
| 7,756,589 B2 | 7/2010 | Krishnan |
| 7,881,808 B2 | 2/2011 | Borgaonkar et al. |
| 7,979,142 B2 | 7/2011 | Krishnan |
| 8,324,290 B2 * | 12/2012 | Desai et al. .................. 523/105 |
| 8,372,468 B2 | 2/2013 | Desai et al. |
| 8,529,934 B2 | 9/2013 | Desai et al. |
| 8,660,663 B2 | 2/2014 | Wolf et al. |
| 8,676,344 B2 | 3/2014 | Desai et al. |
| 2002/0012694 A1 | 1/2002 | Moo-Young et al. |
| 2002/0022826 A1 | 2/2002 | Reynolds et al. |
| 2002/0138123 A1 | 9/2002 | Casas-Bejar et al. |
| 2003/0031699 A1 | 2/2003 | Van Antwerp |
| 2003/0073961 A1 | 4/2003 | Happ |
| 2003/0093136 A1 | 5/2003 | Osypka et al. |
| 2003/0125499 A1 | 7/2003 | Benz et al. |
| 2003/0204022 A1 | 10/2003 | Kennedy et al. |
| 2004/0037886 A1 | 2/2004 | Hsu |
| 2004/0054210 A1 | 3/2004 | Benz et al. |
| 2004/0059402 A1 | 3/2004 | Soukup et al. |
| 2004/0063805 A1 | 4/2004 | Pacetti et al. |
| 2004/0068036 A1 | 4/2004 | Halladay et al. |
| 2004/0198901 A1 * | 10/2004 | Graham et al. ............ 524/589 |
| 2005/0031874 A1 | 2/2005 | Michal et al. |
| 2005/0037050 A1 | 2/2005 | Weber |
| 2005/0060022 A1 | 3/2005 | Felt et al. |
| 2005/0070985 A1 | 3/2005 | Knapp et al. |

(56) References Cited

U.S. PATENT DOCUMENTS

| | | | |
|---|---|---|---|
| 2005/0080470 A1 | 4/2005 | Westlund et al. | |
| 2005/0180919 A1 | 8/2005 | Tedeschi | |
| 2005/0288476 A1 | 12/2005 | Yilgor et al. | |
| 2006/0047083 A1 | 3/2006 | Yilgor et al. | |
| 2006/0223946 A1 | 10/2006 | Faust et al. | |
| 2006/0235499 A1 | 10/2006 | Heil et al. | |
| 2006/0264577 A1 | 11/2006 | Faust et al. | |
| 2007/0051531 A1 | 3/2007 | Borgaonkar et al. | |
| 2007/0093604 A1 | 4/2007 | Kennedy et al. | |
| 2007/0128246 A1 | 6/2007 | Hossainy et al. | |
| 2007/0151531 A1 | 7/2007 | Masaoka et al. | |
| 2007/0190104 A1 | 8/2007 | Kamath et al. | |
| 2007/0190108 A1* | 8/2007 | Datta | A61L 27/48 424/423 |
| 2007/0190319 A1* | 8/2007 | Kalayci | D01D 5/0084 428/364 |
| 2007/0203302 A1 | 8/2007 | Kennedy et al. | |
| 2007/0282411 A1 | 12/2007 | Franz et al. | |
| 2008/0009939 A1 | 1/2008 | Gueriguian et al. | |
| 2008/0051866 A1 | 2/2008 | Chen et al. | |
| 2008/0167423 A1 | 7/2008 | Richards et al. | |
| 2008/0167710 A1 | 7/2008 | Dave et al. | |
| 2009/0054961 A1 | 2/2009 | Borgaonkar et al. | |
| 2009/0187162 A1 | 7/2009 | Ohara et al. | |
| 2009/0326077 A1 | 12/2009 | Desai et al. | |
| 2010/0023104 A1 | 1/2010 | Smith | |
| 2010/0069578 A1 | 3/2010 | Faust et al. | |
| 2010/0075018 A1 | 3/2010 | Desai et al. | |
| 2010/0107967 A1 | 5/2010 | Tanaka et al. | |
| 2010/0241204 A1 | 9/2010 | Scheuermann | |
| 2010/0241208 A1 | 9/2010 | Pinchuk | |
| 2010/0241209 A1 | 9/2010 | Krishnan | |
| 2010/0249296 A1 | 9/2010 | Kimura et al. | |
| 2011/0045030 A1 | 2/2011 | Desai et al. | |
| 2011/0051581 A1 | 3/2011 | Janik et al. | |
| 2011/0054580 A1 | 3/2011 | Desai et al. | |
| 2011/0054581 A1 | 3/2011 | Desai et al. | |
| 2011/0087317 A1 | 4/2011 | Borgaonkar et al. | |
| 2012/0077934 A1 | 3/2012 | Faust et al. | |
| 2012/0259069 A1 | 10/2012 | Kennedy et al. | |
| 2013/0041442 A1 | 2/2013 | Arnholt et al. | |
| 2013/0122185 A1 | 5/2013 | Desai et al. | |
| 2013/0131765 A1 | 5/2013 | Polkinghorne et al. | |
| 2014/0074201 A1 | 3/2014 | Arnholt et al. | |
| 2014/0088218 A1 | 3/2014 | Desai et al. | |
| 2014/0144580 A1 | 5/2014 | Desai et al. | |
| 2014/0194963 A1 | 7/2014 | Desai et al. | |
| 2015/0274876 A1 | 10/2015 | Faust | |

FOREIGN PATENT DOCUMENTS

| | | | |
|---|---|---|---|
| CA | 2114874 | * | 2/1994 |
| CA | 2278680 | | 8/1998 |
| CA | 2278680 A1 | | 8/1998 |
| CN | 1221430 A | | 6/1999 |
| CN | 1248606 | | 3/2000 |
| CN | 1248606 A | | 4/2006 |
| CN | 104520345 A | | 4/2015 |
| CN | 2010800475975 B | | 4/2015 |
| DE | 196 10 350 A1 | | 9/1997 |
| DE | 19610350 A1 | | 9/1997 |
| EP | 0153520 A1 | | 9/1985 |
| EP | 0259492 | | 3/1988 |
| EP | 0259492 A1 | | 3/1988 |
| EP | 0 610 714 A2 | | 8/1994 |
| EP | 0610714 A2 | | 8/1994 |
| EP | 0732349 A2 | | 9/1996 |
| EP | 0837097 A1 | | 4/1998 |
| EP | 0837097 | | 8/1999 |
| EP | 1061092 | | 12/2000 |
| EP | 1061092 A1 | | 12/2000 |
| EP | 0961796 | | 5/2002 |
| EP | 0732349 | | 7/2002 |
| EP | 1 489 109 A2 | | 12/2004 |
| EP | 1489109 A2 | | 12/2004 |
| EP | 2006328 A1 | | 12/2008 |
| EP | 2922888 A2 | | 9/2015 |
| JP | 02088614 A | | 3/1990 |
| JP | 4154815 A | | 5/1992 |
| JP | 6345821 A | | 12/1994 |
| JP | 7102017 A | | 4/1995 |
| JP | 7330591 A | | 12/1995 |
| JP | 07331223 A | | 12/1995 |
| JP | 1087726 A | | 4/1998 |
| JP | 11-131325 | | 5/1999 |
| JP | 11131325 A | | 5/1999 |
| JP | 2000169814 A | | 6/2000 |
| JP | 2001011319 A | | 1/2001 |
| JP | 2001040064 A | | 2/2001 |
| JP | 2001131879 A | | 5/2001 |
| JP | 2002348317 A | | 12/2002 |
| JP | 2004204181 A | | 7/2004 |
| JP | 2006515795 A | | 6/2006 |
| JP | 2008-238761 | | 10/2008 |
| JP | 2008238761 A | | 10/2008 |
| JP | 2009535182 A | | 10/2009 |
| JP | 2009540873 A | | 11/2009 |
| JP | 2012519053 A | | 8/2012 |
| WO | WO 87/04625 | | 8/1987 |
| WO | WO 93/22360 | | 11/1993 |
| WO | WO 95/26993 | | 10/1995 |
| WO | WO 97/00293 | | 1/1997 |
| WO | WO 97/47664 | | 12/1997 |
| WO | WO 98/33832 | | 8/1998 |
| WO | WO0213785 A2 | | 2/2002 |
| WO | WO 03/042273 | | 5/2003 |
| WO | WO 2004/014453 | | 2/2004 |
| WO | WO 2004/044012 | | 5/2004 |
| WO | WO 2004/113400 A2 | | 12/2004 |
| WO | WO2005035655 A1 | | 4/2005 |
| WO | WO 2006/110647 | | 10/2006 |
| WO | WO2006110647 A1 | | 10/2006 |
| WO | WO2007030722 A1 | | 3/2007 |
| WO | WO 2007/117566 | | 10/2007 |
| WO | WO2007119687 A1 | | 10/2007 |
| WO | 2007130900 A2 | | 11/2007 |
| WO | WO2007126806 A1 | | 11/2007 |
| WO | WO 2008/060333 | | 5/2008 |
| WO | WO 2008/066914 | | 6/2008 |
| WO | WO 2008/112190 | | 9/2008 |
| WO | WO 2008/127730 | | 10/2008 |
| WO | WO 2008/156806 | | 12/2008 |
| WO | WO2009051945 A1 | | 4/2009 |
| WO | WO 2009/058397 | | 5/2009 |
| WO | WO 2009/158600 A1 | | 12/2009 |
| WO | WO 2009/158609 | | 12/2009 |
| WO | WO 2010/039986 A1 | | 4/2010 |
| WO | WO 2010/081132 | | 7/2010 |
| WO | WO 2010/081132 A1 | | 7/2010 |
| WO | 2010107530 A2 | | 9/2010 |
| WO | WO 2010/111280 A1 | | 9/2010 |
| WO | 2010135418 A2 | | 11/2010 |
| WO | WO2011022583 A1 | | 2/2011 |
| WO | WO 2011/060161 A1 | | 5/2011 |
| WO | 2014081916 | | 5/2014 |

OTHER PUBLICATIONS

International Search Report and Written Opinion issued in PCT/US2010/047703, mailed Jun. 17, 2011, 12 pages.

Ako, M. et al., "Polyisobutylene-Based Urethane foams. II. Synthesis and Properties of Novel Polyisobutylene-Based Flexible Polyurethane Foams," J. Appl. Polym. Sci., 37(5): 1351-1361 (1989).

De, P, et al., "Carbocationic Polymerization of Isobutylene Using Methylaluminum Bromide Coinitiators: Synthesis of Bromoallyl Functional Polyisobutylene," Macromolecules, 39:7527-7533 (2006) (month of publication not available).

Erdodi, G., et al., "Polyisobutylene-Based Polyurethanes. III. Polyurethanes Containing PIB/PTMO Soft Co-Segments," J. Polym. Sci., Part A: Polym. Chem, 47:5278-5290 (2009).

(56) References Cited

OTHER PUBLICATIONS

Gadkari, A., et al., "Preparation and Biocompatibility of Novel Polar-Nonpolar Networks. Synthesis, Characterization and Historical Bacterial Analysis of Mixed Polytetrahydrofuran-Polyisobutylene Networks," Polymer Bulletin, Springer, Heidelberg, Germany, 22(1): 25-32 (1989).
Higashihara, T., et al., "Synthesis of Poly(isobutylene-block-methyl methacrylate) by a Novel Coupling Approach," Macromolecules, 39:5275-5279 (2006) (month of publication not available).
International Search Report from PCT/US2006/013308, dated Aug. 25, 2006.
International Preliminary Report on Patentability and Written Opinion from PCT/US2006/013308, dated Oct. 9, 2007.
International Search Report from PCT/US2007/008528, dated Oct. 2, 2007.
International Preliminary Report on Patentability and Written Opinion from PCT/US2007/012948, dated May 28, 2009.
International Search Report, PCT/US2007/012948, dated Nov. 28, 2007.
International Search Report and Written Opinion, PCT/US2010/028334, dated May 6, 2010.
International Search Report and Written Opinion from PCT/US2010/020733, dated May 6, 2010.
Ioffe, et al. Bromine, Organic Compounds, Kirk-Othmer Encyclopedia of Chemical Technology, pp. 340-365, 2002.
Li, J., et al., "Polyisobutylene supports—a non-polar hydrocarbon analog of PEG supports," Tetrahedron, 61:12081-12092 (2005) (month of publication not available).
Mitzner, E., "Modification of Segmented Poly(Ether Urethanes) by Incorporation of Poly(Isobutylene)Glycol," J. of Macromol. Sci., Part A—Pure Appl. Chem, A34(1):165-178 (1997).
Yoon, S.C., et al., "Surface and Bulk Structure of Segmented Poly(Ether Urethanes) with Perfluoro Chain Extenders. 5. Incorporation of Poly(Dimethylsiloxane) and Polyisobutylene Macroglycols," Macromolecules, Am. Chem. Soc., 27(6): 1548-1554 (1994).
Office Action, Date of Mailing: Aug. 24, 2010, U.S. Appl. No. 11/400,059.
Ako, Masayuke et al., "Polyisobutylene-based urethane foams I. Comparative reactivities of hydroxyl-terminated polyisobutylene-diols and -triols and other hydroxyl-capped polyols with isocyanate", Polymer Bulletin 19(2), 137-143 (1988).
Bela et al., Living Carbocation Polymerization. XX. Synthesis of Allyl-Telechelic Polyisobutylenes by One-Pot Polymerization-Functionalization polymer. Mater. Sci. Eng. 1988; 58:869-872.
Chang, Victor S.C. et al. "Gas Permeability, Water Absorption, Hydrolytic Stability and Air-Oven Aging of Polyisobutylene-Based Polyurethane Networks", Polymer Bulletin 8(2-3-4), 69-74 (1982).
Cozzens, David et al., "Long term in vitro biostability of segmented polyisobutylene-based thermoplastic polyurethanes", Journal of Biomedicals Materials Research Journal, 2010, pp. 1-9.
De, Priyadarsi et al., "Relative Reactivity of C4 Olefins toward the Polyisobutylene Cation" Macromolecules 2006, 39, 6861-6870.
Giusti, Paolo et al., "Synthesis and Characterization of New potentially Hemocompatible Thermoplastic Elastomers" , p. 371, Abstract.
Gunatillake, P.A. et al., "Poly(dimethylsiloxane)/Poly(hexamethylene oxide) Mixed Macrodiol Based Polyurethane Elastomers. I. Synthesis and Properties", Journal of Appl. Polym. Sci. 2000, 76, 2026-2040, © 2000.
Ivan, B. et al., "Synthesis of New Polyisobutylene-Based Polyurethanes", Am. Chem. Soc., Div. Org. Coat. Plast. Prepr., 43, 908-913 (1980).
Jenny, C. et al., "A New Insulation Material for Cardiac Leads with Potential for Improved performance", HRS 2005, HeartRhythm, 2, S318-S319 (2005).
Jewrajka, Suresh K. et al., "Polyisobutylene-Based Polyurethanes. II. Polyureas Containing Mixed PIB/PTMO Soft Segments", Journal of Polymer Science: Part A: Polymer Chemistry, vol. 47, 2787-2797 (2009).
Jewrajka, Suresh K. et al., "Polyisobutylene-Based Segmented Polyureas. I. Synthesis of Hydrolytically and Oxidatively Stable Polyureas", Journal of Polymer Science: Part A: Polymer Chemistry, vol. 47, 38-48 (2009).
Kennedy, J.P. et al., "Designed Polymers by Carbocationic Macromolecular Engineering: Theory and practice", Hanser Publishers 1991, pp. 191-193 and 226-233.
Kennedy, J.P. et al., "Polyisobutylene-Based Diols and Polyurethanes" , Urethane Chemistry and Applications, Ed., K.H. Edwards, ACS Symp. Book Series, 172, Washington, D.C. 1981, pp. 383-391.
Kennedy, J.P. et al., "Polyisobutylene-Based Diols and Polyurethanes" Advances in Urethane Science and Technology, vol. 8, 1981, pp. 245-251.
Kennedy, J.P. et al., "Polyisobutylene-based Model urethane Networks, I. Initial characterization and Physical properties", Polymeric Materials Science and Engineering, vol. 49, Copyright 1983 by ACS, pp. 69-77.
Kennedy, Joseph P. Synthesis, Characterization and Properties of Novel Polyisobutylene-Based urethane Model Networks, Journal of Applied Polymer Science, vol. 33(7), May 20, 1987, pp. 2449-2465.
Kennedy, Joseph P. "Synthesis, Characterization and Properties of Polyisobutylene-Based Polyurethanes", 6th International Technical/Marketing Conference: Polyurethane—New Paths to Progress-Marketing—Technology, Journal of Cellular Plastics, 1983, 19:288-307.
Kennedy, Joseph P. "Synthesis, Characterization and Properties of Polyisobutylene-Based Polyurethanes", Journal of Elastomers and Plastics, vol. 17 (Jan. 1985), pp. 82-88.
Kennedy, Joseph P. "Synthesis, Characterization and Properties of Polyisobutylene-Based Polyurethanes", The Society of the Plastics Industry, Inc., polyurethane Division, Proceedings of the SPI—6th International Technical/Marketing Conference, Nov. 2-4, 1983, San Diego, CA, pp. 514-516.
Kennedy, Joseph P., "Polyurethanes Based on Polyisobutylenes", Chemtech, Nov. 1986, 16(11), pp. 694-697.
Lelah, M.D. et al., "Polyurethanes in Medicine", CRC Press, Boca Raton, FL 1986, Chapter 3.
Macias, A. et al., "Preparacion y reticulacion de poliisobutilenos de bajo peso molecular con grupos terminales reactivos", Revista de Plasticos Modernos, Num 332 (Abril '83), pp. 412-418.
Miller, J. A., "New Directions in Polyurethane Research", Organic Coatings and Applied Polymer Science Proceedings, vol. 47, Copyright 1982 by ACS, pp. 124-129.
Mitzner, E. et al., "Modification of poly(ether urethane) elastomers by incorporation of poly(isobutylene) glycol. Relation between polymer properties and thrombogenicity", J. Biomater. Sci. Polymer edn. vol. 7, No. 12, pp. 1105-1118 (1996).
Miyabayashi, Toshio et al., "Characterization of Polyisobutylene-Based Model Urethane Networks", Journal of Applied Polymer Science, vol. 31, pp. 2523-2532 (1986).
Muller, J.P. et al., "Surface modification of polyurethanes by multicomponent polyaddition reaction", Journal of Materials Science Letters 17(2), 1998, pp. 115-118.
Ojha et al., "Synthesis and Characterization of Thermoplastic Polyurethaneureas based on Polyisobutylene and Poly(tetramethylene oxide) Segments", J. Macromolecular Science, Part A, vol. 47(3), pp. 186-191, Mar. 2010.
Ojha, Umaprasana et al., "Syntheses and characterization of novel biostable polyisobutylene based thermoplastic polyurethanes", Polymer 50(2009), 3448-3457.
Ojha, Umaprasana et al., "Synthesis and Characterization of Endfunctionalized Polyisobutylenes for Sharpless-type Click Reactions", Polymer Preprints 2007, 48(2), 786.
Puskas, J.E. et al., "polyisobutylene-based biomaterials", Journal of Polymer Science Part A: Polymer Chemistry, vol. 42, Issue 13 (2004) pp. 3091-3109.
Rajkhowa, Ritimoni et al., "Efficient syntheses of hydroxyallyl end functional polyisobutylenes, a precursors to thermoplastic polyurethanes", Polymer Reprints (American Chemical Society, Division of Polymer Chemistry) 2007, 48(2), 233-234.

(56) References Cited

OTHER PUBLICATIONS

Ranade, S. et al., "Physical characterization of controlled release of paclitaxel from the TAXUS™ Express2™ drug-eluting stent", Journal of Biomedical Materials Research Part A, 71A (2004) 625-634.
Ranade, S.V. et al., Styrenic Block copolymers for Biomaterial and Drug Delivery Applications, Acta Biomater. Jan. 2005; 1(1): 137-44.
Simmons, Anne. et al., "The effect of sterilisation on a poly(dimethylsiloxane)/poly(hexamethylene oxide) mixed macrodiol-based Polyurethane elastomer", Biomaterials 2006, 27, 4484-4497.
Speckhard, T.A. et al., "New generation polyurethanes", Polymer News 1984, 9(12), 354-358.
Speckhard, T.A. et al., "Properties of Polyisobutylene Polyurethane Block Copolymers: 2. Macroglycols produced by the 'inifer' technique", Polymer, vol. 26, No. 1, Jan. 1985, pp. 55-78.
Speckhard, T.A. et al., "Properties of Polyisobutylene Polyurethane Block Copolymers: 3. hard segments based on 4,4'-dicyclohexylmethane diisocyanate (H12MDI) and butane diol", Polymer, vol. 26, No. 1, Jan. 1985, pp. 70-78.
Speckhard, T.A. et al., "Properties of Polyisobutylene-Polyurethane Block Copolymers", Journal of Elastomers and Plastics, vol. 15 (Jul. 1983), pp. 183-192.
Speckhard, T.A. et al., "Properties of Polyisobutylene-Polyurethane Block Copolymers: I. Macroglycols from Ozonolysis of Isobutylene-Isoprene Copolymer", Polymer Engineering and Science, Apr. 1983, vol. 23. No. 6, pp. 337-349.
Speckhard, T.A. et al., "Ultimate Tensite Properties of Segmented Polyurethane Elastomers", Rubber Chem. Technol., 59, 405-431 (1986).
Tonelli, C. et al., "New Fluoro-Modified Thermoplastic Polyurethanes" Journal of Applied Polymer Science, vol. 87, Issue 14 (2003) 2279-2294.
Virmani, R. et al. Circulation Feb. 17, 2004 109)6) 701-5.
Wang, F. Polydimethylsiloxane Modification of Segmented Thermoplastic Polyurethanes and Polyureas, PhD. Dissertation, Virginia Polytechnic Institute and State university, Apr. 13, 1998.
Weisberg, David M. et al., "Synthesis and Characterization of Amphiphilic Poly(urethaneurea)-comb-polyisobutylene Copolymers", Macromolecules 2000, 33(12), pp. 4380-4389.
Weissmuller, M. et al., "Preparation and end-linking of hydroxyl-terminated polystyrene star macromolecules", Macromolecular Chemistry and Physics 200(3), 1999, 541-551.
Wiggins, Michael J. et al., "Effect of soft-segment chemistry on polyurethane biostability during in vitro fatigue loading", Journal of biomedical materials research, 68(4), 2004, 668-683.
Wu, Yuguang et al., "The role of adsorbed fibrinogen in platelet adhesion to polyurethane surfaces: A comparison of surface hydrophobicity, protein adsorption, monoclonal antibody binding, and platelet adhesion", Journal of Biomedical Materials Research, Part A, Sep. 15, 2005, vol. 74A, No. 4, pp. 722-738.
Xu, Ruijian et al., "Low permeability biomedical polyurethane nanocomposites", Journal of Miomedical Materials Resarch, 2003, vol. 64A, pp. 114-119.
Yang, M. et al., J. biomed. Mater. Res. 48 (1999) 13-23.
Yeh, J. et al., "Moisture diffusivity of Biomer® versus Biomer®-coated Polyisobutylene polyurethane urea (PIB-PUU): a potential blood sac material for the artificial heart", Journal of Materials Science Letters 13(19), 1994, pp. 1390-1391.
International Search Report issued in PCT/US2009/048845, mailed Oct. 6, 2009, 3 pages.
International Search Report issued in PCT/US2009/048827, mailed Oct. 6, 2009, 3 pages.
Santos, R. et al., "New Telechelic Polymers and Sequential Copolymers by Polyfunctional Initiator-Transfer-Agents (Inifers)", Polymer Bulletin, 11:341-348 (1984).
Wohlfarth, C., "Permittivity (Dielectric Constant) of Liquids", CRC Handbook, 91st ed. 2010-2011, p. 6-186 to 6-207.

Non-Final Office Action issued in U.S. Appl. No. 11/400,059, mailed Apr. 11, 2011.
Erdodi, G., et al., "Polyisobutylene-Based Polyurethanes. VI. Unprecedented Combination of Mechanical Properties and Oxidative/Hydrolytic Stability by H-Bond Acceptor Chain Extenders" J. Polym. Sci., Part A: Polym. Chem, 48:2361-2371 (2010).
Kang, Jungmee et al, "PIB-Based Polyurethanes. IV. The Morphology of Polyurethanes Containing Soft Co-Segments", Journal of Polymer Science Part A: Polymer Chemistry, vol. 47, 6180-6190 (2009).
Kang, Jungmee et al., "Rendering Polyureas Melt Processible", Journal of Polymer Science Part A: Polymer Chemistry, vol. 49, 2461-2467 (2011).
Kang, Jungmee et al., Polyisobutylene-Based Polyurethanes. V. Oxidative-Hydrolytic Stability and Biocampatibility, Journal of Polymer Science: Part A: Polymer Chemistry, vol. 48, 2194-2203 (2010).
Notice of Allowance issued in U.S. Appl. No. 12/492,483, mailed Jul. 13, 2012, 9 pages.
Faust, R. et al., "Method to Prepare Block Copolymers by the Combination of Cationic and Anionic Polymerization", U.S. Appl. No. 12/225,905, filed Apr. 5, 2007.
Non-Final Office Action issued in U.S. Appl. No. 12/492,483, mailed Nov. 21, 2011, 11 pages.
Tan, J. et al., "In Vivo Biostability Study of a New Lead Insulation Material," Cardiostim 2006, Europace Supplements, 8, 179PW/9 (2006).
Wright, James I., "Using Polyurethanes in Medical Applications", 5 pages. Downloaded from http://www.cmdm.com on Oct. 17, 2006.
International Search Report and Written Opinion issued in PCT/US2013/053448, mailed Apr. 28, 2014,11 pgs.
International Preliminary Report on Patentability, Chapter II, issued in PCT/US2006/035064, dated Sep. 12, 2007, 12 pages.
International Search Report and Written Opinion issued in PCT/US2006/035064, mailed Jan. 23, 2007, 12 pages.
International Search Report and Written Opinion issued in PCT/US2007/007558, mailed Sep. 20, 2007.
Kirby, Darren, "Use of a Bioactive Material on a Pacemaker Electrode for the Purpose of Enhancing Heart Pace/Sense Efficiency", MSC Biomedical Engineering, Thesis, Trinity College Dublin (2003).
Office Action issued in EP 07754128 mailed Mar. 31, 2010.
Office Action issued in EP Application No. 07754128.2, Mailed Feb. 19, 2009, 3 pages.
Response filed Aug. 31, 2009 to Office Action dated Feb. 19, 2009, EP App 07754128.
York, P., "New Materials and Systems for Drug Delivery and Targeting", Chemical Aspects of Drug Delivery Systems, Copyright 1996, pp. 1-10, proceedings from a symposium held Apr. 17-18, 1996 at Salford University.
"Butyl Rubber Properties and Applications", downloaded form URL: hiit://ww.iisrp.com/WebPolymers/02ButylRubberIIR.pdf availale on the internet on Jul. 31, 2007 according to Wayback Web Archive.
Communication in Cases for Which no. Other Form is Applicable, issued in PCT/US2013/053448, mailed Jul. 28, 2014, 1 page.
International Search Report and Written Opinion issued in PCT/US2010/046072, mailed Oct. 15, 2010, 10 pages.
International Search Report and Written Opinion issued in PCT/US2013/053448, mailed Jul. 28, 2014, correcting earlier version mailed Apr. 28, 2014, 11 pages.
Chen, D., et. al. Amphiphilic Networks: 11. Biocompatibty and Controlled Drug Release of Poly[lsobutylene-co-2-(dimethy1arnino)Ethyl Methacrylate]. J. of Biomedical Materials Research, 23:1327-1342, 1989.
Chen, T. K., et. al. Glass Transition Behaviors of a Polyurethane Hard Segment based on 4, 4'- Diisocyanatodiphenylmethane and 1,4-Butanediol and the Calculation of Microdomain Composition. Macromolecules, 30:5068-5074, 1997.
Cho, J. C., et. al, Synthesis, Characterization, Properties, and Drug Release of Poly(Alkyl Methacrylate-B-Isobutylene-B-Alkyl Methacrylate). Biomacromolecules, 7:2997-3007, 2006.

(56) References Cited

OTHER PUBLICATIONS

Choi, T., et. al. Segmented Polyurethanes Derived from Novel Siloxane--Carbonate Soft Segments for Biomedical Applications. Journal of Polymer Science Part 6: Polymer Physics, 49:865-872, 2011.

Christenson, E. M. et. al. Oxidative Mechanisms of Poly(Carbonate Urethane) and Poly(Ether Urethane) Biodegradation: In Vivo and In Vitro Correlations. J. Biomed. Mater. Res., 70A:245-255, 2004.

Fan, L., et, al. The Absolute Calibration of a Small-Angle Scattering Instrument with a Laboratory X-ray Source. XIV International Conference on Small-Angle Scattering (SAS09), Journal of Physics: Conference Series 247, 11 pages, 2010.

Gunatillake, P. A., et. al. Synthesis and Characterization of a Series of Poly(alkylene carbonate) Macrodiols and the Effect of Their Structure on the Properties of Polyurethanes. Journal of Applied Polymer Science, 69:1621-1633, 1998.

Gyor, M., et. al. Living Carbocationic Polymerization of Isobutylene with Blocked Bifunctional Initiators in the Presence of Di-tert-butylpyridine as a Proton Trap. J. of Macromolecular Science, Part A, Pure Appl. Chem., 29 (8):639-653, 1992.

Hernandez, et. al. R. Microstructural Organization of Three-Phase Polydimethylsiloxane-Based Segmented Polyurethanes. Macromolecules, 40:5441-5449, 2007.

Hernandez, R., et al. A Comparison of Phase Organization of Model Segmented Polyurethanes with Different Intersegment Compatibilities. Macromolecules, 41:9767-9776, 2008.

International Preliminary Report on Patentability and Written Opinion issued May 26, 2015 for International Application No. PCT/US2013/071170, entitled "High Strength Polyisobutylene Polyurethanes".

Ivan, B., et. al. Living Carbocationic Polymerization, XXX, One-Pot Synthesis of Allyl-Terminated Linear and Tri-Arm Star Polyisobutylenes, and Epoxy- and Polyisobutylenes, and Epoxy- and Hydroxy-Telechelics Therefrom. Journal of Polymer Science: Part A: Polymer Chemistry, 28:89-104, 1990.

Ivan, Bela, et. al, New Telechelic Polymers and Sequential Copolymers by Polyfunctional Initiator-Transfer Agents (Inifers). VII. Synthesis and Characterization of (Alpha),(Omega)-Di(Hydroxy) Polyisobutylene. Journal of Polymer Science: Polymer Chemistry Edition, 18:3177-3191, 1980.

Koberstein, J. T., et. al. Compression-Molded Polyurethane Block Copolymers. 1, Microdomain Morphology and ITherrnomechanical Properties. Macromolecules, 25:6195-6204, 1992.

Koberstein, J. T., et. al. Compression-Molded Polyurethane Eilock Copolymers. 2. Evaluationn of Microphase Compositions. Macromolecules, 25:6205-6213, 1992.

Koberstein, J. T., et. al. Simultaneous SAXS-DSC Study of Multiple Endothermic Behavior in Polyether-Based Polyurethane Block Copolymers. Macromolecules, 19:714-720, 1986.

Kunal, K., et, al. Polyisobutylene: A Most Unusual Polymer. Journal of Poymer Science: Part B: Polymer Physics, 46:1390-1399, 2008.

Leung, L. M., et. al. DSC Annealing Study of Microphase Separation and Multiple Endothermic Behavior in Polyether-Based Polyurethane Block Copolymers. Macromolecules, 19:706-713, 1986.

Martin, D. J., et. al, Polydimethylsiloxan/Polyether-Mixed Macrodiol-Based Polyurethane Elastomers: Biostability. Biomaterials, 21:1021-1029, 2000.

Notification of Transmittal of the International Search Report and the Written Opinion of the International Searching Authority for Int'l Application No. PCT/US2013/071170, entitled: High Strength Polyisobutylene Polyurethanes, Date Mailed: Jun. 6, 2014.

Ojha, Umaprasana, et. al. Syntheses and Characterization of Novel Biostable Polyisobutylene Based Thermoplastic Polyurethanes. Polymer 50:3448-3457, 2009.

Pinchuk, L Review: A Review of the Biostability and Carcinogenicity of Polyurethanes in Medicine and the New Generation of 'Biostable' Polyurethanes. J. Biontater. Sci., Polymer Edn., 6(3):225-267, 1994.

Saiani, A., et. al. Origin of Multiple Melting Endotherms in a High Hard Block Content Polyurethane. 1. Thermodynamic Investigation. Macromolecules, 34:9059-9068, 2001.

Saiani, A., et. al. Origin of Multiple Melting Endotherms in a High Hard Block ContentPolyurethane. 2. Structural Investigation. Macromolecules, 37:1411-1421, 2004.

Speckhard, T. A., et. al. Properties of Polyisobutylene Polyurethane Block Copolymers: 2. Macroglycols Produced by the "Inifer" Technique. Polymer, 26:55-69, 1985.

Stokes, K., et. al. Polyurethane Elastomer Biostability. Journal of Biomaterials Applications, 9.321-354, 1995.

Zhang, F., et. al. Glassy Carbon as an Absolute Intensity Calibration Standard for Small-Angle Scattering. Metallurgical and Materials Transactions A, 41A:1151-1158, May 2010.

Mitzner, E., et. al. Modification of Segmented Poly(Ether Urethanes) by Incorporation of Poly(lsobutylene)Glycol. Journal of Macromolecular Science, Part A., Pure and Applied Chemistry, 34(1):165-178, 1997.

* cited by examiner

POLYISOBUTYLENE-BASED POLYURETHANES

RELATED APPLICATIONS

This application claims the benefit of U.S. Provisional Application No. 61/204,856, filed on Jan. 12, 2009, U.S. Provisional Application No. 61/211,310, filed on Mar. 26, 2009, and U.S. Provisional Application No. 61/279,629, filed on Oct. 23, 2009. The entire teachings of the above applications are incorporated herein by reference.

PARTIES TO A JOINT RESEARCH AGREEMENT

The claimed invention was made subject to a joint research agreement between Boston Scientific Corporation and the University of Massachusetts Lowell. Cardiac Pacemakers, Inc. is a wholly-owned subsidiary of Boston Scientific Corporation.

BACKGROUND OF THE INVENTION

Thermoplastic polyurethanes, polyureas and polyurethaneureas represent an important family of segmented block copolymer thermoplastic elastomers. They can be extruded, injection or compression molded or solution spun. They offer a broad range of physical properties and characteristics, including high tensile and tear strength, chemical and abrasion resistance, good processibility, and protective barrier properties. Depending on composition, i.e. on the volume fraction of the soft, elastomeric segments, these polymers can be soft, rubbery or hard and rigid materials. The hard segments of polyurethanes are composed of diisocyanate and a small molecule diol chain extender, while the soft segments are mostly low molecular weight polymeric diols. Similarly, polyureas or polyurethaneureas comprise diamines and a combination of diols and diamines, respectively, in addition to diisocyanate. Polymeric diols include polyester diols, polyether diols, and polydiene diols. The polyester component is prone to hydrolytic degradation, the polyether component does not have sufficient resistance to oxidative degradation, especially in vivo, and polydienes suffer from inadequate thermal and oxidative stability.

Polyurethanes are the most commonly used materials in the production of biomedical devices that come in contact with blood such as pacemakers, defibrillators, angioplasty balloons, surgical drains, dialysis devices, etc. However, polyurethanes generally exhibit insufficient long-term in vivo biostability due to oxidation of the polyether soft segment, especially when in contact with metals, which catalyze oxidative degradation. This deficiency, limits the use of polyurethanes for long-term applications.

Polyisobutylene (PIB)-based thermoplastic polyurethanes (TPUs) offer high thermal, oxidative, and hydrolytic stability, however, polyisobutylene polyurethanes exhibit insufficient mechanical properties.

SUMMARY OF THE INVENTION

It has now been discovered that incorporation of polyether diols into the PIB-based soft segments (e.g. 10-30% by weight of the soft segment) produces elastomeric polymer with significantly improved mechanical properties, processibility, and resistance to oxidative degradation.

In one embodiment, the present invention is an elastomeric polymer, comprising (1) a hard segment in the amount of 10% to 60% by weight of the elastomeric polymer, wherein the hard segment includes a urethane, urea or urethaneurea; and (2) a soft segment in the amount of 40% to 90% by weight of the elastomeric polymer. Preferably, the soft segment comprises (a) at least 2% by weight of the soft segment of at least one polyether macrodiol, and/or at least one polycarbonate macrodiol; and (b) at least 2% by weight of the soft segment of at least one polyisobutylene macrodiol or diamine. Preferably, the number average molecular weight of the elastomeric polymer is not less than about 40 kilodaltons. In other embodiments, the number average molecular weight of the elastomeric polymer is not less than about 50 kilodaltons.

In another embodiment, the present invention is an article of manufacture, comprising: an elastomeric polymer, said elastomeric polymer, including (1) a hard segment in the amount of 10% to 60% by weight of the elastomeric polymer, wherein the hard segment includes a urethane, urea or urethaneurea; and (2) a soft segment in the amount of 40% to 90% by weight of the elastomeric polymer. Preferably, the soft segment comprises (a) at least 2% by weight of the soft segment of at least one polyether macrodiol, and/or at least one polycarbonate macrodiol; and (b) at least 2% by weight of the soft segment of at least one polyisobutylene macrodiol or diamine. Preferably, the number average molecular weight of the elastomeric polymer is not less than about 40 kilodaltons. In other embodiments, the number average molecular weight of the elastomeric polymer is not less than about 50 kilodaltons.

In another embodiment, the present invention is a process for preparing an elastomeric polymer. The process comprises the steps of (a) forming a mixture that includes at least one polyisobutylene macrodiol, and/or diamine, at least one polyether macrodiol and a chain extender; and (b) reacting the mixture with a diisocyanate to yield a polyurethane elastomeric polymer. Preferably, the elastomeric polymer includes (i) a hard segment in the amount of 10% to 60% by weight of the elastomeric polymer, wherein the hard segment includes a urethane, urea or urethaneurea; and (ii) a soft segment in the amount of 40% to 90% by weight of the elastomeric polymer. Preferably, the soft segment includes at least 2% by weight of the soft segment of at least one polyether macrodiol, and/or at least one polycarbonate macrodiol, and at least 2% by weight of the soft segment of the at least one polyisobuylene macrodiol and/or diamine. Preferably, the number average molecular weight of the elastomeric polymer is not less than about 40 kilodaltons In other embodiments, the number average molecular weight of the elastomeric polymer is not less than about 50 kilodaltons.

In another embodiment, the present invention is a process for preparing a elastomeric polymer. The process comprises the steps of (a) reacting a diisocyanate with a mixture that includes at least one polyisobutylene macrodiol, and/or diamine, and at least one polyether macrodiol to form a prepolymer having terminally reactive diisocyanate groups; and (b) reacting the prepolymer with a chain extender to yield an elastomeric polymer. Preferably, the elastomeric polymer includes (i) a hard segment in the amount of 10% to 60% by weight of the elastomeric polymer, wherein the hard segment includes a urethane, urea or urethaneurea; and (ii) a soft segment in the amount of 40% to 90% by weight of the elastomeric polymer. Preferably, the soft segment includes at least 2% by weight of the soft segment of the at least one polyether macrodiol and/or at least one polycarbonate macrodiol, and at least 2% by weight of the soft segment of the at least one polyisobuylene macrodiol and/or diamine. Preferably, the number average molecular weight of the elastomeric polymer is not less than about 40 kilodaltons. In other embodiments, the number average molecular weight of the elastomeric polymer is not less than about 50 kilodaltons.

The polyisobutylene-based, polyether-containing thermoplastic polyurethanes of the present invention can be used to manufacture elastomeric materials useful in the production of biomedical devices such as pacemakers, defibrillators, angioplasty balloons, surgical drains, dialysis devices, etc. The elastomeric materials of the present invention possess a number of advantages over previously disclosed materials, including other polyisobutylene (PIB) based polyurethanes. Specifically, as described in the Exemplification section, adding a polyether (e.g. polytetramethyleneoxide diol, PTMO) to the PIB-based soft segment improves tensile strength and percent elongation. As demonstrated in Example 13, the PIB-based TPUs containing PTMO showed significant oxidative stability as compared to the commercial controls such as Pellethane™ 2686-55D and 2686-80A. After 12 weeks in vitro (equivalent of approximately 10 years in vivo) the PIB-PTMO TPUs with 10-20% PTMO in the soft segment showed 6-15% weight loss whereas the Pellethanes™ degraded completely in about 9 weeks. The weight loss was linearly proportional to the PTMO content in the PIB-PTMO TPUs.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Glossary

Figure 1:
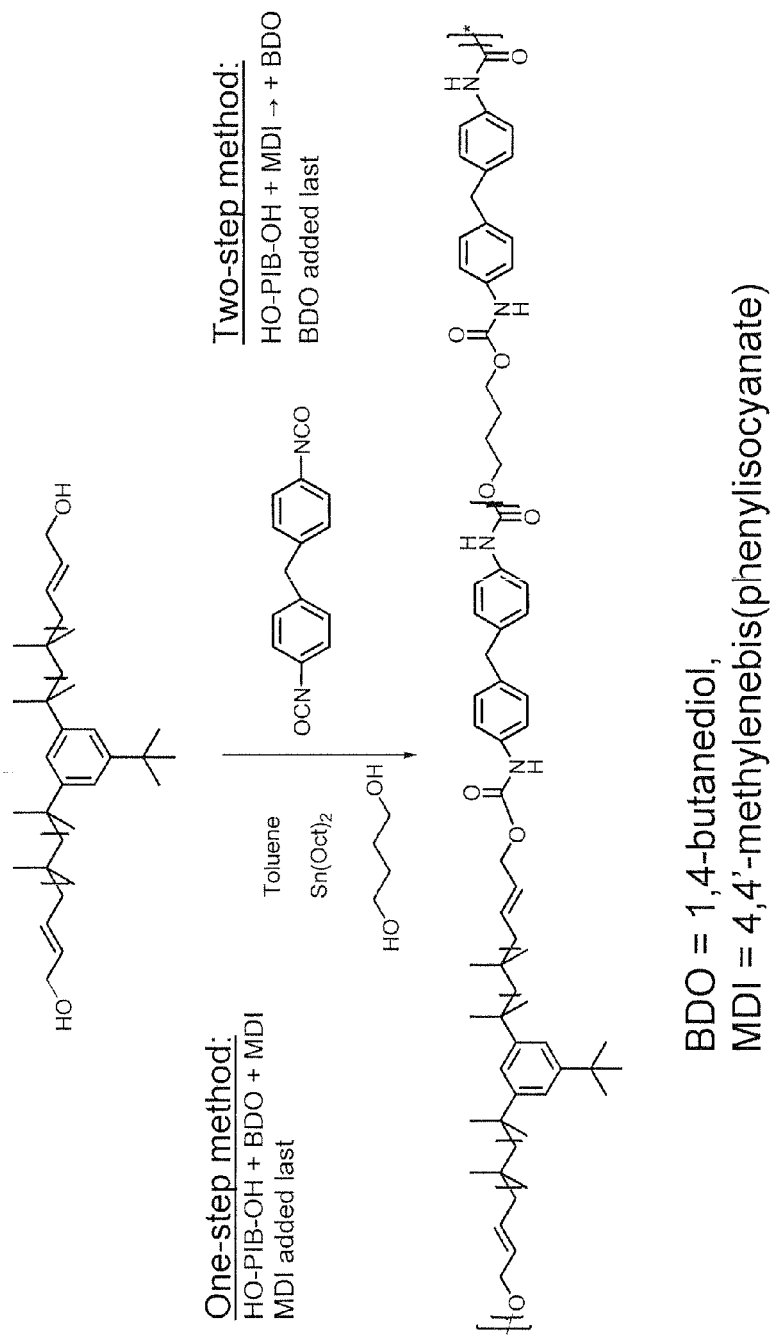
FIG. 1 is a schematic diagram of an example of a synthetic procedure employed to produce the polyisobutylene-containing thermoplastic polyurethanes that can be employed by the present invention.

As used herein, the term "polydispersity index" (PDI) means is a measure of the distribution of molecular mass in a given polymer sample. The PDI calculated is the weight average molecular weight divided by the number average molecular weight.

As used herein, the term "macrodiol" means a polymeric diol. Examples include polyether compounds of formula

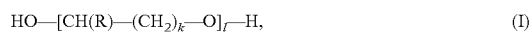

$$HO-[CH(R)-(CH_2)_k-O]_l-H, \quad (I)$$

and polyisobutylene polymers of formula

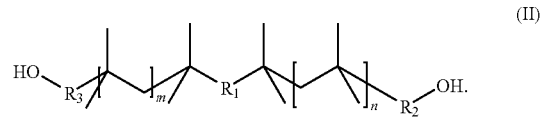

(II)

Values and preferred values for the variables in formulas (I) and (II) are defined below.

Similarly, the phrase "macrodiol and/or diamine" is used, the reference is being made to a polymeric diamine similar in structure to the diols of formula (II), in which the terminal hydroxyl groups are replaced with amino or alkylamino-groups, as defined below.

As used herein, the term "telechelic", when referring to a polymer, means a polymer carrying functionalized end-groups. Examples of telechelic polymers are difunctional polymers of formulas (I) and (II), above. Telechelic polymers can be used, e.g., for the synthesis of block copolymers.

As used herein, the term "BDO" refers to 1,4-butanediol.

As used herein, the term "MDI" refers to 4,4'-methylen-ebis(phenylisocyanate).

As used herein, the term "PTMO" refers to polytetramethylene oxide.

As used herein, the term "PIB" means a polyisobutylene, i.e. a compound formed by polymerization of an optionally substituted butadiene.

As used herein, the term "TPU" means a thermoplastic polyurethane.

As used herein, the term "PIB-TPU" means a polyisobutylene-based thermoplastic polyurethane obtained by any known process. The term includes the elastomeric polyurethanes materials described herein.

As used herein, the term "PIB-PTMO-TPU" means a polyisobutylene-based, polytetramethylene oxide-containing thermoplastic polyurethane obtained by any known process and includes the elastomeric polyurethanes materials described herein.

As used herein, the term "initiator residue" refers to a difunctional chemical moiety, that links two linear chains of a polymer. For example, in a polyisobutylene polymer of formula

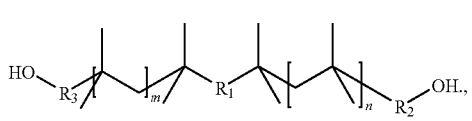

(II)

where values and preferred values for the variables are defined below, $R_1$ is an initiator residue. Examples of initiator residues include dicumyl and 5-tert-butyl-1,3 dicumyl that correspond to dicumyl chloride, methylether or ester, respectively, are used as initiator. Other examples include 2,4,4,6-tetramethylheptylene or 2,5-dimethylhexylene, which arise when 2,6-dichloro-2,4,4,6-tetramethylheptane or 2,5-dichloro-2,5-dimethylhexane is used as initiator. Many other cationic mono- and multifunctional initiators are known in the art.

Definitions of Terms

The term "alkyl", as used herein, unless otherwise indicated, means straight or branched saturated monovalent hydrocarbon radicals of formula $C_nH_{2n+1}$. In some embodiments, n is from 1 to 18. In other embodiments, n is from 1 to 12. Preferably, n is from 1 to 6. In some embodiments, n is 1-1000, for example, n is 1-100. Alkyl can optionally be substituted with —OH, —SH, halogen, amino, cyano, nitro, a C1-C12 alkyl, C1-C12 haloalkyl, C1-C12 alkoxy, C1-C12 haloalkoxy or C1-C12 alkyl sulfanyl. In some embodiments, alkyl can optionally be substituted with one or more halogen, hydroxyl, C1-C12 alkyl, C2-C12 alkenyl or C2-C12 alkynyl group, C1-C12 alkoxy, or C1-C12 haloalkyl. The term alkyl can also refer to cycloalkyl.

The term "cycloalkyl", as used herein, means saturated cyclic hydrocarbons, i.e. compounds where all ring atoms are carbons. In some embodiments, a cycloalkyl comprises from 3 to 18 carbons. Preferably, a cycloalkyl comprises from 3 to 6 carbons. Examples of cycloalkyl include, but are not limited to, cyclopropyl, cyclobutyl, cyclopentyl, cyclohexyl, and cycloheptyl. In some embodiments, cycloalkyl can optionally be substituted with one or more halogen, hydroxyl, C1-C12 alkyl, C2-C12 alkenyl or C2-C12 alkynyl group, C1-C12 alkoxy, or C1-C12 haloalkyl.

The term "haloalkyl", as used herein, includes an alkyl substituted with one or more F, Cl, Br, or I, wherein alkyl is defined above.

The terms "alkoxy", as used herein, means an "alkyl-O—" group, wherein alkyl is defined above. Examples of alkoxy group include methoxy or ethoxy groups.

The term "aryl", as used herein, refers to a carbocyclic aromatic group. Preferably, an aryl comprises from 6 to 18 carbons. Examples of aryl groups include, but are not limited to phenyl and naphthyl. Examples of aryl groups include optionally substituted groups such as phenyl, biphenyl, naphthyl, phenanthryl, anthracenyl, pyrenyl, fluoranthyl or fluorenyl. An aryl can be optionally substituted. Examples of suitable substituents on an aryl include halogen, hydroxyl, C1-C12 alkyl, C2-C12 alkene or C2-C12 alkyne, C3-C12 cycloalkyl, C1-C12 haloalkyl, C1-C12 alkoxy, aryloxy, arylamino or aryl group.

The term "aryloxy", as used herein, means an "aryl-O—" group, wherein aryl is defined above. Examples of an aryloxy group include phenoxy or naphthoxy groups.

The term arylamine, as used herein, means an "aryl-NH-", an "aryl-N(alkyl)-", or an "(aryl)$_2$-N-" groups, wherein aryl and alkyl are defined above.

The term "heteroaryl", as used herein, refers to aromatic groups containing one or more heteroatoms (O, S, or N). A heteroaryl group can be monocyclic or polycyclic, e.g. a monocyclic heteroaryl ring fused to one or more carbocyclic aromatic groups or other monocyclic heteroaryl groups. The heteroaryl groups of this invention can also include ring systems substituted with one or more oxo moieties. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

The foregoing heteroaryl groups may be C-attached or N-attached (where such is possible). For instance, a group derived from pyrrole may be pyrrol-1-yl (N-attached) or pyrrol-3-yl (C-attached).

Suitable substituents for heteroaryl are as defined above with respect to aryl group.

Suitable substituents for an alkyl, cycloalkyl include a halogen, an alkyl, an alkenyl, a cycloalkyl, a cycloalkenyl, an aryl, a heteroaryl, a haloalkyl, cyano, nitro, haloalkoxy.

Further examples of suitable substituents for a substitutable carbon atom in an aryl, a heteroaryl, alkyl or cycloalkyl include but are not limited to —OH, halogen (—F, —Cl, —Br, and —I), —R, —OR, —CH$_2$R, —CH$_2$OR, —CH$_2$CH$_2$OR. Each R is independently an alkyl group.

In some embodiments, suitable substituents for a substitutable carbon atom in an aryl, a heteroaryl or an aryl portion of an arylalkenyl include halogen, hydroxyl, C1-C12 alkyl, C2-C12 alkenyl or C2-C12 alkynyl group, C1-C12 alkoxy, aryloxy group, arylamino group and C1-C12 haloalkyl.

In addition, the above-mentioned groups may also be substituted with =O, =S, =N-alkyl.

In the context of the present invention, an amino group may be a primary (—NH$_2$), secondary (—NHR$_p$), or tertiary (—NR$_p$R$_q$), wherein R$_p$ and R$_q$ may be any of the alkyl, alkenyl, alkynyl, alkoxy, cycloalkyl, cycloalkoxy, aryl, heteroaryl, and a bicyclic carbocyclic group. A (di)alkylamino group is an instance of an amino group substituted with one or two alkyls.

A trialkylamino group is a group N$^+$(Rt)$_3$, wherein Rt is an alkyl, as defined above.

Polyurethanes and Polyureas

As used herein, a "polyurethane" is any polymer consisting of a chain of organic units joined by urethane (carbamate, —NH—COO—) links. Polyurethane polymers can be formed by reacting a molecules containing at least two isocyanate functional groups with another molecule containing at least two alcohol (hydroxyl) groups. By reacting an isocyanate group, —N=C=O, with a hydroxyl group, —OH, a urethane linkage is produced. A catalyst can be used. Similarly, in polyureas the links are urea groups (—NH—CO—NH—) that are obtained by reacting an isocyanate group with an amine group —NH$_2$.

For example, polyurethanes can be produced by the polyaddition reaction of a polyisocyanate with a polyalcohol (a polyol, an example of which is a macrodiol). The reaction mixture can include other additives. A polyisocyanate is a molecule with two or more isocyanate functional groups, $R^1$—(N=C=O)$_{n\geq2}$ and a polyol is a molecule with two or more hydroxyl functional groups, $R^2$—(OH)$_{n>2}$. $R^1$ and $R^2$ are each independently an aliphatic or an aromatic moiety. The reaction product is a polymer containing the urethane linkage, —$R^1$NHCOOR$^2$—.

Polyisocyanate that contain two isocyanate groups are called diisocyanates. Isocyanates can be aromatic, such as diphenylmethane diisocyanate (MDI) or toluene diisocyanate (TDI); or aliphatic, such as hexamethylene diisocyanate (HDI) or isophorone diisocyanate (IPDI). An example of an isocyanate is polymeric diphenylmethane diisocyanate, which is a blend of molecules with two-, three-, and four- or more isocyanate groups, with an average functionality of 2.7.

Polyols that contain two hydroxyl groups are called macrodiols, those with three hydroxyl groups are called macrotriols. Examples of polyols include polycarbonate polyols, polycaprolactone polyols, polybutadiene polyols, and polysulfide polyols.

Additive such as catalysts, surfactants, blowing agents, cross linkers, flame retardants, light stabilizers, and fillers are used to control and modify the reaction process and performance characteristics of the polymer.

Examples of aromatic isocyanates are toluene diisocyanate (TDI) and diphenylmethane diisocyanate (MDI). TDI consists of a mixture of the 2,4- and 2,6-diisocyanatotoluene isomers. Another example of an aromatic isocyanate is TDI-80 (TD-80), consisting of 80% of the 2,4-isomer and 20% of the 2,6-isomer.

Examples of aliphatic (including cycloaliphatic) isocyanates are 1,6-hexamethylene diisocyanate (HDI), 1-isocyanato-3-isocyanatomethyl-3,5,5-trimethyl-cyclohexane (isophorone diisocyanate, IPDI), and 4,4'-diisocyanato dicyclohexylmethane (H$_{12}$MDI). Other aliphatic isocyanates include cyclohexane diisocyanate (CHDI), tetramethylxylene diisocyanate (TMXDI), and 1,3-bis(isocyanatomethyl)cyclohexane (H$_6$XDI).

Chain extenders (f=2) and cross linkers (f=3 or greater) are low molecular weight hydroxyl and amine terminated compounds that play an important role in the polymer morphology of polyurethane fibers, elastomers, adhesives, and certain integral skin and microcellular foams. Examples of chain extenders and cross linkers are ethylene glycol (EG), 1,4-butanediol (BDO), diethylene glycol (DEG), glycerine, and trimethylol propane (TMP).

The elastomeric properties of polyurethanes, polyureas and polyurethaneureas are derived from the phase separation of the "hard segment" and the "soft segment" domains of the polymer chain. For example, hard segments that comprise urethane units can serve as cross-links between the soft segments that comprise polyol (e.g., macrodiol) units (e.g., polyisobutane diols, polyether diols, and/or polyester diols). Without being limited to any particular theory, it is believed that the phase separation occurs because the mainly nonpolar, low melting soft segments are incompatible with the polar, high melting hard segments. The polyol-containing soft segments are mobile and are normally present in coiled formation, while the isocyanate-containing hard segments (which can also include chain extenders) are stiff and immobile. Because the hard segments are covalently coupled to the soft segments, they inhibit plastic flow of the polymer chains, thus creating elastomeric resiliency. Upon mechanical deformation, a portion of the soft segments are stressed by uncoiling, and the hard segments become aligned in the stress direction. This reorientation of the hard segments and consequent powerful hydrogen bonding contributes to high tensile strength, elongation, and tear resistance values.

Although the synthesis of polyurethanes is usually presented as proceeding via formation of urethane (carbamate) linkages by the reaction of isocyanates and alocohols, this is an oversimplification. See, for example, G. ODIAN: PRINCIPLES OF POLYMERIZATION, FOURTH ED. Wiley Interscience, 2004. Accordingly, it is more convenient to define the polyurethane compositions via weight percent of the components rather than structurally.

Accordingly, in some embodiments, the present invention is an elastomeric polymer, comprising (1) a hard segment in the amount of 10% to 60% by weight of the elastomeric polymer, wherein the hard segment includes a urethane, urea or urethaneurea; and (2) a soft segment in the amount of 40% to 90% by weight of the elastomeric polymer. The soft segment comprises at least 2% by weight of the soft segment of at least one polyether macrodiol, and/or at least one polycarbonate macrodiol and at least 2% by weight of the soft segment of at least one polyisobutylene macrodiol and/or diamine.

In certain embodiments, the number average molecular weight of the elastomeric polymer is not less than about 40 kilodaltons (kDa). In other embodiments, the number average molecular weight of the elastomeric polymer is not less than about 50 kilodaltons. In alternative embodiments, wherein the number average molecular weight of the elastomeric polymer is not less than about 60 kDa, not less than about 70 kDa, not less than about 80 kDa, not less than about 90 kDa, not less than about 100 kDa, not less than about 110 kDa, not less than about 120 kDa, not less that about 130 kDa, not less than about 140 kDa or not less than about 150 kDa.

In certain embodiments, the hard segment can be present in the amount of 15, 20, 25, 30, 35, 40, 45, 50, or 55%.

In certain embodiments, soft segment is present in the amount of 45, 50, 55, 60, 65, 70, 75, 80, or 85%. Polyether and/or polycarbonate can be present in the amount of 5, 10, 15, 20, 25, 30, 35, 40, 45, 50, 55, 60, 65, 70, 75, 80 or 85%. Polyisobutylene can be present in the amount of 5, 10, 15, 20, 25, 30, 35, 40, 45, 50, 55, 60, 65, 70, 75, 80 or 85%.

One of ordinary skill can easily determine a suitable polyether macrodiol. Preferably, at least one polyether macrodiol is a compound of formula

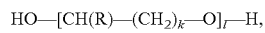

wherein R, for each occurrence, is independently a C1-C12 alkyl or —H; k is an integer not less than 1; and l is an integer not less than 1.

One of ordinary skill can easily determine a suitable polyisobutylene macrodiol or diamine. Preferably, at least one polyisobutylene macrodiol and/or diamine is of formula:

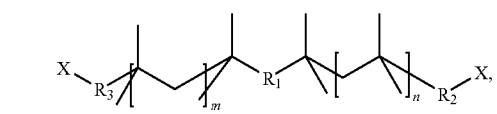

wherein each X is independently —OH, —NH$_2$ or —NHR$_4$, and wherein R$_1$ is an initiator residue (defined above). R$_2$, R$_3$ and R$_4$ is each independently a C1-C16 alkyl, a C3-C16 cycloalkyl, a C2-C16 alkenyl, a C3-C16 cycloalkenyl, a C2-C16 alkynyl, a C3-C16 cycloalkynyl, or a C6-C18 aryl, wherein, for each occurrence, R$_2$ or R$_3$ is, independently, optionally substituted with one or more groups selected from halo, cyano, nitro, dialkylamino, trialkylamino, C1-C16 alkoxy and C1-C16 haloalkyl. Integers n and m are each, independently, from 1 to 500.

Preferably, the polyisobutylene macrodiol or diamine is hydroxy or amino allyl telechelic polyisobutylene. In one embodiment, the molecular weight of at least one polyisobutylene macrodiol or diamine is about 400 Da to about 6000 Da. For example, polyisobutylene macrodiol or diamine is about 500, 1000, 2000, 3000, 4000, or 5000 Da. In certain embodiments, the molecular weight of at least one polyisobutylene macrodiol or diamine is about 1000 Da to about 3000 Da. For example, the molecular weight of at least one polyisobutylene macrodiol or diamine is about 1000, 1500, 2000, or 2500 Da.

In preferred embodiments, R$_2$ and R$_3$ is each independently a moiety selected from —CH$_2$—CH=CH—CH$_2$—, —CH$_2$—CH$_2$—CH$_2$—CH$_2$—, —CH$_2$—CH$_2$—CH$_2$—, and —CH$_2$—CH(CH$_3$)—CH$_2$—.

In one embodiment, the elastomeric polymer of the present invention comprises a soft segment that includes at least one polyether macrodiol and at least one polycarbonate macrodiol; and at least 2% by weight of the soft segment of the at least one polyisobutylene macrodiol, and/or diamine.

In another embodiment, the elastomeric polymer of the present invention comprises a soft segment that includes: (a) about 10% to about 90% by weight of the soft segment of the at least one polyisobutylene macrodiol, and/or diamine; and (b) either about 10% to about 90% by weight of the soft segment of the at least one polyether macrodiol, or about 10% to about 90% by weight of the soft segment of the at least one polycarbonate macrodiol, or about 10% to about 90% by weight of the soft segment of the at least one polyether macrodiol and the at least one polycarbonate macrodiol.

For example, the soft segment can include from about 10% to about 30% by weight of the soft segment of at least one polycarbonate macrodiol. For example, the soft segment can include at least one polycarbonate macrodiol in the amount of 15, 20 or 25%. Alternatively, the soft segment can include from about 10% to about 30% by weight of the soft segment of the at least one polyether macrodiol and the at least one polycarbonate macrodiol. For example, the soft segment can include at least one polyether macrodiol and the at least one polycarbonate macrodiol in the amount of 15, or 25%.

In one embodiment, the soft segment can include from about 10% to about 30% by weight of the soft segment of the at least one polyether macrodiol. For example, the soft segment can include at least one polyether macrodiol in the amount of 15, 20 or 25%.

In another embodiment, the soft segment includes from about 10% to about 90% by weight of the soft segment of the at least one polyisobutylene macrodiol, and/or diamine. For example, the soft segment can include at least one polyisobutylene macrodiol, and/or diamine in the amount of 20, 30, 40, 50, 60, 70 or 80%.

In a further embodiment, the soft segment can include from about 70% to about 90% by weight of the soft segment of the at least one polyisobutylene macrodiol, and/or diamine. For example, the soft segment can include at least one polyisobutylene macrodiol, and/or diamine in the amount of 70, 75, 80 or 85%.

Preferably, at least one polyether macrodiol includes at least one member selected form the group consisting of poly(ethylene oxide) diol, polypropylene oxide) diol, poly(trimethylene oxide) diol, poly(tetramethylene oxide) diol, poly(hexamethylene oxide) diol, poly(heptamethylene oxide) diol, poly(octamethylene oxide) diol and poly(decamethylene oxide) diol.

One of ordinary skill in the art will be able to easily determine a suitable polycarbonate macrodiol. Preferably, at least one polycarbonate macrodiol includes at least one member selected from the group consisting of a poly(alkylene carbonate) of a formula

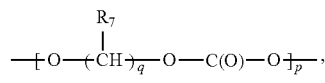

where R$_7$ is a hydrogen, a C1-C12 straight or branched alkyl, or a C3-C12 cycloalkyl, q is an integer greater than 1 and p is an integer greater than 2. Preferably, R$_7$ is a hydrogen. Examples of poly(alkylene carbonate) include poly(tetramethylene carbonate) diol, poly(pentamethylene carbonate) diol, poly(hexamethylene carbonate) diol, or copolymers of thereof.

In certain embodiments, the elastomeric polymer of the present invention comprises a hard segment present in the amount of from about 30% to about 50% by weight of the elastomeric polymer. For example, the hard segment present in the amount of 35, 40, or 45%.

Examples of the hard segments include the hard segments formed by reacting a diisocyanate with a chain extender. One of ordinary skill in the art will easily determine a suitable diisocyanate or a chain extender. The diisocyanate can be at least one member selected from the group consisting of 4,4'-methylenephenyl diisocyanate; methylene diisocyanate; p-phenylene diisocyanate; cis-cyclohexane-1,4-diisocyanate; trans-cyclohexane-1,4-diisocyanate; a mixture of cis cis-cyclohexane-1,4-diisocyanate and trans-cyclohexane-1,4-diisocyanate; 1,6-hexamethylene diisocyanate; 2,4-toluene diisocyanate; cis-2,4-toluene diisocyanate; trans-2,4-toluene diisocyanate; a mixture of cis-2,4-toluene diisocyanate and trans-2,4-toluene diisocyanate; p-tetramethylxylene diisocyanate; and m-tetramethylxylene diisocyanate. The chain extender can be at least one member selected from the group consisting of 1,4-butanediol; 1,5 pentanediol; 1,6-hexanediol; 1,8-octanediol; 1,9-nonanediol; 1,10-decanediol, 1,12-dodacanediol; 1,4-cyclohexane dimethanol; p-xyleneglycol and 1,4-bis(2-hydroxyethoxy) benzene. Preferably, the diisocyanate is 4,4'-methylenephenyl diisocyanate and the chain extender is 1,4-butanediol.

In a preferred embodiment, the polyurethane elastomeric polymer of the present invention comprises the soft segment formed from a hydroxyallyl telechelic polyisobutylene and poly(tetramethylene oxide) diol and the hard segment formed from 4,4'-methylenediphenyl diisocyanate and 1,4-butanediol.

In another preferred embodiment, the polyurethane elastomeric polymer of the present invention comprises the soft segment is derived from a hydroxyallyl telechelic polyisobutylene and poly(hexamethylene oxide) diol and the hard segment is derived from 4,4'-methylenediphenyl diisocyanate and 1,4-butanediol.

In another preferred embodiment, the polyurethane elastomeric polymer of the present invention comprises the soft segment formed from (a) a hydroxyallyl difunctional polyisobutylene and (b) poly(tetramethylene oxide) diol or poly (hexamethylene oxide) diol; and the hard segment formed from (c) 4,4'-methylenediphenyl diisocyanate and (d) 1,4-butanediol.

In certain embodiments, the present invention is an article of manufacture comprising any of the polyurethane elastomeric polymers described above. In preferred embodiments, the article is a medical device or an implant. Examples of the article of the present invention include a cardiac pacemaker, a defibrillator, a catheter, an implantable prosthesis, a cardiac assist device, an artificial organ, a pacemaker lead, a defibrillator lead, a blood pump, a balloon pump, an a-V shunt, a biosensor, a membrane for cell encapsulation, a drug delivery device, a wound dressing, an artificial joint, an orthopedic implant or a soft tissue replacement. In other embodiments, the article is a fiber, film, engineering plastic, fabric, coating, and adhesive joint.

The methods of synthesis of polyurethane compositions are generally well known by one of ordinary skill in the art of polymer chemistry. See, for example, Gunter Oertel, "Polyurethane Handbook", 2nd ed. Hanser Publishers (1993); or Malcolm P. Stevens, "Polymer Chemistry", 3d ed. Oxford University Press (1999). The relevant portions of these publications are incorporated herein by reference.

The present invention is based, in part, on the discovery of new and improved methods of polyurethane synthesis. Accordingly, in some embodiments, the present invention is a process for preparing a polyurethane elastomeric polymer. (See FIG. 2 for an example of such a procedure.) Generally, the process comprises the steps of (a) forming a mixture that includes at least one polyisobutylene macrodiol, and/or diamine, at least one polyether macrodiol and a chain extender; and (b) reacting the mixture with a diisocyanate to yield a polyurethane elastomeric polymer. Preferably, the elastomeric polymer includes (i) a hard segment in the amount of 10% to 60% by weight of the elastomeric polymer, wherein the hard segment includes a urethane, urea or urethaneurea; and (ii) a soft segment in the amount of 40% to 90% by weight of the elastomeric polymer. Preferably, the soft segment includes at least 2% by weight of the soft segment of at least one polyether macrodiol, and/or at least one polycarbonate macrodiol, and at least 2% by weight of the soft segment of the at least one polyisobuylene macrodiol, and/or diamine.

Any one or more of the isocyanates, polyols, chain extenders, or various additives can be employed with the synthetic method of the present invention. For example, polyether macrodiols and/or polyisobutylene macrodiol, described above, as well as any mixture thereof, can be used in the above-described process. Any amounts of the components and their combinations described above can be used.

Preferably, in the processes of the present invention, the mixture is formed at a temperature of about 45° C. to about 120° C. For example, the mixture is formed at a temperature of about 50, 60, 70, 80, 90, 100 or 110° C.

In some embodiments, the mixture is formed in the presence of a catalyst, such as stannous octoate. Other catalysts are well known in the art and can be used by one of ordinary skill in the art.

In an alternative embodiments, the present invention is a process for preparing a elastomeric polymer, comprising the steps of (a) reacting a diisocyanate with a mixture that includes at least one polyisobutylene macrodiol, and/or diamine and at least one polyether macrodiol to form a prepolymer having terminally reactive diisocyanate groups; and (b) reacting the prepolymer with a chain extender to yield a polyurethane elastomeric polymer. Preferably, the elastomeric polymer includes (i) a hard segment in the amount of 10% to 60% by weight of the elastomeric polymer, wherein the hard segment includes a urethane, urea or urethaneurea; and (ii) a soft segment in the amount of 40% to 90% by weight of the elastomeric polymer. Preferably, the soft segment includes at least 2% by weight of the soft segment of the at least one polyether macrodiol and/or at least one polycarbonate macrodiol, and at least 2% by weight of the soft segment of the at least one polyisobutylene macrodiol, and/or diamine.

Any one or more of the isocyanates, polyols, chain extenders, or various additives can be employed with the synthetic method of the present invention. For example, polyether macrodiols and/or polyisobutylene macrodiol, described above, as well as any mixture thereof, can be used in the above-described process. Any amounts of the components and their combinations described above can be used.

For example, at least one polyether macrodiol employed by the above-described process is poly(ethylene oxide) diol, polypropylene oxide) diol, poly(trimethylene oxide) diol, poly(tetramethylene oxide) diol, poly(hexamethylene oxide) diol, poly(heptamethylene oxide) diol, poly(octamethylene oxide) diol or poly(decamethylene oxide) diol.

Preferably, at least one polycarbonate macrodiol employed by the above-described process is a poly(alkylene carbonate), as described above.

Examples of the chain extenders that can be employed in the above-described process are 1,4-butanediol; 1,5-pentanediol; 1,6-hexanediol; 1,8-octanediol; 1,9-nonanediol; 1,10-decanediol, 1,12-dodecanediol; 1,4-cyclohexane dimethanol; p-xyleneglycol and 1,4-bis(2-hydroxyethoxy)benzene. Other examples include diamine chain extenders

EXEMPLIFICATION

Materials

Sn(Oct)$_2$ (stannous octoate, Polyscience), 4,4'-methylenebis(phenyl-isocyanate) (MDI, Aldrich, 98%), toluene (Aldrich, 99%), chloroform (Aldrich, at least 99.8%), 1,4-butanediol (BDO, Aldrich, 99%), Phthalimide, potassium (Aldrich, 98%), LiBr (Lithium bromide ReagentPlus®, Aldrich, at least 99%), KOH (potassium hydroxide, Aldrich), Na$_2$SO$_4$ (sodium sulfate, Aldrich), Trifluoroacetic acid (TFA, Aldrich), Tetra-n-butylammonium bromide (TBAB, Alfa Aesar, at least 98%) and Poly(tetramethylene oxide) (PTMO, TERATHANE® 1000 polyether glycol, Aldrich) were used as received. Tetrahydrofuran (THF) or toluene were refluxed over sodium metal and benzophenone over night and distilled under nitrogen atmosphere prior to use. Hexanes were purified by refluxing over sulfuric acid for 24 hours. They were washed with aqueous solution of KOH three times followed by distilled water. Then they were stored over sodium sulfate over night at room temperature. Finally they were distilled over CaH$_2$ under nitrogen atmosphere before use.

Measurements

Molecular weights were measured with a Waters HPLC system equipped with a model 510 HPLC pump, model 410 differential refractometer, model 441 absorbance detector, on-line multiangle laser light scattering (MALLS) detector (MiniDawn, Wyatt Technology Inc.), Model 712 sample processor, and five Ultrastyragel GPC columns connected in the following series: 500, $10^3$, $10^4$, $10^5$, and 100A. THF:TBAB (98:2, wt %) was used as a carrier solvent with a flow rate of 1 mL/min. Static tensile properties (Young's modulus, ultimate tensile strength, referred herein as "UTS", elongation) were measured at room temperature (25° C.) and atmospheric conditions with a 50 N load cell on an Instron Model 4400R at 50 mm/min extension rate. All tests were carried out according to ASTM D412. Samples were cut into dog-bone shape using an ASTM die. All samples were kept at room temperature and atmospheric conditions prior to testing. The polymers were compression molded at 160° C. for 10 min using 17000 psi.

Example 1

Preparation of Ho-allyl-Polyisobutylene(PIB)-allyl-OH

The synthesis of HO-Allyl-PIB-Allyl-OH was carried out by heating the THF solution of bromoallyl telechelic PIB with aqueous solution of KOH at 130° C. for 3 hours.

For example, Br-Allyl-PIB-Allyl-Br ($M_n$=2200, 50 g, 0.023 mol) was dissolved in dry THF (1 liter) and a solution of KOH (50 g, 0.9 mol) in distilled water (500 mL) was added to it. The mixture was heated for 3 hour at 130° C. in a reactor. The reaction was cooled to room temperature. The THF was evaporated using a rotary evaporator. Distilled methanol (500 mL) was added and the precipitate was allowed to settle down. The precipitate was further dissolved in hexanes (200 mL) and slowly added to methanol (600 mL). The sticky mass was allowed to settle down. The process was repeated two times and the purified polymer was finally dried under vacuum at room temperature for 24 hour. Yield: 99%, GPC-MALLS: $M_n$=2400, polydispersity index (PDI)=1.16.

Representative molecular weight data for the hydroxy telechelic PIBs are described in Table 1, below.

TABLE 1

Molecular weight data of the hydroxyallyl telechelic PIBs

| Polymer | $M_n$ (NMR) | $M_n$ (GPC) | PDI |
|---|---|---|---|
| 1 | 4200 | 4300 | 1.10 |
| 2 | 2200 | 2400 | 1.16 |
| 3 | 1500 | 1600 | 1.17 |

Example 2

Syntheses of Polyisobutylene-Based Thermoplastic Polyurethane (PIB-TPU)

As used in Example 2, the terms "one-step procedure" and "two-step procedure" refer to the synthetic scheme exemplified in FIG. 1.

The syntheses of polyurethanes (PUs) with the ratio of soft segment (SS) to hard segment (HS) 80:20 (wt:wt), i.e. PIB(4200)-TPU (Sample Code PIB-TPU-4321), PIB(2200)-TPU (Sample Code PIB-TPU-2211) and PIB(1500)-TPU (Sample Code PIB-TPU-1514) were carried out in toluene using MDI and BDO as the chain extender in presence of 1 mol % of stannous octoate (relative to MDI) at 80° C. The polymers were obtained by adding MDI as the last reagent (one-step procedure).

One-Step Procedure

For examples, the material PIB-TPU-2211 was synthesized as follows. HO-Allyl-PIB-Allyl-OH ($M_n$=2200, 5.2 g, 2.36 mmol) and BDO (212 mg, 2.36 mmol) were azeotropically distilled from dry toluene (10 mL). The mixture was kept at 45° C. for 3 hours under vacuum. 25 mL of dry toluene was added to this mixture, followed by $Sn(Oct)_2$ (20 mg, 0.05 mmol) in toluene. The mixture was heated at 80° C. under a slow stream of dry nitrogen gas. MDI (1.24 g, 4.96 mmol) was added to this mixture and the mixture was stirred vigorously for 6 hours. The mixture was cooled to room temperature, poured into a Teflon® mold and the solvent was evaporated at room temperature in air for 48 hours. Finally the polymer was dried under vacuum at 50° C. for 12 hours. Representative molar ratio of the reactants and Shore hardness of the TPUs are described in Table 2.

TABLE 2

Molar ratio of reactants and Shore hardness of PIB TPU

| Code | HO-Allyl-PIB-Allyl-OH ($M_n$)[1] | MDI/BDO/PIB (molar ratio) | Wt % SS:HS | Shore hardness (A) |
|---|---|---|---|---|
| PIB-TPU-4321 | 4200 | 3/2/1 | 81:19 | 60 |
| PIB-TPU-2211 | 2200 | 2/1/1 | 79:21 | 59 |
| PIB-TPU-1514 | 1500 | 5/1/4 | 80:20 | 62 |

[1]$M_n$ of precursor HO-Allyl-PIB-Allyl-OH

The $M_n$ of PIB-TPU-2211 after various polymerization times is noted in Table 3. The increase in $M_n$ was observed till 6 hour time. The polyurethane was then cured for one week at room temperature. A further increase in $M_n$=105000, PDI=2.4 was observed for the cured sample.

TABLE 3

Polymerization time and corresponding $M_n$ data

| Polymerization time (h) | $M_n$ (GPC) | PDI (GPC) |
|---|---|---|
| 0[1] | 2200 | 1.16 |
| 0.5 | 23000 | 1.8 |
| 0.7 | 32000 | 1.8 |
| 3 | 66000 | 2.0 |
| 6 | 87000 | 2.2 |
| 168 | 105000 | 2.4 |

[1]$M_n$ of precursor HO-Allyl-PIB-Allyl-OH

The $M_n$ of PIB-TPUs having Shore hardness of about 60A hardness prepared with polyisobutylenes having different molecular weights are summarized in Table 4. PIB-TPU-1514 was not soluble in THF:TBAB (98:2 wt %), hence the $M_n$ could not be determined.

TABLE 4

GPC data of PIB-TPUs (Shore hardness 60A)

| Code | $M_n$ (GPC) | PDI (GPC) |
|---|---|---|
| PIB-TPU-4321 | 110000 | 2.3 |
| PIB-TPU-2211 | 92000 | 3.1 |
| PIB-TPU-1321 | — | — |

The syntheses of polyurethanes with soft segment (SS) to hard segment (HS) ratio of 60:40 (wt %), e.g. PIB(4200)-TPU (Sample Code PIB-TPU-4761), PIB(2200)-TPU (Sample Code PIB-TPU-2431) and PIB(1500)-TPU (Sample Code PIB-TPU-1321) were carried out by a one-step synthetic procedure (see FIG. 1) in toluene using MDI and BDO as the chain extender and 1 mol % of stannous octoate (relative to MDI) as catalyst at 80° C.

For example, PIB-TPU-2431 was synthesized as follows. HO-Allyl-PIB-Allyl-OH ($M_n$=2200, 5.2 g, 2.36 mmol) and BDO (637 mg, 7.08 mmol) were azeotropically distilled from dry toluene (10 mL). The mixture was kept at 45° C. for 3 hours under vacuum. 25 mL of dry toluene was added to this mixture, followed by Sn(Oct)$_2$ (38 mg, 0.09 mmol) in toluene. The mixture was heated at 80° C. under a slow stream of dry nitrogen gas. MDI (2.36 g, 9.44 mmol) was added to the mixture and the mixture was stirred vigorously for 6 hours. The mixture was cooled to room temperature, poured in a Teflon® mold and the solvent was evaporated at room temperature in air for 48 hours. Finally the polymer was dried under vacuum at 50° C. for 12 hours.

Representative molar ratio of the reactants and Shore hardness of the TPUs are described in Table 5, below.

TABLE 5

Molar ratio of reactants and Shore hardness of PIB TPU

| Code | HO-Allyl-PIB-Allyl-OH ($M_n$) | MDI/BDO/PIB (molar ratio) | Wt % SS:HS | Shore hardness (A) |
|---|---|---|---|---|
| PIB-TPU-4761 | 4200 | 7/6/1 | 62:38 | 81 |
| PIB-TPU-2431 | 2200 | 4/3/1 | 60:40 | 79 |
| PIB-TPU-1321 | 1500 | 3/2/1 | 59:41 | 83 |

The GPC analysis of the TPUs were carried out in THF: TBAB (98:2 wt %). The molecular weight values (Table 6) were obtained in the range of 83000-91000 with PDI in the range of 1.8-2.2.

TABLE 6

GPC data of PIB-TPUs (Shore hardness 80A)

| Code | $M_n$ (GPC) | PDI (GPC) |
|---|---|---|
| PIB-TPU-4761 | 87000 | 2.0 |
| PIB-TPU-2431 | 91000 | 2.2 |
| PIB-TPU-1321 | 83000 | 1.8 |

Representative mechanical property data of the PIB-TPUs are listed in Table 7. The UTS was obtained in the range of 6-9 MPa with elongation at break in the range of 40-400%. With an increase in the hard segment to soft segment ratio, the Young's modulus increased and the elongation at break decreased. The thermal processing of TPUs with higher Shore hardness was difficult compared to the softer ones. PIB-TPU-2431 and PIB-TPU-1321 could not be molded into flat sheets for testing, so the tensile properties were not recorded.

TABLE 7

Mechanical property data of PIB-TPUs

| Polymer | Shore (A) | Young's Modulus (MPa) | Tensile Strength (MPa) | Elongation (%) |
|---|---|---|---|---|
| PIB-TPU-4321 | 60 | 6 | 7 | 200-250 |
| PIB-TPU-4761 | 81 | 40 | 6 | 30-40 |
| PIB-TPU-2211 | 59 | 5 | 9 | 300-400 |
| PIB-TPU-2431 | — | — | — | — |
| PIB-TPU-1514 | 62 | 5 | 6 | 100-150 |
| PIB-TPU-1321 | — | — | — | — |

Changing the catalyst of polymerization from tin octoate to 1,3-Diacetoxy-1,1,3,3-tetrabutyldistannoxane (DTDS) the UTS of PIB-TPU-2211 increased from 9 MPa to 12 MPa and the elongation at break decreased to 100% from 350% as shown in Table 8.

TABLE 8

Mechanical property data of the PIB TPUs

| Polymer | Shore A | Young's Modulus (MPa) | Tensile Strength (MPa) | Elongation (%) |
|---|---|---|---|---|
| PIB-TPU-2211 Sn(Oct)$_2$ | 59 | 5 | 9 | 300-400 |
| PIB-TPU-2211† DTDS | 60 | 24 | 12 | 100 |
| PIB-TPU-2431 Sn(Oct)$_2$ | — | — | — | — |
| PIB-TPU-2431† DTDS | 80 | 72 | 15 | 30-40 |

†not soluble in THF/TBAB, soluble in chloroform/TFA

Two-Step Synthesis

In subsequent experiments, the technique for the polyurethane synthesis was modified by adding 1,4-butanediol (BDO) as the last reagent. The process consisted of two steps. (See FIG. 1.) In the first step, HO-Allyl-PIB-Allyl-OH was mixed with excess of MDI to form the intermediate PUs. In the subsequent step these intermediate polyurethanes were chain-extended with 1,4-butanediol to obtain the high molecular weight TPUs. A representative procedure is given below.

The PIB-TPU-4321 was synthesized using the two-step procedure by adding BDO last. HO-Allyl-PIB-Allyl-OH ($M_n$=4200, 5.2 g, 1.24 mmol) was azeotropically distilled from dry toluene (10 mL). The polymer was kept at 45° C. for 3 hours under vacuum. 25 mL of dry toluene was added to this mixture, followed by Sn(Oct)$_2$ (15 mg, 0.037 mmol) in toluene. The mixture was heated at 80° C. under a slow stream of dry nitrogen gas. To it MDI (930 mg, 3.72 mmol) was added and the mixture was stirred vigorously for 30 min. BDO (223 mg, 2.48 mmol) was added to this mixture and stirring continued for 4 hours. The mixture was cooled to room temperature, poured in a Teflon® mold and the solvent was evaporated at room temperature in air for 48 hours. Finally the polymer was dried under vacuum at 50° C. for 12 hours.

As can be seen in Table 9, a higher molecular weight with narrow molecular weight distribution was observed for the polymer obtained by two-step synthesis compared to the polymer synthesized by one-step procedure. The tensile properties were similar in both the cases. The processing was easier, compared to the same TPU synthesized by the one-step procedure.

TABLE 9

$M_n$ and tensile property data of PIB-TPU-4321 synthesized under different conditions

| Procedure | $M_n$ (GPC) | PDI (GPC) | UTS (MPa) | Elongation at break (%) |
|---|---|---|---|---|
| One-step | 110000 | 2.3 | 7 | 200 |
| Two-step | 119000 | 1.6 | 7 | 150 |

Example 3

Synthesis of Polyisobutylene/Polyether-Based Thermoplastic Urethane (PIB-PTMO-TPU)

Figure 2:
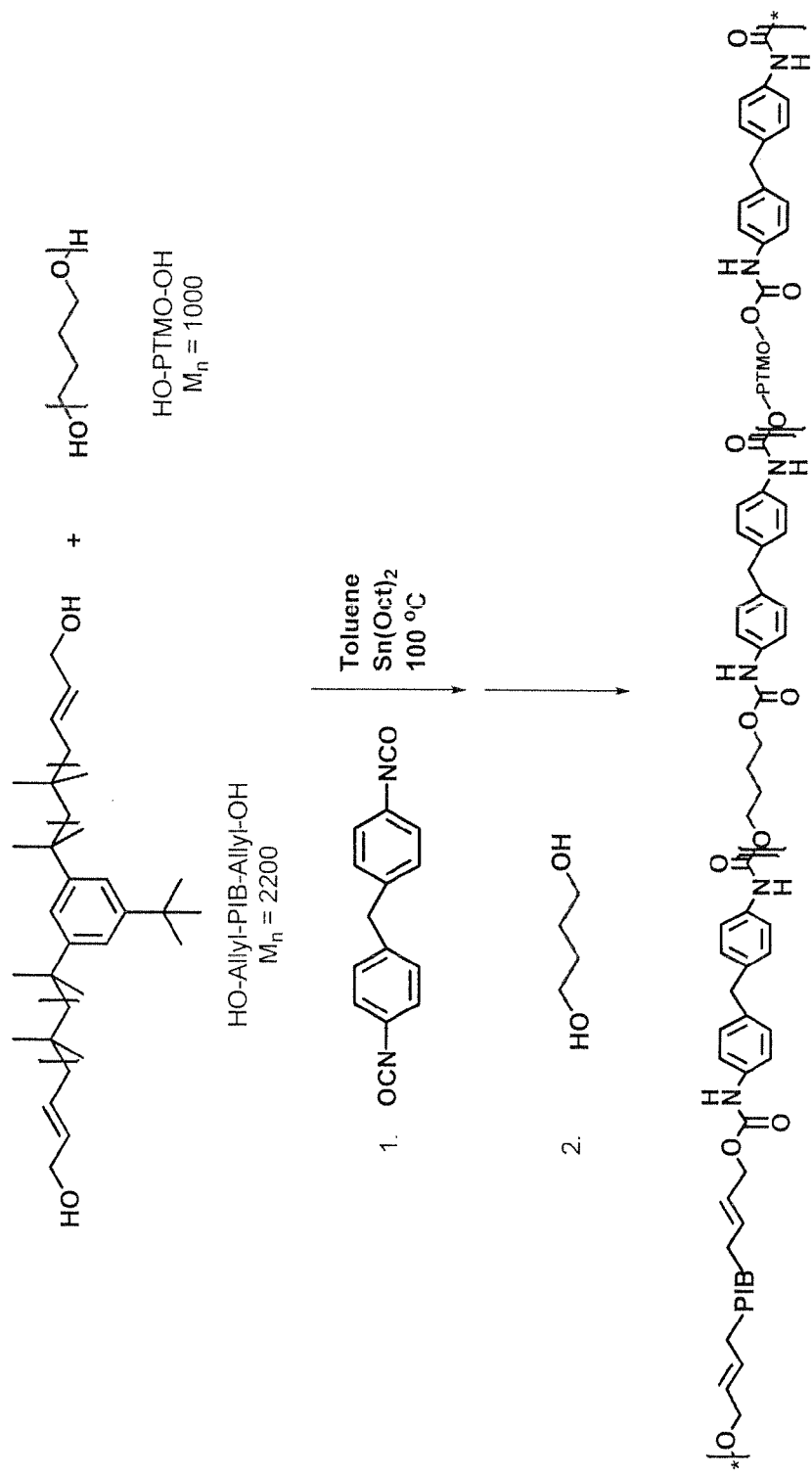
FIG. 2 is a schematic diagram of an example of a synthetic procedure employed to produce the polyisobutylene/polyether-containing thermal polyurethanes of the present invention.

TPUs having mixtures of PIB and PTMO in different proportions as soft segment were synthesized using the two-step procedure according to the synthetic procedure exemplified in FIG. 2. BDO and MDI constituted the hard segment. The soft segment to hard segment ratio of 80:20 wt % was maintained in all the cases.

For example, PIB-PTMO-82-6 was synthesized as follows. HO-Allyl-PIB-Allyl-OH ($M_n$=2200, 5.2 g, 2.36 mmol) and PTMO ($M_n$=1000, 1.3 g, 1.3 mmol) were azeotropically distilled from dry toluene (10 mL). The mixture was kept at 45° C. for 3 hours under vacuum. 25 mL of dry toluene was added to this mixture, followed by $Sn(Oct)_2$ (28.3 mg, 0.07 mmol) in toluene. The mixture was heated at 80° C. under a slow stream of dry nitrogen gas. MDI (1.76 g, 7.02 mmol) was added to this mixture and the mixture was stirred vigorously for 30 min. BDO (302 mg, 3.36 mmol) was added to the resulting reaction mixture and the mixture was stirred for 4 hours at 100° C. The mixture was cooled to room temperature, poured in a Teflon® mold and the solvent was evaporated at room temperature in air for 48 hours. Finally the polymer was dried under vacuum at 50° C. for 12 hours.

The sample codes and weight percent values of PIB and PTMO is shown in Table 10.

TABLE 10

Weight Percent Values of PIB and PTMO in PIB-PTMO TPU (Shore hardness 60A)

| Code | HO-PIB-OH[1] (wt %)[3] | HO-PTMO-OH[2] (wt %)[3] |
| --- | --- | --- |
| PIB-PTMO-91-6 | 90 | 10 |
| PIB-PTMO-82-6 | 80 | 20 |
| PIB-PTMO-73-6 | 70 | 30 |
| PIB-PTMO-64-6 | 60 | 40 |
| PIB-PTMO-55-6 | 50 | 50 |
| PIB-PTMO-28-6 | 20 | 80 |
| PTMO-60A | 0 | 100 |

[1]HO-PIB-OH, $M_n$ = 2200,
[2]HO-PTMO-OH, $M_n$ = 1000,
[3]soft:hard = 79:21 wt %

GPC-RI traces of the TPUs showed monomodal distribution of molecular weight with the values of molecular weight in the range of 55000-140000 and PDI of approximately 1.4-2.7. The molecular weight data of the TPUs synthesized according to the method described above are described in Table 11:

TABLE 11

Molecular weight data of PIB-PTMO TPU (Shore hardness ≈ 60A)

| Code | $M_n$ (GPC) | PDI |
| --- | --- | --- |
| PIB-PTMO-91-6 | 94000 | 2.1 |
| PIB-PTMO-82-6 | 129000 | 2.2 |
| PIB-PTMO-73-6 | 137000 | 2.7 |
| PIB-PTMO-64-6 | 95000 | 2.2 |
| PIB-PTMO-55-6 | 85000 | 1.4 |
| PIB-PTMO-28-6 | 55000 | 1.6 |
| PTMO-60A | 33000 | 1.3 |

The ultimate tensile strength (UTS) of the PIB-PTMO TPUs was approximately 4-20 MPa with elongation at break in the range of 400-740%. The Young's moduli of the polymers were obtained in the range of 2-9 MPa. The Shore hardness and tensile property data of the TPUs are listed in Table 12 below:

TABLE 12

Shore hardness and tensile property data of PIB-PTMO TPU

| Polymer | PTMO (wt %) | Shore A | Young's Modulus (MPa) | Tensile Strength (MPa) | Elongation (%) |
| --- | --- | --- | --- | --- | --- |
| PIB-PTMO-91-6 | 10 | 71 | 8.5 | 20 | 400 |
| PIB-PTMO-82-6 | 20 | 60 | 5.2 | 18 | 680 |
| PIB-PTMO-73-6 | 30 | 61 | 4.5 | 18 | 740 |
| PIB-PTMO-64-6 | 40 | 59 | 4.7 | 22 | 740 |
| PIB-PTMO-55-6 | 50 | 62 | 7.5 | 22 | 730 |
| PIB-PTMO-28-6 | 80 | 61 | 2 | 4 | 400 |
| PTMO-60A | 100 | 60 | 5 | 10 | 500 |

With addition of a small amount of polytetramethyleneoxide diol (PTMO), the mechanical properties of the polymers increased dramatically. However, the properties remained similar with further increase in PTMO composition. TPU with 100% PTMO (PTMO-60A) also exhibited similar tensile property.

PIB-PTMO TPUs with higher hard segment to soft segment ratio were synthesized using the two-step procedure described above. The soft segment to hard segment ratio (SS:HS) of 65:35 percent by weight was maintained in all the cases, while the PIB to PTMO ratio (in percent by weight of the soft segment) was varied. Results are presented in Table 13.

TABLE 13

Percent Weight of PIB and PTMO in PIB-PTMO TPU (Shore hardness 80A)

| Code | HO-PIB-OH[1] (wt %)[3] | HO-PTMO-OH[2] (wt %)[3] |
| --- | --- | --- |
| PIB-PTMO-91-8 | 90 | 10 |
| PIB-PTMO-82-8 | 80 | 20 |
| PIB-PTMO-73-8 | 70 | 30 |
| PIB-PTMO-64-8 | 60 | 40 |
| PIB-PTMO-28-8 | 20 | 80 |
| PTMO-80A | 0 | 100 |

[1]HO-PIB-OH, $M_n$ = 2200,
[2]HO-PTMO-OH, $M_n$ = 1000,
[3]SS:HS = 65:35 wt %

Exemplary Synthesis of a PIB-PTMO-TPU

PIB-PTMO-82-8 was synthesized as follows. HO-Allyl-PIB-Allyl-OH $M_n$=2200, 5.2 g, 2.36 mmol) and PTMO ($M_n$=1000, 1.3 g, 1.3 mmol) were azeotropically distilled from dry toluene (10 mL). The mixture was kept at 45° C. for 3 hours under vacuum. 25 mL of dry toluene was added to this mixture, followed by $Sn(Oct)_2$ (42 mg, 0.104 mmol) in toluene. The mixture was heated at 80° C. under a slow stream of dry nitrogen gas. MDI (2.6 g, 10.38 mmol) was added to the reaction mixture, and the mixture was stirred vigorously for 30 min. BDO (605 mg, 6.72 mmol) was added to the reaction mixture, and the mixture was stirred for 4 hours at 100° C. The mixture was cooled to room temperature, poured in a Teflon® mold and the solvent was evaporated at room temperature in air for 48 hours. Finally the polymer was dried under vacuum at 50° C. for 12 hours.

Molecular weight data of PIB-PTMO TPUs with Shore hardness of 80A is shown in Table 14. The molecular weight of the polymers is in the range of 42000-138000, with PDI of 1.9-3.8.

TABLE 14

Molecular weight data of PIB-PTMO TPU (Shore hardness 80A)

| Code | $M_n$ (GPC) | PDI |
|---|---|---|
| PIB-PTMO-91-8 | 84000 | 1.9 |
| PIB-PTMO-82-8 | 119000 | 2.8 |
| PIB-PTMO-73-8 | 138000 | 3.5 |
| PIB-PTMO-64-8 | 130000 | 3.7 |
| PIB-PTMO-28-8 | 40000 | 3.8 |
| PTMO-80A | 42000 | 2.4 |

The ultimate tensile strength (UTS) of the PIB-PTMO TPUs (Shore hardness 80A) were in the range of 18-25 MPa with elongation at break in the range of 150-550%. The Young's modulus of the polymers were higher compared to PIB-PTMO TPUs with lower Shore hardness (60A) and varied between 11-32 MPa. Increase in PTMO concentration linearly increased the UTS as well as the elongation at break of the TPUs. The PIB-PTMO TPU comprising PTMO-80A exhibited highest UTS and elongation at break. The Shore hardness and tensile property data of the TPUs are listed in Table 15 below.

TABLE 15

Shore hardness and tensile property data of PIB-PTMO TPU (Shore hardness 80A)

| Polymer | Shore A | Young's Modulus (MPa) | Tensile Strength (MPa) | Elongation (%) | Tear Strength (pli) |
|---|---|---|---|---|---|
| PIB-PTMO-91-8 | 83 | 32 | 18 | 150 | 310 |
| PIB-PTMO-82-8 | 82 | 32 | 23 | 400 | 380 |
| PIB-PTMO-73-8 | 81 | 23 | 27 | 370 | 409 |
| PIB-PTMO-64-8 | 81 | 11 | 25 | 550 | 440 |
| PIB-PTMO-28-8 | 81 | 5 | 8 | 550 | 270 |

Exemplary Synthesis of the PIB-PTMO TPU Performed at 120° C.

PIB-PTMO TPUs having not less than 80 percent by weight of the soft segment of the PTMO component were synthesized according to the synthetic scheme exemplified in FIG. 2. The soft segment to hard segment ratio (SS:HS) was varied to achieve Shore hardness values of 60A to 80A.

For example, PIB-PTMO-28-8 was synthesized as follows. HO-Allyl-PIB-Allyl-OH ($M_n$=2200, 1.12 g, 0.51 mmol) and PTMO ($M_n$=1000, 4.48 g, 4.48 mmol) were azeotropically distilled from dry toluene (10 mL). The mixture was kept at 45° C. for 3 hours under vacuum. 25 mL of dry toluene was added to the reaction mixture, followed by Sn(Oct)$_2$ (44.6 mg, 0.11 mmol) in toluene. The mixture was heated at 80° C. under a slow stream of dry nitrogen gas. MDI (2.67 g, 10.7 mmol) was added to the reaction mixture, and the mixture was stirred vigorously for 30 min. BDO (520 mg, 5.7 mmol) was added to the reaction mixture, and the temperature was raised to 120° C. After 15 minutes, the temperature was decreased to 100° C. and the mixture was kept under nitrogen for 4 hours. The mixture was cooled to room temperature, poured in a Teflon® mold and the solvent was evaporated at room temperature in air for 48 hours. Finally the polymer was dried under vacuum at 50° C. for 12 hours.

The GPC data of the TPUs having PTMO in excess of 80% by weight of the soft segment is given in Table 16 below. The molecular weight values of these TPUs increased compared to the polymers that were synthesized from the same starting materials, but at a temperature of 100° C. (Table 11 and 14).

TABLE 16

Molecular Weight Data of PIB-PTMO TPU, Soft Segment Including not Less than 80% by Weight of PTMO (Reaction Temperature = 120° C.)

| Code | $M_n$ (GPC) | PDI |
|---|---|---|
| PIB-PTMO-28-6 | 105000 | 2.3 |
| PTMO-60A | 113000 | 2.0 |
| PIB-PTMO-28-8 | 87000 | 1.8 |
| PTMO-80A | 102000 | 1.7 |

The UTS, ultimate elongation at break and Young's modulus data of the TPUs of Table 16 are listed in Table 17 below. The UTS of PTMO-60A (compare to Table 12) increased from 10 MPa to 20 MPa when the synthetic procedure was modified by increasing the reaction temperature to 120° C. A 200% enhancement in ultimate elongation at break was also observed. Other TPUs also exhibited improved tensile properties, as shown in Table 17. The tensile data of the PIB-PTMO-28-6 (see Table 12) and PIB-PTMO-28-8 (see Table 15) synthesized at 100° C. are described previously.

TABLE 17

The Tensile Property of PIB-PTMO TPU, Soft Segment Including not Less than 80% by Weight of PTMO (Reaction Temperature = 120° C.)

| Code | Shore A | UTS (MPa) | Elongation at break (%) | Young's Modulus (MPa) |
|---|---|---|---|---|
| PIB-PTMO-28-6 | 60 | 22 | 950 | 7 |
| PTMO-60A | 60 | 20 | 700 | 5 |
| PIB-PTMO-28-8 | 81 | 17 | 740 | 9 |
| PTMO-80A | 80 | 35 | 800 | 7 |

Synthesis of PIB-PTMO-TPU (Shore Hardness About 95A)

PIB-PTMO TPUs with designed Shore hardness of about 95A were synthesized using the two-step procedure described above. The soft segment to hard segment ratio (SS:HS) of 60:40 w:w was maintained in all the cases, while the PIB to PTMO weight ratio was varied as shown in Table 18.

TABLE 18

Percent Weight of PIB and PTMO in PIB-PTMO TPU (Shore hardness 95A)

| Code | HO-PIB-OH[1] (wt %)[3] | HO-PTMO-OH[2] (wt %)[3] |
|---|---|---|
| PIB-PTMO-91-9 | 90 | 10 |
| PIB-PTMO-82-9 | 80 | 20 |
| PIB-PTMO-73-9 | 70 | 30 |

TABLE 18-continued

Percent Weight of PIB and PTMO in PIB-PTMO TPU
(Shore hardness 95A)

| Code | HO-PIB-OH[1] (wt %)[3] | HO-PTMO-OH[2] (wt %)[3] |
|---|---|---|
| PIB-PTMO-64-9 | 60 | 40 |
| PIB-PTMO-55-9 | 50 | 50 |

[1]HO-PIB-OH, $M_n$ = 2200,
[2]HO-PTMO-OH, $M_n$ = 1000,
[3]SS:HS = 60:40 wt %

For example, PIB-PTMO-73-9 was synthesized as follows. HO-Allyl-PIB-Allyl-OH ($M_n$=2200, 3.92 g, 1.78 mmol) and PTMO ($M_n$=1000, 1.68 g, 1.68 mmol) were azeotropically distilled from dry toluene (10 mL). The mixture was kept at 45° C. for 3 hours under vacuum. 25 mL of dry toluene was added to the reaction mixture, followed by Sn(Oct)$_2$ (49 mg, 0.121 mmol) in toluene. The mixture was heated at 80° C. under a slow stream of dry nitrogen gas. MDI (3.03 g, 12.12 mmol) was added to the reaction mixture, and the mixture was stirred vigorously for 30 min. BDO (780 mg, 8.66 mmol) was added to the reaction mixture, and the mixture was stirred for 4 hours at 100° C. The mixture was cooled to room temperature, poured in a Teflon® mold and the solvent was evaporated at room temperature in air for 48 hours. Finally, the polymer was dried under vacuum at 50° C. for 12 hours.

The molecular weight data of PIB-PTMO TPUs with Shore 95A hardness shown in Table 19. The molecular weight of the polymers was in the range of 79000-111500, with PDI of 1.6-3.4.

TABLE 19

Molecular weight data of PIB-PTMO TPU (Shore hardness 95A)

| Code | Mn (GPC) | PDI (GPC) |
|---|---|---|
| PIB-PTMO-91-9* | — | — |
| PIB-PTMO-82-9 | 87000 | 3.4 |
| PIB-PTMO-73-9 | 79000 | 1.6 |
| PIB-PTMO-64-9 | 105000 | 2.5 |
| PIB-PTMO-55-9 | 111500 | 2.8 |

*The TPU is sparingly soluble in THF/TBAB mixture

The UTS, Shore hardness, tear strength and Young's modulus data for PIB-PTMO-TPU (Shore hardness of about 95A) are presented in Table 20. The UTS and Young's modulus of the polymers were observed in the range of 14-42 MPa and 144-17 MPa respectively. The elongation at break was observed in the range of 30-510%. The UTS and Young's modulus of PIB-PTMO-73-9 was higher compared to the TPUs having same PIB/PTMO ratio of 70/30 by weight, such as PIB-PTMO-6 and PIB-PTMO-8 TPUs with Shore hardness 60A (PIB-PTMO-73-6) and 80A (PIB-PTMO-73-8).

TABLE 20

Tensile properties of PIB-PTMO-TPU (Shore hardness ≈ 95A)

| Code | Shore A | UTS (MPa) | Young's Modulus (MPa) | Elongation at break (%) |
|---|---|---|---|---|
| PIB-PTMO-91-9 | 95 | 14 | 144 | 30 |
| PIB-PTMO-82-9 | 98 | 29 | 50 | 310 |
| PIB-PTMO-73-9 | 99 | 40 | 45 | 350 |
| PIB-PTMO-64-9 | 98 | 39 | 27 | 430 |
| PIB-PTMO-55-9 | 96 | 42 | 17 | 510 |

Example 4

Synthesis of Polyisobutylene/Poly(alkylenecarbonate)-Based Thermoplastic Urethane (PIB-PHMC-TPU)

TPU, having a mixture of PIB and poly(hexamethylene carbonate) (PHMC) in the ratio of 70:30 percent by weight of the soft segment was synthesized using the procedure similar to the one illustrated in FIG. 2. The hard segment comprised BDO and MDI. The ratio of hard segment to soft segment, HS:SS, was 21:79 percent by weight.

A synthetic procedure for PIB-PHMC-73-6 is given below. PIB-PHMC-73-6 was synthesized as follows. HO-Allyl-PIB-Allyl-OH ($M_n$=2200, 4.5 g, 2.04 mmol) and PHMC ($M_n$=860, 1.93 g, 2.27 mmol) were azeotropically distilled from dry toluene (10 mL). The reaction mixture was kept at 45° C. for 3 hours under vacuum. 25 mL of dry toluene was added to the reaction mixture, followed by Sn(Oct)$_2$ (26.3 mg, 0.065 mmol) in toluene. The reaction mixture was heated at 80° C. under a slow stream of dry nitrogen gas. MDI (1.63 g, 6.51 mmol) was added to the reaction mixture and the mixture was stirred vigorously for 30 minutes. BDO (200 mg, 2.2 mmol) was added to the reaction mixture and the mixture was stirred for 4 hours at 100° C. The reaction mixture was cooled to room temperature, poured in a Teflon® mold, and the solvent was evaporated at room temperature in air for 48 hours. Finally, the polymer was dried under vacuum at 50° C. for 12 hours.

The ultimate tensile strength (UTS) of the PIB-PHMC-73-6 was 10 MPa with elongation at break of about 300%. The Young's modulus of the polymer was 10 MPa with Shore (A) hardness about 61 A.

Example 5

Preparation of an Elastomeric Polymer Comprising Polyisobutylene-diamine

The synthesis of $H_2N$-Allyl-PIB-Allyl-$NH_2$ was carried out by heating the THF:DMF (70:30, v:v) solution of chloroallyl telechelic PIB with phthalimide potassium under reflux conditions for 18 hours followed by hydrolysis in presence of $NH_2NH_2.H_2O$.

For example, Phthalimide-Allyl-PIB-Allyl-Phthalimide was synthesized as follows. Cl-Allyl-PIB-Allyl-Cl ($M_n$=2100, 10 g, 0.0048 mol) was dissolved in dry THF (300 mL) and dry DMF (100 mL) followed by the addition of phthalimide potassium (50 g, 0.27 mol) and the mixture was refluxed under dry nitrogen atmosphere for 18 h. The reaction mixture was cooled to room temperature, filtered and THF was evaporated. Methanol was added to the sticky mass left over and the precipitate was separated and dissolved in hexanes. The solution was reprecipitated in methanol. The product obtained was further purified by dissolution and reprecipitation using hexanes and methanol.

A typical synthetic procedure for $H_2N$-Allyl-PIB-Allyl-$NH_2$ is as follows. Phthalimide-Allyl-PIB-Allyl-Phthalimide (9 g, 0.0042 mol) was dissolved in THF (200 mL) and hydrazine hydrate (15 g) was added. The mixture was refluxed for 24 h. The reaction was stopped and cooled to room temperature. A solution of KOH (10 g, in 25 mL of water) was added and stirred for 30 min. THF was evaporated under reduced pressure and methanol was added. The precipitate obtained was purified by dissolving in hexanes and reprecipitating in methanol. Yield: 98%, NMR: $M_n$=2100.

Example 6

Synthesis of Polyisobutylene/Poly(tetramethylene Oxide)-Based Thermoplastic Urethaneurea (PIB-PTMO-TPUU)

Figure 3:
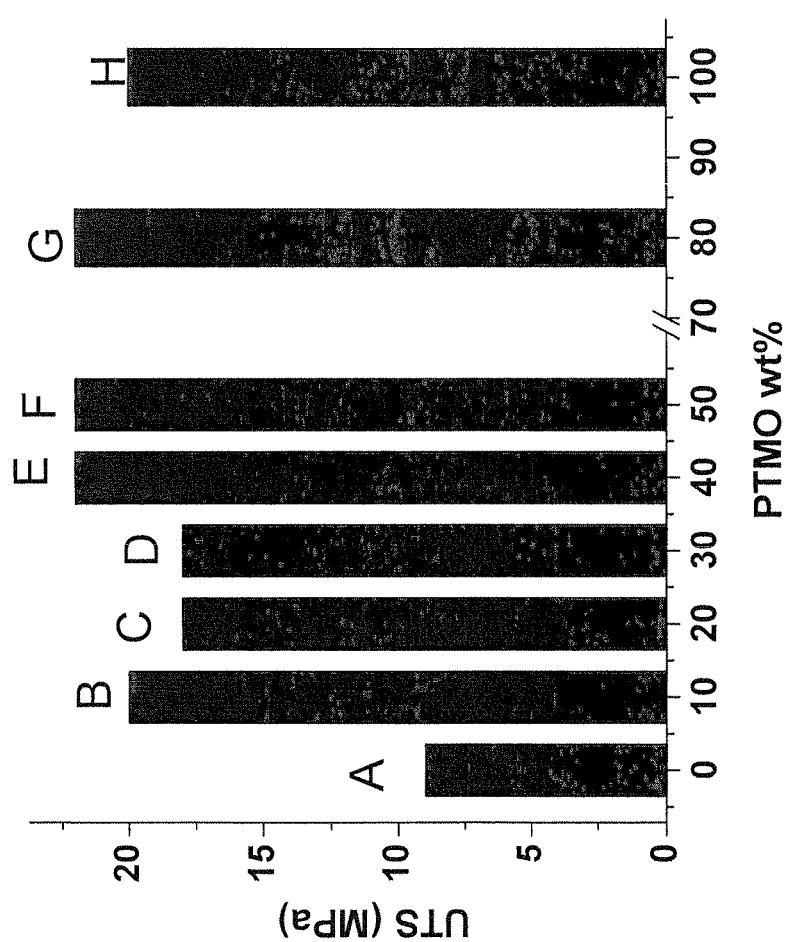
FIG. 3 is a bar plot showing the ultimate tensile strength (UTS) values of eight sample thermal polyurethane polymers of the present invention.
Figure 5:
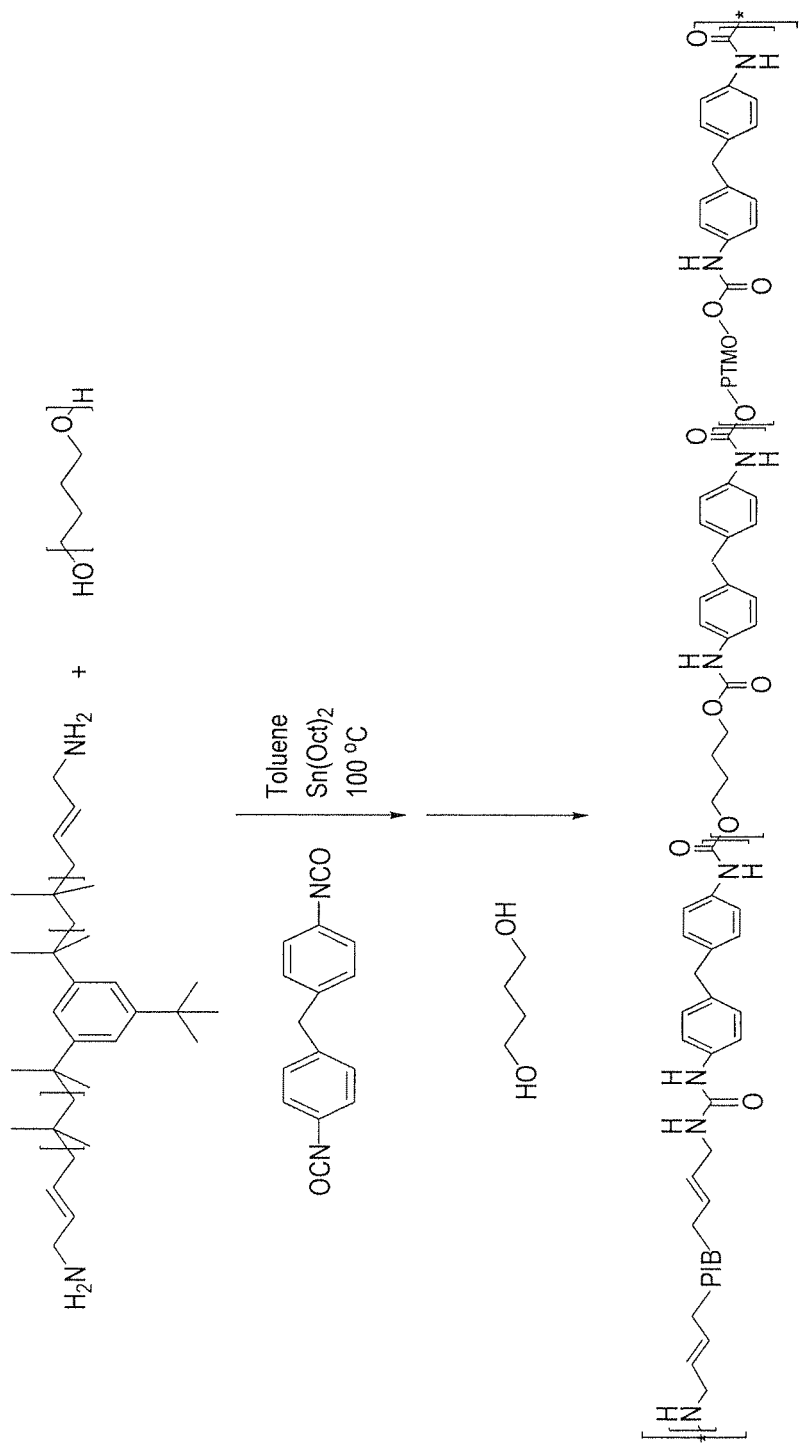
FIG. 5 is a schematic diagram of an example of a synthetic procedure employed by the present invention to produce polyurethaneureas based on PIB and PTMO segment.

A series of PIB based polyurethaneurea with designed Shore 80A hardness was synthesized by chain extension of $H_2N$-Allyl-PIB-Allyl-$NH_2$ and HO-PTMO-OH with BDO and MDI as exemplified in FIG. 3. The ratio of PIB:PTMO was varied and the SS:HS w:w ratio was maintained at 65:35 as shown in Table 21. The synthetic route is is schematically depicted in FIG. 5.

TABLE 21

Percent Weight of PIB and PTMO in PIB-PTMO TPUU (Shore hardness 80A)

| Code | $H_2N$-PIB-$NH_2$[1] (wt % in SS) | HO-PTMO-OH[2] (wt % in SS) | PTMO (wt % in TPUU) |
|---|---|---|---|
| PIB-TPUU-82-8 | 80 | 20 | 13 |
| PIB-TPUU-73-8 | 70 | 30 | 19 |
| PIB-TPUU-64-8 | 60 | 40 | 26 |
| PIB-TPUU-19-8 | 10 | 90 | 59 |

[1]$H_2N$-PIB-$NH_2$ ($M_n$) = 2100,
[2]HO-PTMO-OH ($M_n$) = 1000

Exemplary Synthesis of a PIB-PTMO-TPUU

PIB-TPUU-82-8 was synthesized as follows. $H_2N$-Allyl-PIB-Allyl-$NH_2$ $M_n$=2100, 5.2 g, 2.36 mmol) and PTMO ($M_n$=1000, 1.3 g, 1.3 mmol) were azeotropically distilled from dry toluene (10 mL). The mixture was kept at 45° C. for 3 hours under vacuum. 25 mL of dry toluene was added to this mixture, followed by Sn(Oct)$_2$ (42 mg, 0.104 mmol) in toluene. The mixture was heated at 80° C. under a slow stream of dry nitrogen gas. MDI (2.6 g, 10.38 mmol) was added to the reaction mixture, and the mixture was stirred vigorously for 30 min. BDO (605 mg, 6.72 mmol) was added to the reaction mixture and the mixture was stirred for 4 hours at 100° C. The mixture was cooled to room temperature, poured in a Teflon® mold and the solvent was evaporated at room temperature in air for 48 hours. Finally the polymer was dried under vacuum at 50° C. for 12 hours.

Molecular weight data of PIB-PTMO TPUUs with Shore 80A hardness are shown in Table 22. The molecular weight of the polymers is in the range of 98700-119000, with PDI=1.6-2.8.

TABLE 22

Molecular weight data of PIB-PTMO TPUU (Shore hardness 80A)

| Code | $M_n$ (GPC) | PDI (GPC) |
|---|---|---|
| PIB-TPUU-82-8 | 104000 | 1.8 |
| PIB-TPUU-73-8 | 98700 | 2.5 |
| PIB-TPUU-64-8 | 106500 | 2.8 |
| PIB-TPUU-19-8 | 119000 | 1.6 |

The UTS, Shore hardness, tear strength and Young's modulus data for PIB-PTMO-TPUU are presented in Table 23. The UTS of the polymers was observed in the range of 23-32 MPa and the Young's modulus varied between 5 to 50 MPa. The elongation at break was observed in the range of 250-675%.

TABLE 23

Tensile properties of PIB-PTMO-TPUU (Shore hardness ≈ 80A)

| Code | Shore A00 | UTS 00(MPa) | Young's Modulus (MPa) | Elongation at break (%) |
|---|---|---|---|---|
| PIB-TPUU-82-8 | 86 | 23 | 50 | 250 |
| PIB-TPUU-73-8 | 85 | 26 | 30 | 310 |
| PIB-TPUU-64-8 | 89 | 32 | 21 | 420 |
| PIB-TPUU-19-8 | 86 | 29 | 5 | 675 |

Example 4

Mechanical Measurements of Selected Sample TPUs

Ultimate tensile strength (UTS) and elongation at break were measured as described above for eight samples:
A, PIB-TPU-2221 (shown in Table 7),
B, PIB-PTMO-91-6 (shown in Table 12),
C, PIB-PTMO-82-6 (shown in Table 12),
D, PIB-PTMO-73-6 (shown in Table 12),
E, PIB-PTMO-64-6 (shown in Table 12),
F, PIB-PTMO-55-6 (shown in Table 12),
G, PIB-PTMO-28-6 (shown in Table 12), and
H, PTMO-60A (shown in Table 17).

These samples were synthesized according to the procedure described in Example 3, above. The samples differed in the content of PTMO, a polyether diol.

Figure 4:
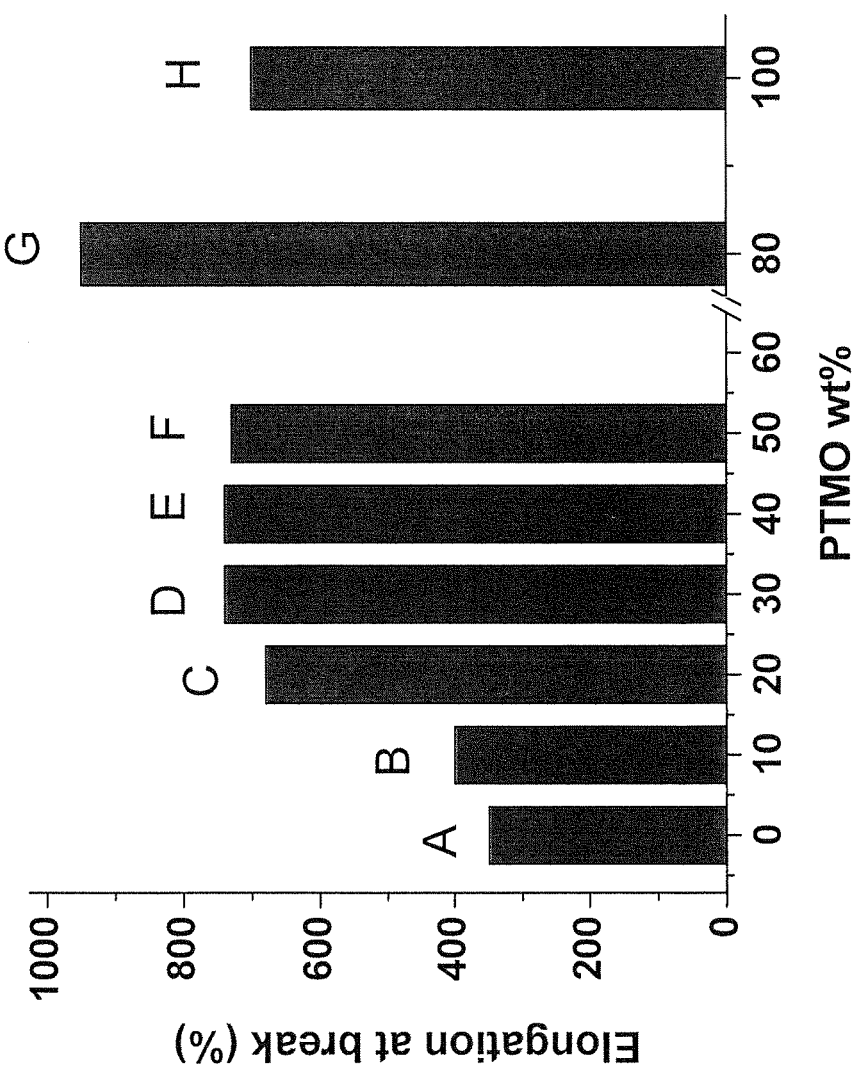
FIG. 4 is a bar plot showing the elongation at break values of eight sample thermal polyurethane polymers of the present invention.

The results are presented in FIG. 3 and FIG. 4. As can be seen, addition of PTMO improves the mechanical properties of a PIB-based TPU, compared with Sample A. Furthermore, comparison with Sample H, which does not contain any PIB shows that the TPUs based on a combination of the PIB macrodiols and polyether macrodiols possess mechanical properties that are superior to the TPUs based on PIB macrodiols or polyether macrodiol alone.

Example 7

Synthesis of Polyisobutylene/Polyether-Based Thermoplastic Urethane (PIB-PTMO-TPU, 50A Shore Hardness)

TPU having mixture of PIB and PTMO in 80:20 weight proportion as soft segment was synthesized using the two-step procedure according to the synthetic procedure exemplified in FIG. 2. BDO and MDI constituted the hard segment. The soft segment to hard segment ratio of 82:18 wt % was maintained.

For example, PIB-PTMO-82-5 was synthesized as follows. HO-Allyl-PIB-Allyl-OH ($M_n$=2250, 5.0 g, 2.2 mmol) and PTMO ($M_n$=1000, 1.25 g, 1.25 mmol) were dried by azeotropic distillation from dry toluene (10 mL) solution. The mixture was kept at 45° C. for 3 hours under vacuum. 25 mL of dry toluene was added to this mixture, followed by Sn(Oct)$_2$ (20.3 mg, 0.05 mmol) in toluene. The mixture was heated at 80° C. under a slow stream of dry nitrogen gas. MDI (1.32 g, 5.3 mmol) was added to this mixture and the mixture was stirred vigorously for 30 min. BDO (170 mg, 1.87 mmol) was added to the resulting reaction mixture and the mixture was stirred for 4 hours at 100° C. The mixture was cooled to room temperature, poured in a Teflon® mold and the solvent was evaporated at room temperature in air for 48 hours. Finally the polymer was dried under vacuum at 50° C. for 12 hours.

The TPU exhibited the following characteristics: $M_n$=75000, PDI=1.7, UTS=14 MPa and elongation at break=800%, Young's modulus=3 MPa, flexural modulus=11 MPa, tear strength=292 pli.

Example 8

Synthesis of Polyisobutylene/Polyether-Based Thermoplastic Urethane (PIB-PTMO-TPU, 55a Shore Hardness)

TPU having mixture of PIB and PTMO in 80:20 weight proportion as soft segment was synthesized using the two-step procedure according to the synthetic procedure exemplified in FIG. 2. BDO and MDI constituted the hard segment. The soft segment to hard segment ratio of 81:19 wt % was maintained.

For example, PIB-PTMO-82-5.5 was synthesized as follows. HO-Allyl-PIB-Allyl-OH ($M_n$=2250, 5.4 g, 2.4 mmol) and PTMO ($M_n$=1000, 1.35 g, 1.35 mmol) were dried by azeotropic distillation from dry toluene (10 mL) solution. The mixture was kept at 45° C. for 3 hours under vacuum. 25 mL of dry toluene was added to this mixture, followed by Sn(Oct)$_2$ (25.9 mg, 0.06 mmol) in toluene. The mixture was heated at 80° C. under a slow stream of dry nitrogen gas. MDI (1.55 g, 6.21 mmol) was added to this mixture and the mixture was stirred vigorously for 30 min. BDO (223 mg, 2.46 mmol) was added to the resulting reaction mixture and the mixture was stirred for 4 hours at 100° C. The mixture was cooled to room temperature, poured in a Teflon® mold and the solvent was evaporated at room temperature in air for 48 hours. Finally the polymer was dried under vacuum at 50° C. for 12 hours.

The TPU exhibited the following characteristics: $M_n$=105000, PDI=2.0, UTS=13 MPa, elongation at break=900%, Young's modulus=3.6 MPa, tear strength is 295 pli.

Example 9

Synthesis of (Saturated) Polyisobutylene/Polyether-Based Thermoplastic Urethane (PIB$_{sat}$-PTMO-TPU, 60A Shore Hardness)

TPU having mixtures of hydroxypropyl telechelic PIB and PTMO in different weight proportions as soft segment was synthesized using the two-step procedure according to the synthetic procedure exemplified in FIG. 2. BDO and MDI constituted the hard segment. The soft segment to hard segment ratio of 77:23 wt % was maintained.

For example, PIB$_{sat}$-PTMO-82-6 was synthesized as follows. HO-propyl-PIB-propyl-OH ($M_n$=2000, 5.3 g, 2.65 mmol), obtained by hydroboration oxidation of allyl telechelic PIB (Iván, B.; Kennedy, J. P. *J. Polym. Sci., Part A: Polym. Chem.* 1990, 28, 89), and PTMO ($M_n$=1000, 1.33 g, 1.33 mmol) were dried by azeotropic distillation from dry toluene (10 mL) solution. The mixture was kept at 45° C. for 3 hours under vacuum. 25 mL of dry toluene was added to this mixture, followed by Sn(Oct)$_2$ (29.9 mg, 0.074 mmol) in toluene. The mixture was heated at 80° C. under a slow stream of dry nitrogen gas. MDI (1.84 g, 7.36 mmol) was added to this mixture and the mixture was stirred vigorously for 30 min. BDO (308 mg, 3.38 mmol) was added to the resulting reaction mixture and the mixture was stirred for 4 hours at 100° C. The mixture was cooled to room temperature, poured in a Teflon® mold and the solvent was evaporated at room temperature in air for 48 hours. Finally the polymer was dried under vacuum at 50° C. for 12 hours.

The TPU exhibited the following characteristics: $M_n$=140000, PDI=2.2, UTS=20 MPa, elongation at break=550%, Young's modulus=6 MPa.

Example 10

Synthesis of Polyisobutylene (Saturated)/Polyether-Based Thermoplastic Urethane (PIB$_{sat}$-PTMO-TPU, 80A Shore Hardness)

TPU having mixtures of hydroxypropyl telechelic PIB and PTMO in different weight proportions as soft segment was synthesized using the two-step procedure according to the synthetic procedure exemplified in FIG. 2. BDO and MDI constituted the hard segment. The soft segment to hard segment ratio of 66:34 wt % was maintained in all the cases.

PIB$_{sat}$-PTMO-82-8 was synthesized as follows. HO-propyl-PIB-propyl-OH $M_n$=2000, 5.2 g, 2.6 mmol) and PTMO ($M_n$=1000, 1.3 g, 1.3 mmol) were dried by azeotropic distillation from dry toluene (10 mL) solution. The mixture was kept at 45° C. for 3 hours under vacuum. 25 mL of dry toluene was added to this mixture, followed by Sn(Oct)$_2$ (42.5 mg, 0.105 mmol) in toluene. The mixture was heated at 80° C. under a slow stream of dry nitrogen gas. MDI (2.64 g, 10.54 mmol) was added to the reaction mixture, and the mixture was stirred vigorously for 30 min. BDO (604 mg, 6.64 mmol) was added to the reaction mixture, and the mixture was stirred for 4 hours at 100° C. The mixture was cooled to room temperature, poured in a Teflon® mold and the solvent was evaporated at room temperature in air for 48 hours. Finally the polymer was dried under vacuum at 50° C. for 12 hours.

The TPU exhibited the following characteristics: $M_n$=85000, PDI=2.2, UTS=27 MPa, elongation at break=475%, Young's modulus=15 MPa.

Example 11

Synthesis of Polyisobutylene/Polyether-Based Thermoplastic Urethane (PIB-polyhexamethylene Oxide(PHMO)-TPU, 80A Shore Hardness)

TPU having mixtures of PIB and PHMO in different weight proportions as soft segment was synthesized using the two-step procedure according to the synthetic procedure exemplified in FIG. 2. BDO and MDI constituted the hard segment. The soft segment to hard segment ratio of 67:33 wt % was maintained.

For example, PIB-PHMO-82-8 was synthesized as follows. HO-Allyl-PIB-Allyl-OH ($M_n$=2200, 4.6 g, 2.1 mmol) and PHMO ($M_n$=920, 1.15 g, 1.25 mmol) were dried by azeotropic distillation from dry toluene (10 mL) solution. The mixture was kept at 45° C. for 3 hours under vacuum. 25 mL of dry toluene was added to this mixture, followed by Sn(Oct)$_2$ (37.26 mg, 0.092 mmol) in toluene. The mixture was heated at 80° C. under a slow stream of dry nitrogen gas. MDI (2.3 g, 9.22 mmol) was added to this mixture and the mixture was stirred vigorously for 30 min. BDO (534 mg, 5.87 mmol) was added to the resulting reaction mixture and the mixture was stirred for 4 hours at 100° C. The mixture was cooled to room temperature, poured in a Teflon® mold and the solvent was evaporated at room temperature in air for 48 hours. Finally the polymer was dried under vacuum at 50° C. for 12 hours.

The TPU exhibited the following characteristics: $M_n$=73000, PDI=3.4, UTS=18 MPa, elongation at break=280%, Young's modulus=27 MPa.

Example 12

Synthesis of Polyisobutylene (Saturated)/Polyether-Based Thermoplastic Urethane (PIB$_{sat}$-PHMO-TPU, 60A Shore Hardness)

TPU having mixtures of hydroxypropyl telechelic PIB and PHMO in different weight proportions as soft segment was synthesized using the two-step procedure according to the synthetic procedure exemplified in FIG. 2. BDO and MDI constituted the hard segment. The soft segment to hard segment ratio of 76:24 wt % was maintained in all the cases.

For example, PIB$_{sat}$-PHMO-82-6 was synthesized as follows. HO-propyl-PIB-propyl-OH ($M_n$=2000, 4.6 g, 2.3 mmol) and PHMO ($M_n$=920, 1.15 g, 1.25 mmol) were dried by azeotropic distillation from dry toluene (10 mL) solution. The mixture was kept at 45° C. for 3 hours under vacuum. 25 mL of dry toluene was added to this mixture, followed by Sn(Oct)$_2$ (26.3 mg, 0.065 mmol) in toluene. The mixture was heated at 80° C. under a slow stream of dry nitrogen gas. MDI (1.62 g, 6.48 mmol) was added to this mixture and the mixture was stirred vigorously for 30 min. BDO (267 mg, 2.93 mmol) was added to the resulting reaction mixture and the mixture was stirred for 4 hours at 100° C. The mixture was cooled to room temperature, poured in a Teflon® mold and the solvent was evaporated at room temperature in air for 48 hours. Finally the polymer was dried under vacuum at 50° C. for 12 hours.

The TPU exhibited the following characteristics: $M_n$=120000, PDI=3.4, UTS=16 MPa, elongation at break=550%, Young's modulus=6 MPa.

Example 13

Synthesis of Polyisobutylene (Saturated)/Polyether-Based Thermoplastic Urethane (PIB$_{sat}$-PTMO-TPU, 95A Shore Hardness) Without Catalyst TPU having mixtures of hydroxypropyl telechelic PIB and PTMO-diol in different weight proportions as soft segment was synthesized using the two-step procedure according to the synthetic procedure exemplified in FIG. 2. BDO and MDI constituted the hard segment. The ration of soft segment to hard segment of 60:40 wt % was maintained in all the cases.

For example, PIB$_{sat}$-PTMO-82-9 was synthesized as follows. HO-propyl-PIB-propyl-OH ($M_n$=2000, 2.8 g, 1.4 mmol) and PTMO ($M_n$=1000, 0.8 g, 0.8 mmol) were dried by azeotropic distillation from dry toluene (10 mL) solution. The mixture was kept at 45° C. for 3 hours under vacuum and 25 mL of dry toluene was added to this mixture. The temperature of the mixture was raised to 100° C. under a slow stream of dry nitrogen gas. MDI (1.92 g, 7.7 mmol) was added to this mixture and the mixture was stirred vigorously for 1 h and 30 min. BDO (500 mg, 5.5 mmol) was added to the resulting reaction mixture and the mixture was stirred for 4 hours at 100° C. The mixture was cooled to room temperature, poured in a Teflon mold and the solvent was evaporated at room temperature in air for 48 hours. Finally the polymer was dried under vacuum at 50° C. for 12 hours.

The TPU exhibited the following characteristics: $M_n$=88000, PDI=3.7.

Example 14

Long Term In Vitro Biostability of Segmented Polyisobutylene-Based Thermoplastic Polyurethanes Long term in vitro biostability of termoplastic polyurethanes (TPUs) containing mixed polyisobutylene (PIB)/poly (tetramethylene oxide) (PTMO) soft segment was studied under accelerated conditions in 20% $H_2O_2$ solution containing 0.1M $CoCl_2$ at 50° C. to predict resistance to metal ion oxidative degradation in vivo. The PIB-based TPUs containing PTMO showed significant oxidative stability as compared to the commercial controls such as Pellethane™ 2686-55D and 2686-80A. After 12 weeks in vitro (equivalent of approximately 10 years in vivo) the PIB-PTMO TPUs with 10-20% PTMO in the soft segment showed 6-15% weight loss whereas the Pellethanes™ degraded completely in about 9 weeks. The weight loss was linearly proportional to the PTMO content in the PIB-PTMO TPUs. ATR-FTIR spectroscopy confirmed the degradation of Pellethanes™™ via MIO by the consistent loss of the approximately 1110 cm$^{-1}$ aliphatic C—O—C stretching peak height attributed to chain scission, and the appearance of a new peak approximately 1174 cm$^{-1}$ attributed crosslinking. No such absorption bands were apparent in the spectra of the PIB-based TPUs. The PIB-based TPUs exhibited 10-30% drop in tensile strength compared to 100% for the Pellethanes™ after 12 weeks. The drop in tensile strength correlated approximately with PTMO content in the TPU. Molecular weight results correlated well with tensile strength, showing a slight decrease 10-15% at 12 weeks. The Pellethanes™ showed a dramatic decrease in Mn as well as an increase in low molecular weight degradation product. SEM showed severe cracking in the Pellethanes™ after two weeks, whereas the PIB-based TPUs exhibited a continuous surface morphology. The weight loss, tensile, and SEM data correlate well with each other and indicate excellent biostability of these materials.

Materials and Methods
Polyurethanes

Control samples consisted of Pellethane™ 2363-55D and Pellethane™ 2363-80A. Polyurethanes of varying hardness and PIB:PTMO compositions were synthesized as reported previously and are listed in Table 24. The two-stage process is described for a representative TPU (60A 82) as follows: HO-Allyl-PIB-Allyl-OH (Mn=2200 g/mol, 5.2 g, 2.36 mmol) and PTMO (Mn=1000 g/mol, 1.3 g, 1.3 mmol) were dried by azeotropic distillation using dry toluene (10 mL).

The mixture was kept at 45° C. for 3 hours under vacuum. To it 25 mL of dry toluene was added followed by Sn(Oct)$_2$ (28.3 mg, 0.07 mmol) in toluene. The mixture was heated at 80° C. under a slow stream of dry nitrogen gas. To it MDI (1.76 g, 7.02 mmol) was added and the mixture was stirred vigorously for 30 min. To it BDO (302 mg, 3.36 mmol) was added and the mixture was stirred at 100° C. for 4 hours. The mixture was cooled to room temperature, poured into a Teflon® mold and the solvent was evaporated at room temperature in air for 48 hours. Finally, the polymer was dried under vacuum at 50° C. for 12 hours. A PIB TPU without PTMO was prepared similarly. The saturated PIB-PTMO polyurethane was synthesized using HO-propyl-PIB-propyl-OH, prepared using a method developed by Kennedy (Iván, B.; Kennedy, J. P. *J. Polym. Sci., Part A: Polym. Chem.* 1990, 28, 89). The polyurethanes were characterized prior to accelerated degradation using 1H NMR and GPC. The harder compositions (80A 91, 100A) did not dissolve in the GPC eluent.

TABLE 24

PIB and PTMO wt %

| Code | HO-PIB-OH[a] (wt % in SS) | HO-PTMO-OH[b] (wt % in SS) | SS:HS (wt:wt) | PTMO wt % in TPU | Shore A hardness |
|---|---|---|---|---|---|
| P55D | 0 | 100 | 60:40 | 60 | 100 |
| P80A | 0 | 100 | 65:35 | 65 | 80 |
| 60A 82 | 80 | 20 | 79:21 | 16 | 60 |
| 60A 91 | 90 | 10 | 79:21 | 8 | 60 |
| 80A 73 | 70 | 30 | 65:35 | 19.5 | 80 |
| 80A 82 | 80 | 20 | 65:35 | 13 | 80 |
| 80A 91 | 90 | 10 | 65:35 | 6.5 | 80 |
| 100A 82 | 80 | 20 | 60:40 | 12 | 100 |
| PIB 60A | 100 | 0 | 79:21 | 0 | 60 |
| SAT 60A 91 | 90 | 10 | 79:21 | 8 | 60 |

[a] HO-PIB-OH, Mn = 2200 g/mol.
[b] HO-PTMO-OH, Mn = 1000 g/mol

The polyurethanes were compression molded using a Carver Laboratory Press model C at a load of 16,000 lbs. at 160° C. They were molded into thin films ranging in thickness from 0.2 mm-0.5 mm and cut into rectangular strips with approximate dimensions of 3 mm in width and 30 mm in length.

In Vitro Accelerated Degradation

The samples were placed in vials and soaked in a 20% H$_2$O$_2$ in aqueous 0.1 M CoCl$_2$ solution and stored at 50° C. The solutions were changed every other day to ensure a steady concentration of radicals. At time points after 1, 2, 4, 6, and 12 weeks, dedicated samples were removed from the oxidative environment, washed 7 times in aqueous 1% Triton X-100 surfactant solution, 5 times in ethanol, and 5 times in distilled water and dried under vacuum at 80° C. until constant weight.

Characterization

Dry samples were characterized by weight loss, ATR-FTIR, ultimate tensile strength, elongation at break, SEM, and GPC. Each data point consisted of three identical samples. Of the quantitative data, the reported value is an average of the three samples.

ATR-FTIR

ATR-FTIR was performed on a Thermo Electron Corporation Nicolet 4700 FT-IR with a Thermo Electron Corporation Smart Orbit attachment for ATR with a diamond crystal. Thirty-two scans were averaged to obtain one representative spectrum for each sample. The respective dry clean TPU strip was placed on the crystal, firmly secured using the foot attachment, and scanned for analysis. The region of interest was between approximately 1700 cm$^{-1}$ and 1100 cm$^{-1}$, which includes HS degradation product (approximately 1650 cm$^{-1}$), SS degradation moiety (approximately 1110 cm$^{-1}$) and product (approximately 1170 cm$^{-1}$) and the normalized reference peak (approximately 1410 cm$^{-1}$).

Weight Loss

Weights were measured of dry polyurethane films before and after oxidative treatment on a Sartorius MC1 Analytic AC 210S balance.

Mechanical Testing

Tensile testing was performed at room temperature and atmospheric conditions with a 50 lb. load cell on an Instron Model Tensile Tester 4400R at 50 mm/min extension rate until failure. Ultimate tensile strength and elongation at break were recorded.

GPC Analysis

Molecular weights and molecular weight distributions were measured with a Waters HPLC system equipped with a model 510 HPLC pump, model 410 differential refractometer, model 441 absorbance detector, online multiangle laser light scattering (MALLS) detector (MiniDawn, Wyatt Technology Inc.), Model 712 sample processor, and five Ultrastyragel GPC columns connected in the following series: 500, 10$^3$, 10$^4$, 10$^5$, and 100 Å. THF:TBAB (98:2, wt:wt) was used as a carrier solvent with a flow rate of 1 mL/min.

Scanning Electron Microscopy

Portions of the dry treated films were isolated for SEM analysis. Surface morphology was observed on gold sputter coated samples using a Denton Vacuum Desk IV Cold Cathode Sputter Coater. The samples were sputter coated for 1.5 min at 25% power, corresponding to a thickness of approximately 15Å of gold. The coated samples were observed using a JEOL model JSM 7401F field emission scanning electron microscope. Several representative pictures were taken at 30× and 300× magnification.

3. Results and Discussion

ATR-FTIR

ATR-FTIR analysis was performed to confirm the presence and progression of the MIO mechanism as put forth by Schubert and coworkers. According to their suggested mechanism, a hydroxyl radical may abstract an α-hydrogen from the polyether segment. The resulting radical may combine with another chain radical to form a crosslink junction or react with another hydroxyl radical to form a hemiacetal. The hemiacetal oxidizes to ester which is subsequently acid hydrolyzed resulting in chain scission. Therefore progression of degradation can be observed by following the disappearance of the SS ether peak and/or the appearance of the crosslinking peak. All spectra were normalized to the peak at 1410 cm$^{-1}$, which corresponds to the aromatic C—C stretch of the hard segment.

Figure 6:
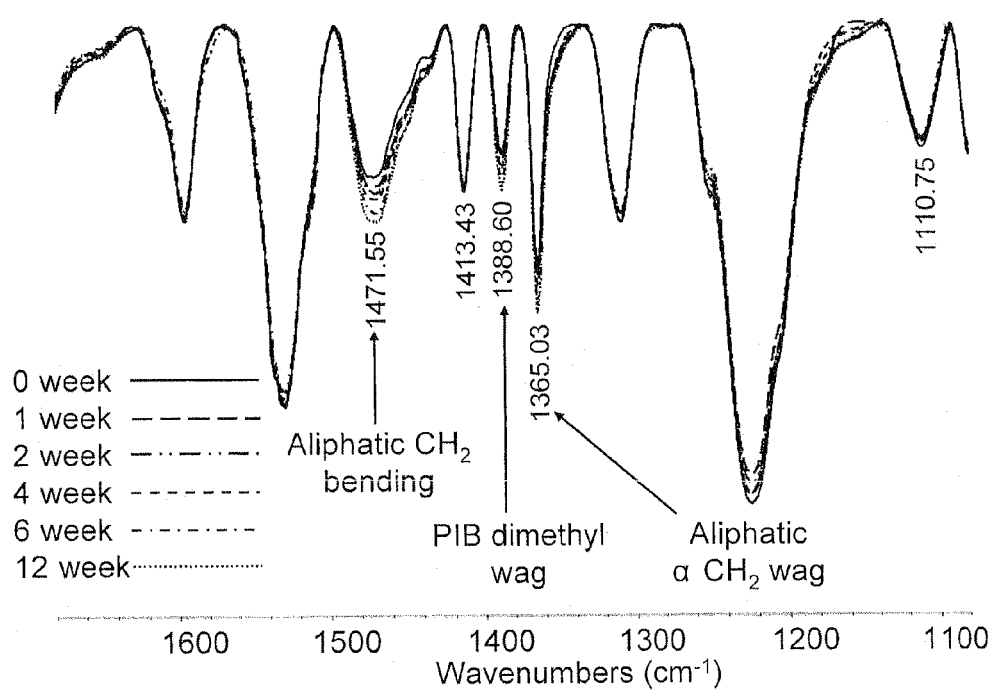
FIG. 6 is a representative FTIR spectrum of 60A 82 PIB-PTMO polyurethanes of the present invention.

The PIB-PTMO polyurethanes all show very small changes in the FTIR spectrum. A representative spectrum, that of 60A 82, is shown in FIG. 6.

As can be seen, There is no appreciable change in the aliphatic ether C—O—C absorbance at 1110 cm$^{-1}$ and C—O—C branching absorbance at approximately 1174 cm$^{-1}$ is absent. However, an increase in the aliphatic absorbances with time is observed (aliphatic CH$_2$ bending at 1470 cm$^{-1}$, PIB dimethyl wag at 1388 cm$^{-1}$, and aliphatic α-CH$_2$ wag at 1365 cm$^{-1}$). This behavior can be rationalized by migration of PIB segments to the surface during vacuum drying at 80° C. In these PIB-PTMO TPUs cross-linking may be absent since there is not a significant presence or mobility of PTMO to allow two polymer radicals to combine before they are otherwise cleaved. Similar results are observed in the other PIB-PTMO TPU spectra. The Sat 60A 91 batch was included in this study to determine if the unsaturated allyl moiety in the PIB diol was vulnerable to oxidation. The FTIR spectrum of the TPU using the saturated diol appears identical to that of the TPU containing unsaturated diol. Additionally the PIB 60A TPU was included to confirm that there is only polyether SS degradation, and not HS degradation in these TPUs. This hypothesis was confirmed as the spectrum shows no change at all. There is no change in the PIB absorbance at 1388 cm$^{-1}$ or ether absorbance at 1111 cm$^{-1}$ since there is no polyether to be degraded. There is also no evidence of HS degradation. In Table 25 are listed the IR absorbances where trends of change were observed.

TABLE 25

Assigned ATR-FTIR Spectral Peak Changes

| Wave number (cm-1) | Proposed peak assignment | P80A | P55D | PIB-PTMO |
|---|---|---|---|---|
| 1637 | NH2 aromatic amine | X | | |
| 1476 | Aliphatic CH2 bend | | | X |
| 1388 | PIB CH3 wag | | | X |
| 1365 | Aliphatic α-CH2 wag | X | X | X |
| 1173 | C-O-C branching | X | X | |
| 1110 | Aliphatic C-O-C | X | X | |

Figure 7:
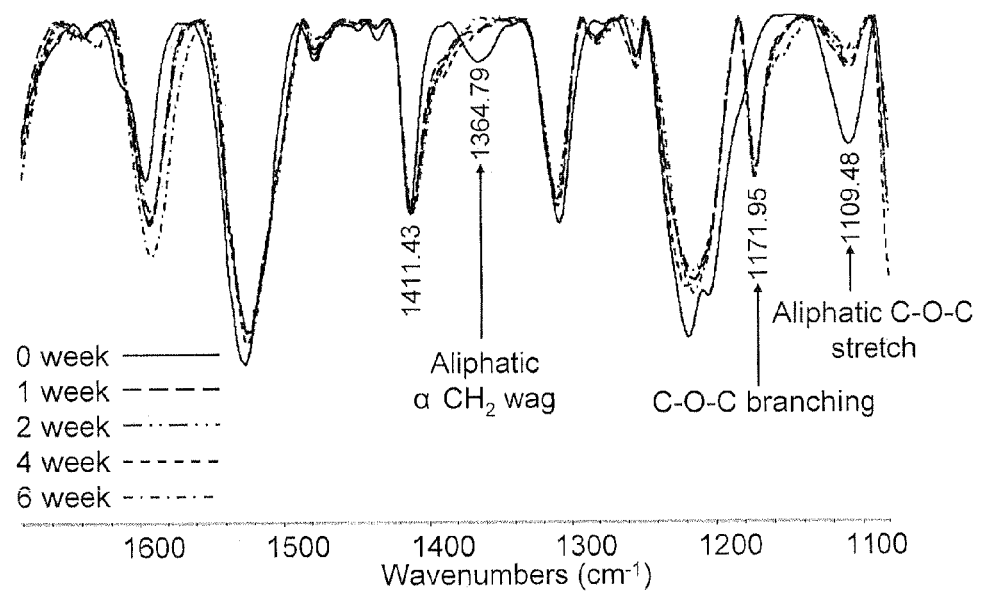
FIG. 7 is a FTIR spectrum of Pellethane™ P55D.

The Pellethane™ samples showed the expected behavior as is consistent with previous studies. The spectra of P55D are shown in FIG. 7.

The spectrum shows a significant decrease in aliphatic C—O—C absorption at 1109 cm$^{-1}$ after 1 week, then more slowly until 6 weeks. Concurrently, we observe a rapid disappearance of the aliphatic α-CH$_2$ absorbance at 1364 cm$^{-1}$ after just one week. Also the C—O—C branching absorbance at 1172 cm$^{-1}$ is observed immediately at 1 week, then stays constant in magnitude. As it will be seen later, the Pellethanes™ continued to degrade at a constant, if not accelerated rate after 1 week, and so an explanation is in order for the IR spectra. ATR-FTIR is a surface characterization technique and degradation is expected to begin at the surface. Therefore we conclude that the segments vulnerable at the surface are oxidized almost immediately and deeper oxidation occurs in the following weeks as observed from the rest of the analyses.

Weight Loss

Figure 8:
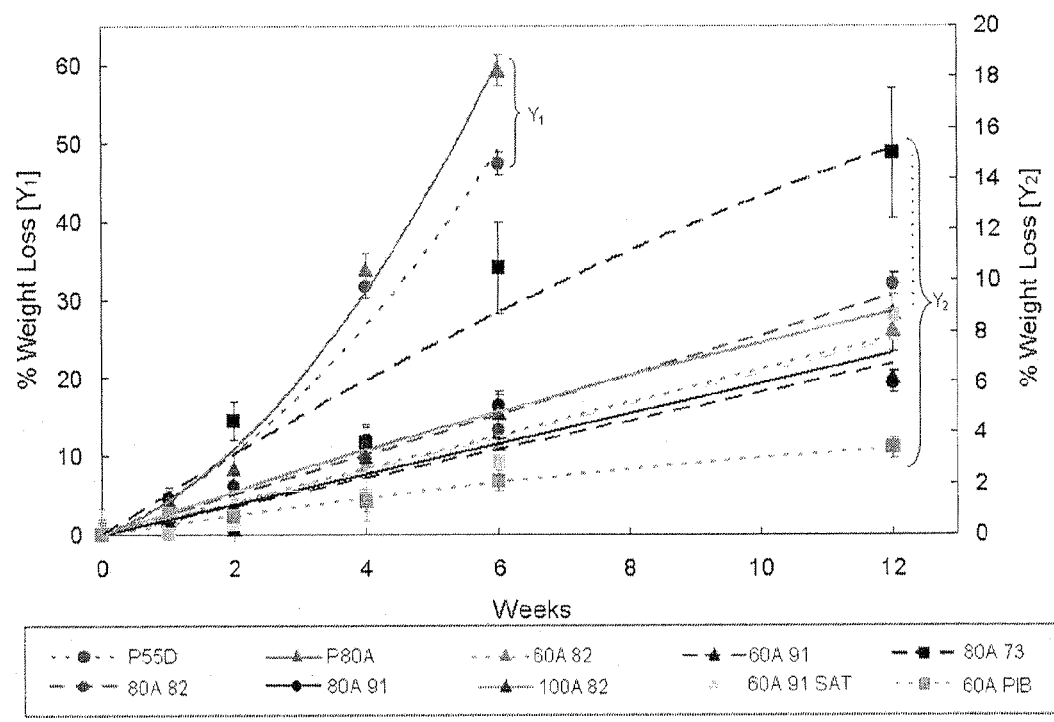
FIG. 8 is a plot of the weight loss of various PIB-PTMO polyurethanes as a function of time of the present invention.
Figure 9:
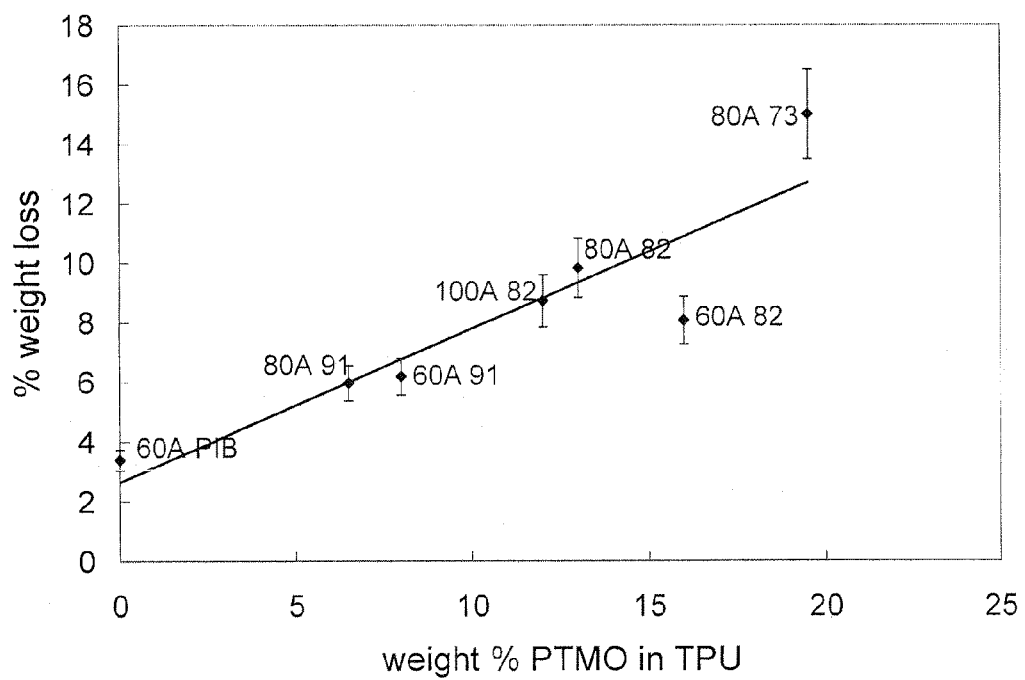
FIG. 9 is a plot of the weight loss of various PIB-PTMO polyurethanes of the present invention at 12 weeks as a function of PTMO content.

The weight loss plotted against time is shown in FIG. 8. The PIB-PTMO TPUs all show very low weight loss after 12 weeks ranging from values of 6-15% depending on the composition. Among the 60A batch, the 90/10 composition showed lower weight loss of 6% compared to 8% for the 80/20 composition. The Sat 60A 91 shows weight loss comparable to the unsaturated 60A 91. Similarly in the 80A batch, the TPUs with lower PTMO content showed lower weight loss, from 15, 10 and 6% for 30, 20, and 10% PTMO respectively. More specifically, the weight loss could be correlated to the PTMO content in the polyurethanes. In FIG. 9 weight loss at 12 weeks vs. PTMO content is plotted.

As can be seen for the PIB-PTMO TPUs there is approximately a linear relationship between the weight loss and the PTMO content. This discovery supports the notion that it is the polyether SS which degrades via MIO and it is these portions which are excised from the polyurethane. Interestingly, 60A 82 showed a lower weight loss than expected for its PTMO content. The TPU which contained only PIB also showed a small weight loss, which fits the plot. Since there is such a large surface area to volume ratio, we expect to see some small erosion from the surface. The Pellethane™ control samples showed noticeable weight loss even after 1 week in vitro, and P80A and P55D completely degraded after approximately 7 and 9 weeks, respectively. These findings are consistent with previous findings concerning such polyether based TPUs.

Mechanical Properties

Figure 10:
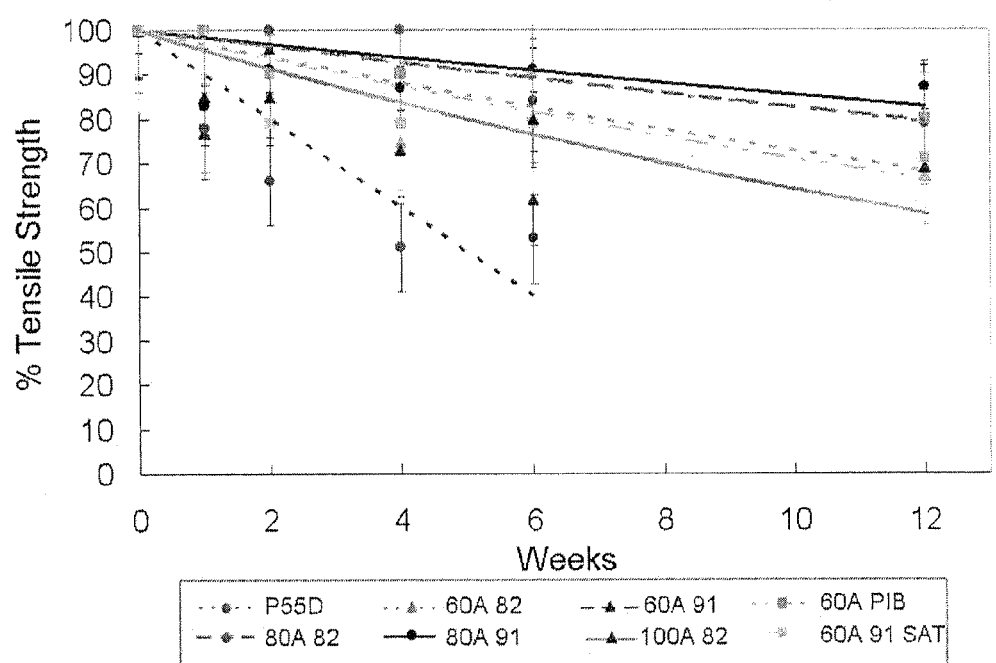
FIG. 10 is a plot of tensile strength of various PIB-PTMO polyurethanes of the present invention as a percentage of the original untreated sample as a function of time.

Tensile strength is plotted as a percentage of the original untreated sample vs. time in FIG. 10.

A drastic difference in the plots for P55D versus the PIB-PTMO TPUs can be seen. In the PIB-PTMO TPUs a minimal decrease in tensile strength is observed for all samples, although the rate of tensile loss varies for the different samples. The PIB-PTMO TPUs show differing losses which are roughly correlated to the PTMO content. Among the 60A batch, the tensile losses from the different compositions are comparable. The 12 weeks data point for the 60A 91 could not be obtained because of a poor sample set. Nevertheless, the trend observed up to 6 weeks follows very closely that of the Sat 60A 91. Minimal decrease in tensile strength was also observed in the 60A PIB sample, which showed no degradation as evident from weight loss and FTIR studies. This indicates that 1-2 MPa may be within experimental error with the load cell and instrument used. Among the 80A batch the 80/20 composition shows ~21% drop in tensile strength, whereas the 90/10 composition shows only a decrease of ~13%. The 80A 73 sample (not shown) showed an initial increase in tensile strength, then subsequently a slower decrease. This is attributed to be due to crosslinking initially, followed by chain scission consistent with the increased amount of PTMO in this sample. At this amount of PTMO (19.5% of total TPU), there are sufficient concentration of chain radicals such that crosslinking is able to occur as well as chain scission. Although the % tensile strength at 12 weeks is greater than the other PIB-PTMO TPUs, extrapolation of the data would predict that the tensile strength 80A 73 would drop more sharply at longer time intervals.

P55D shows greater resistance to degradation compared to P80A due to more crystallinity. Thus the 100 A 82 composition is expected to have comparable if not better strength than the 80A 82 composition, yet we see greater tensile drop. This may suggest that PIB is a better protector of the surface than the hard segment. Some of the samples actually show inhibition periods wherein the tensile strength does not begin to decrease until 2, 4, or even 6 weeks (esp. 80A 82). The ultimate elongation of the PIB-PTMO TPUs did not change significantly over the course of the treatment. The Pellethanes™ again showed expected of MIO behavior. P55D showed gradual tensile loss over time up to 6 weeks, and at 12 weeks there was no sample to test. P80A (not shown) showed an initial increase in tensile strength after one week, then a gradual decrease.

This is explained by crosslinking of the chains initially, with chain scission occurring afterward as was observed with 80A 73.

GPC Analysis

Figure 11:
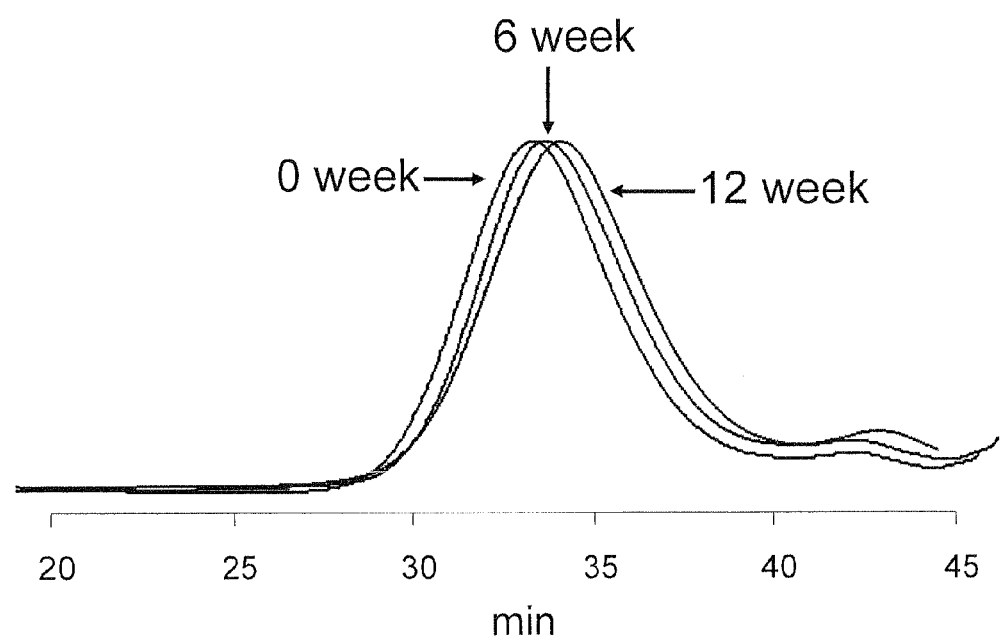
FIG. 11 is an a Gas Permeation Chromatography (GPC)/Refractive Index (RI) detection profile of a PIB-PTMO polyurethane sample of the present invention, "Sat 60A91". The elution time is indicated in minutes.

The TPU samples were dissolved in the carrier solvent of THF:TBAB (98:2, wt:wt). However, some of the harder compositions could not be dissolved. Representative GPC RI traces are shown FIG. 11 for Sat 60A91. The TBAB elutes beyond 47 minutes.

The loss in molecular weight is minimal in agreement with the weight loss and tensile data. Mn decreases slightly from 130,000 g/mol to 112,000 g/mol after 6 weeks, then negligibly to 110,000 g/mol at 12 weeks while the PDI remained unchanged at 1.6. These data are in agreement with the FTIR and tensile data.

Figure 12:
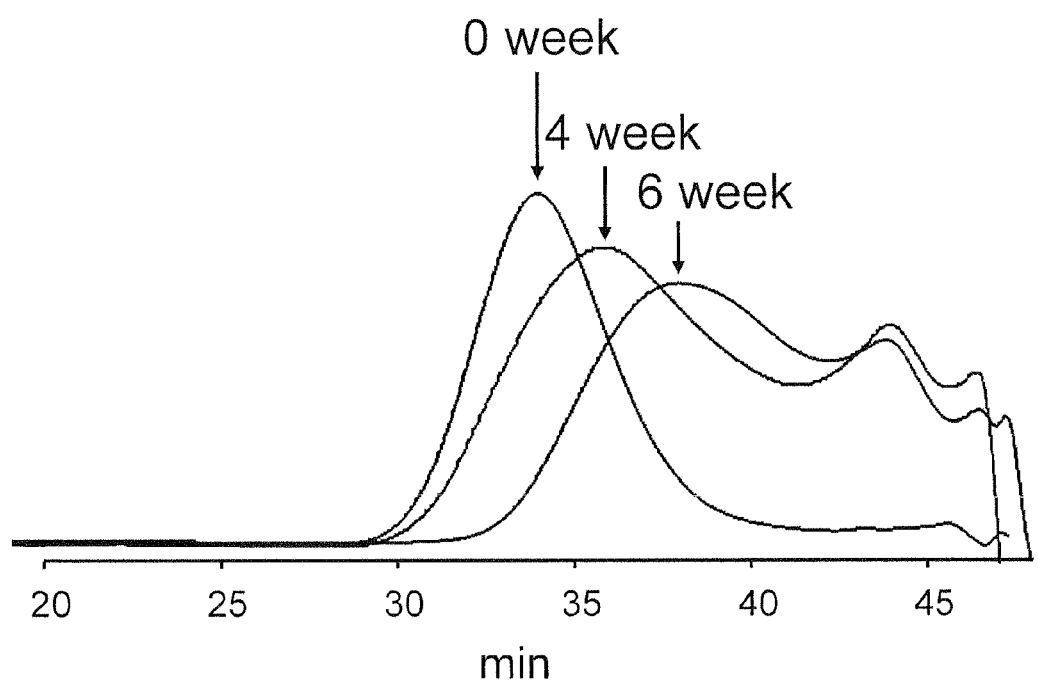
FIG. 12 is a GPC/RI profile of Pellethane™ P80A shown for comparison with the profile of "Sat 60A91" of FIG. 11.

In FIG. 12 the refractive index traces of P80A are shown. The number average molecular weight shows a clear trend decreasing from 84,000 g/mol before treatment to 18,000 g/mol at 4 weeks and 14,000 g/mol at 6 weeks. There is a clearly visible rise in some low molecular weight degradation product(s) by 4 weeks. Simultaneously there is an increase in the molecular weight distribution. These findings are in agreement with the ATR-FTIR, weight loss, and tensile results. P55D shows similar behavior with decreasing Mn and increasing PDI.

SEM

Figure 13:
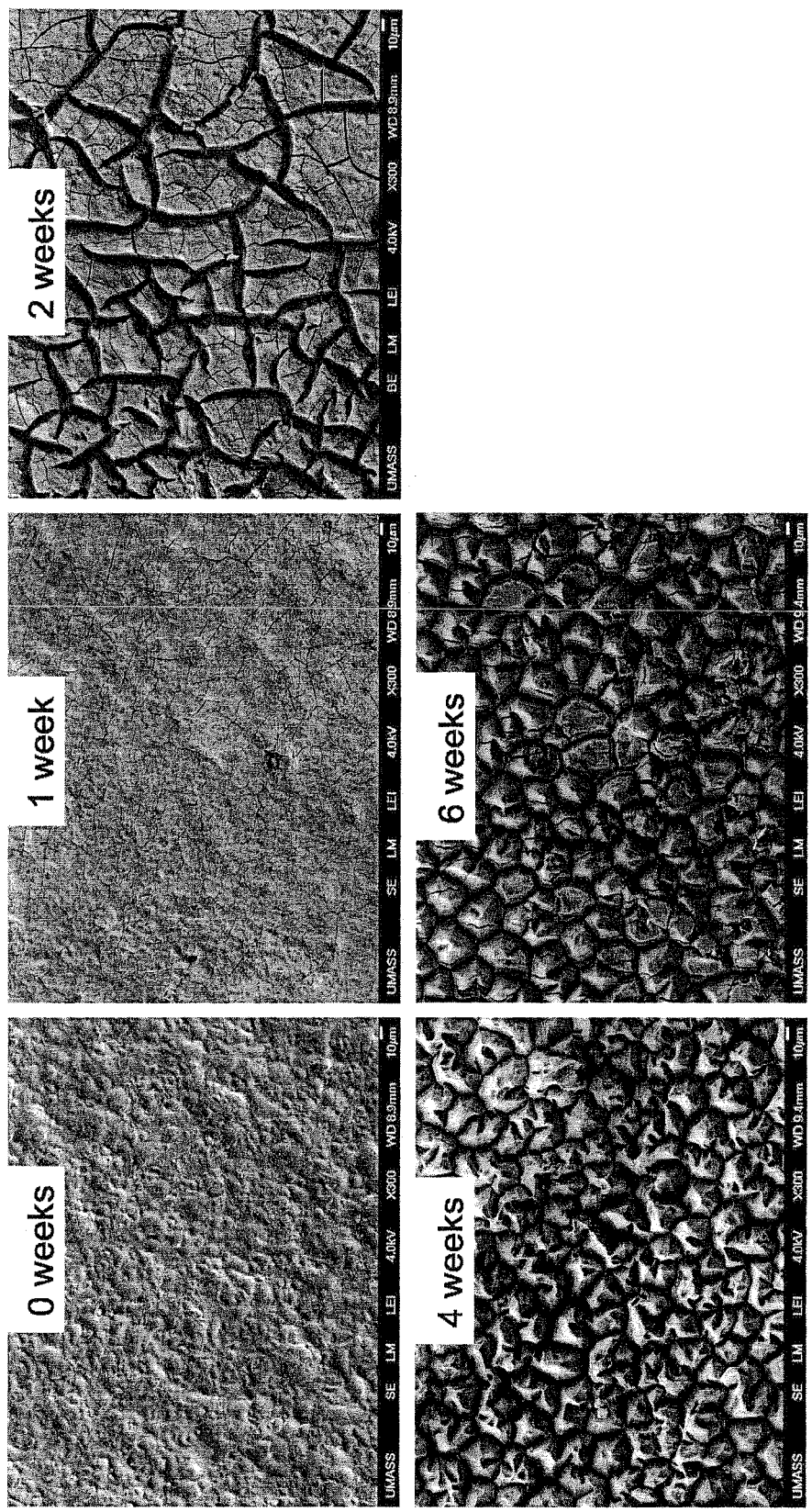
FIG. 13 depicts SEM pictures of Pellethane™ P55D taken at 300× magnification.

Representative SEM pictures taken at 300× magnification are shown in FIGS. 13-16. Shown in FIG. 13 is P55D which shows the often observed behavior of "mud cracking" with treatment time. The surface density of cracks increases with time, and the visual inspection affirms the previous data as well.

Figure 14:
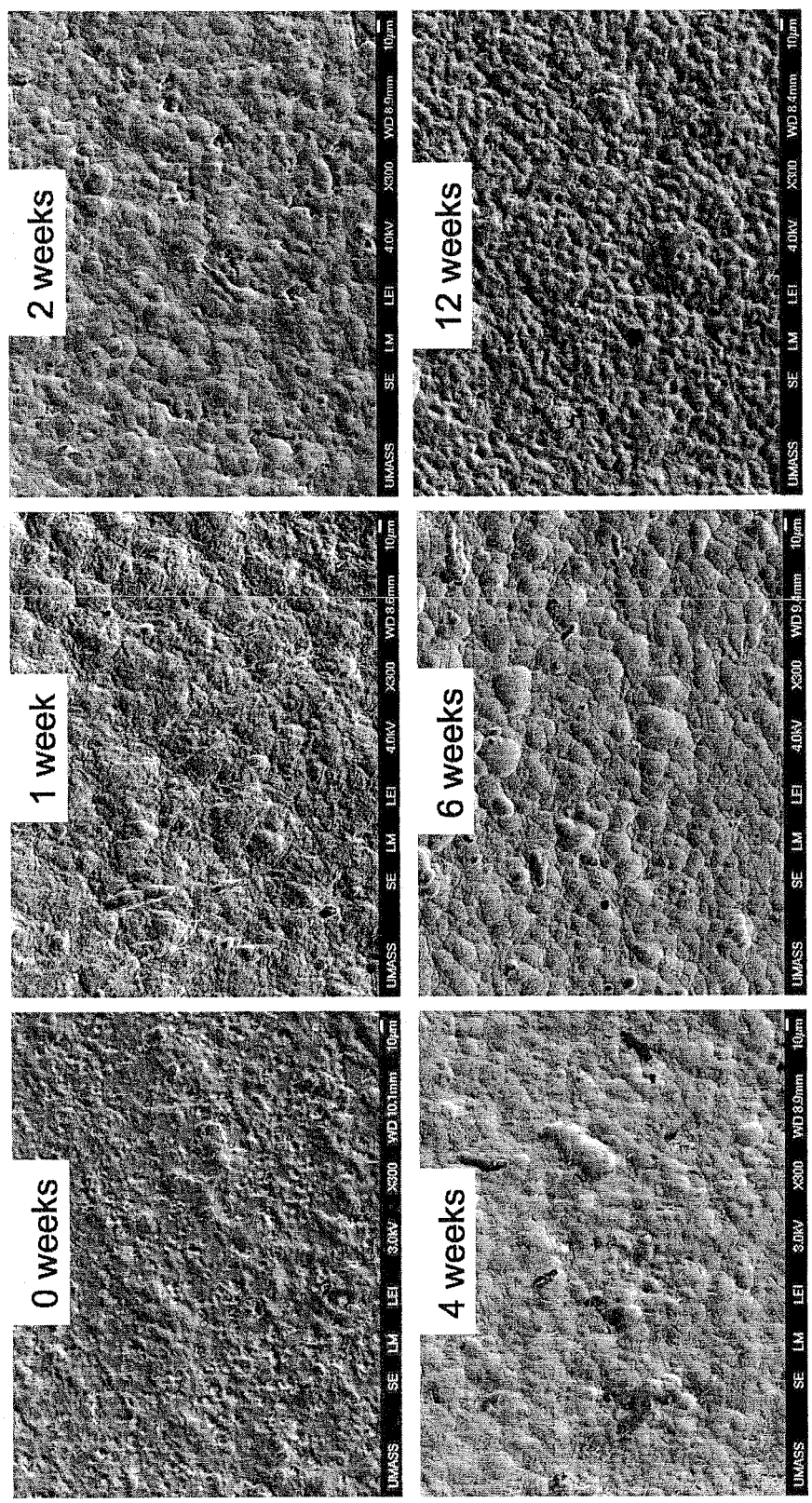
FIG. 14 depicts SEM pictures of PIB-PTMO polyurethane sample of the present invention, "80A 73" at 300× magnification.
Figure 15:
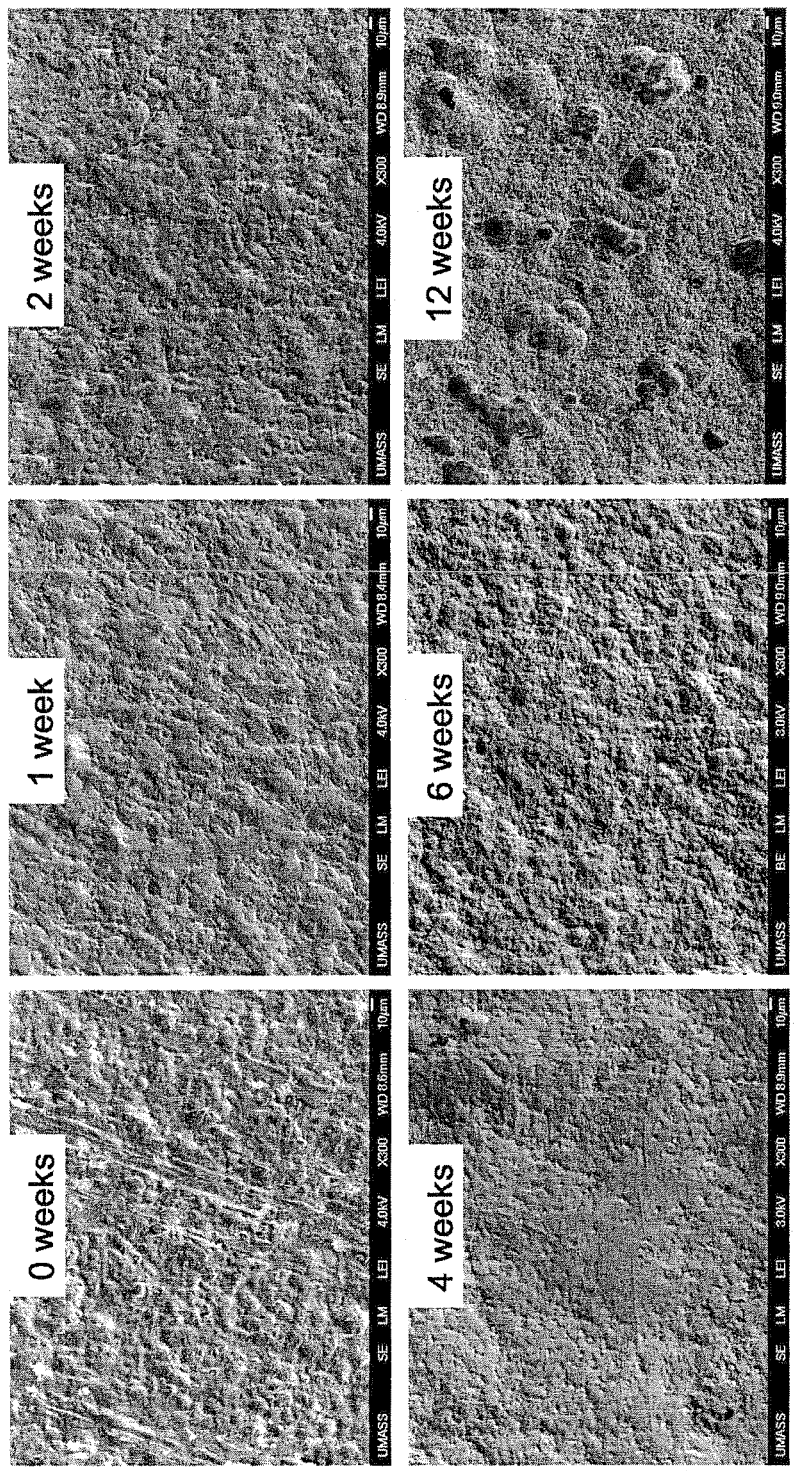
FIG. 15 depicts SEM pictures of PIB-PTMO polyurethane sample of the present invention, "80A 82" at 300× magnification.
Figure 16:
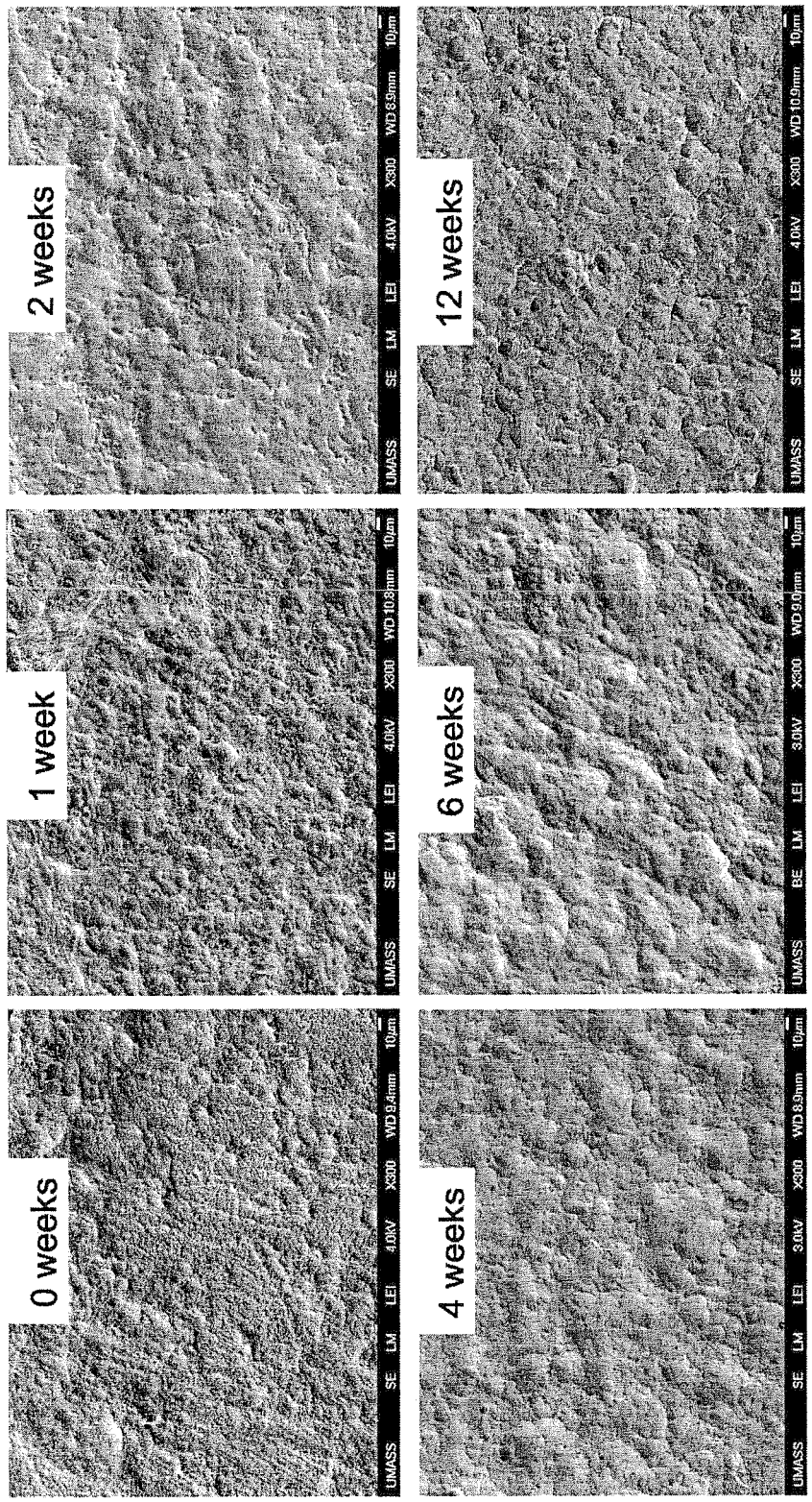
FIG. 16 depicts SEM pictures of PIB-PTMO polyurethane sample of the present invention, "80A 91" at 300× magnification.

In FIG. 14, FIG. 15 and FIG. 16, scanning electron micrographs of the 80A series are shown to depict the effect of PTMO content on the surface morphology. The responses of these TPUs to degradation are certainly different than the Pellethanes™, but a trend of increasing surface imperfections with increasing PTMO content can be seen. The 80A 73 shows some small holes as well as surface roughening after 12 weeks. 80A 82 shows somewhat larger craters after 12 weeks, and 80A 91 shows essentially no change in the surface morphology after 12 weeks. Some small holes are often observed in various samples, but these are not expected to be due to degradation. The same patterns were observed in the 60A PIB samples, which did not degrade; therefore such holes are expected to be an artifact of the compression molding process.

The 60A series show analogous morphologies, with the 90/10 composition showing a less flawed surface. The 100A 82 composition shows morphology comparable to 80A91.

Conclusion

After 12 weeks in vitro, which correlates to approximately 10 years in vivo, the thermoplastic polyurethanes of the present invention showed minimal degradation and minimal decrease in performance. Using unsaturated PIB diol rather than saturated PIB diol did not have an effect on the degradation of the thermoplastic polyurethanes of the invention. The PIB segment and the hard segment were not observed to degrade. Increasing the amount of polyether diol incorporated in the thermoplastic polyurethanes of the invention increased the degradation rate, suggesting a degradation mechanism identical to that postulated before for PTMO-based thermoplastic polyurethanes. Therefore, a low PTMO content was considered to be desirable to ensure biostability.

Equivalents

While this invention has been particularly shown and described with references to example embodiments thereof, it will be understood by those skilled in the art that various changes in form and details may be made therein without departing from the scope of the invention encompassed by the appended claims.

What is claimed is:

1. An elastomeric polymer, consisting of:
   (1) a hard segment in the amount of 32% to 36% by weight of the elastomeric polymer, wherein the hard segment consists of:
      a urethane, urea or urethane urea;
      optionally at least one chain extender; and
      optionally at least one diisocyanate residue; and
   (2) a soft segment in the amount of 64% to 68% by weight of the elastomeric polymer, wherein the soft segment consists of:
      (a) about 10% to about 30% by weight of the soft segment of a combination of at least one polyether macrodiol and at least one polycarbonate macrodiol; and
      (b) about 70% to about 90% by weight of the soft segment of at least one polyisobutylene macrodiol and/or diamine;
   wherein the number average molecular weight of the elastomeric polymer is not less than 40 kilodaltons, and wherein the at least one polyether macrodiol is selected from the group consisting of poly(propylene oxide) diol, poly(trimethylene oxide) diol, poly(tetramethylene oxide) diol, poly(hexamethylene oxide) diol, poly(heptamethylene oxide) diol, poly(octamethylene oxide) diol and poly(decamethylene oxide) diol.

2. The elastomeric polymer of claim 1, wherein the number average molecular weight of the elastomeric polymer is not less than 50 kilodaltons.

3. The elastomeric polymer of claim 1, wherein the at least one polyisobutylene macrodiol or diamine is of formula:

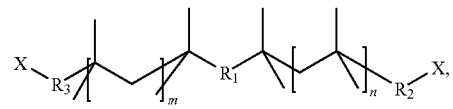

wherein:
   each X is independently —OH, —NH$_2$ or —NHR$_4$;
   R$_i$ is an initiator residue;
   R$_2$ and R$_3$ and R$_4$ is each independently a C1—C16 alkyl, a C3—C16 cycloalkyl, a C2—C16 alkenyl, a C3—C16 cycloalkenyl, or a C6—C18 aryl, wherein, for each occurrence, R$_2$ or R$_3$ is, independently, optionally substituted with one or more groups selected from halo, cyano, nitro, dialkylamino, trialkylamino, C1—C16 alkoxy and C1—C16 haloalkyl; and
   n and m are each, independently, integers from 1 to 500.

4. The elastomeric polymer of claim 1, wherein the polyisobutylene macrodiol is hydroxyallyl telechelic polyisobutylene.

5. The elastomeric polymer of claim 1, wherein the polyisobutylene macrodiol is hydroxyalkyl telechelic polyisobutylene.

6. The elastomeric polymer of claim 5, wherein the polyisobutylene macrodiol is hydroxypropyl telechelic polyisobutylene.

7. The elastomeric polymer of claim 1, wherein the polyisobutylene diamine is aminoallyl telechelic polyisobutylene.

8. The elastomeric polymer of claim 1, wherein the number average molecular weight of the at least one polyisobutylene macrodiol is about 400 Da to about 6000 Da.

9. The elastomeric polymer of claim 1, wherein the number average molecular weight of the at least one polyisobutylene macrodiol is about 1000 Da to about 3000 Da.

10. The elastomeric polymer of claim 1, wherein the at least one polycarbonate macrodiol includes at least one poly(alkylene carbonate).

11. The elastomeric polymer of claim 1, wherein the hard segment comprises a diisocyanate residue and a chain extender.

12. The elastomeric polymer of claim 11 wherein the diisocyanate includes at least one member selected from the group consisting of 4,4'-methylenephenyl diisocyanate; methylene diisocyanate; p-phenylene diisocyanate; cis-cyclohexane-1,4-diisocyanate; trans-cyclohexane-1,4-diisocyanate; a mixture of cis cis-cyclohexane-1,4-diisocyanate and trans-cyclohexane-1,4-diisocyanate; 1,6-hexamethylene diisocyanate; 2,4-toluene diisocyanate; cis-2,4-toluene diisocyanate; trans-2,4-toluene diisocyanate; a mixture of cis-2,4-toluene diisocyanate and trans-2,4-toluene diisocyanate; p-tetramethylxylene diisocyanate; and m-tetramethylxylene diisocyanate.

13. The elastomeric polymer of claim 11, wherein the chain extender includes at least one member selected from the group consisting of 1,4-butanediol; 1,5 pentanediol; 1,6-hexanediol; 1,8-octanediol; 1,9-nonanediol; 1,10-decanediol, 1,12-dodacanediol; 1,4-cyclohexane dimethanol; p-xyleneglycol and 1,4-bis(2-hydroxyethoxy)benzene.

14. The elastomeric polymer of claim 11, wherein the chain extender includes at least one member selected from the group consisting of 1,4-diaminobutane; 1,5-diaminopentane; 1,6-diaminohexane; 1,8-diaminooctane; 1,9-diaminononane; 1,10-diamonodecane, 1,12-diaminododacane; 1,4-diaminocyclohexane; 2,5-diaminoxylene and isophoronediamine and water.

15. The elastomeric polymer of claim 11, wherein the diisocyanate is 4,4'-methylenephenyl diisocyanate and wherein the chain extender is 1,4-butanediol.

16. The elastomeric polymer of claim 1, wherein:
the polyisobutylene macrodiol of the soft segment comprises a hydroxylalkyl telechelic polyisobutylene residue, and
the hard segment comprises a 4,4'-methylenediphenyl diisocyanate and 1,4-butanediol chain extender.

17. The elastomeric polymer of claim 1, wherein: the polyisobutylene macrodiol of the soft segment comprises a hydroxylalkyl telechelic polyisobutylene residue, a poly (alkylene carbonate) residue, and a poly(tetramethylene oxide) diol residue; and the hard segment comprises a 4,4'-methylenediphenyl diisocyanate and 1,4-butanediol chain extender.

18. The elastomeric polymer of claim 1, wherein: the polyisobutylene macrodiol of the soft segment comprises a hydroxylalkyl telechelic polyisobutylene residue, a poly (alkylene carbonate) residue, and a poly(hexamethylene oxide) diol residue; the hard segment comprises a 4,4'-methylenediphenyl diisocyanate and 1,4-butanediol chain extender.

19. The elastomeric polymer of claim 1, wherein the polyisobutylene macrodiol of the soft segment comprises
(a) a hydroxyallyl difunctional polyisobutylene residue;
(b) a poly (alkylene carbonate) residue; and
(c) a poly(tetramethylene oxide) diol or poly(hexamethylene oxide) diol residue;
and
the hard segment comprises
(d) a 4,4'-methylenediphenyl diisocyanate; and
(e) 1,4-butanediol chain extender.

20. The polyurethane elastomeric polymer of claim 1, wherein the soft segment includes from about 10% to about 20% by weight of the soft segment of the at least one polycarbonate.

21. The elastomeric polymer of claim 1, wherein the soft segment includes from about 10% to about 20% by weight of the soft segment of the at least one polyether and the at least one polycarbonate.

22. The elastomeric polymer of claim 1, wherein the soft segment includes from about 10% to about 20% by weight of the soft segment of at least one polyether.

23. An article of manufacture, comprising: an elastomeric polymer, said elastomeric polymer, consisting of:
(1) a hard segment in the amount of 10% to 60% by weight of the elastomeric polymer, wherein the hard segment consists of:
a urethane, urea or urethane urea;
optionally at least one chain extender; and
optionally at least one diisocyanate residue; and
(2) a soft segment in the amount of 40% to 90% by weight of the elastomeric polymer, wherein the soft segment consists of:
(a) about 10% to about 30% by weight of the soft segment of a combination of at least one polyether macrodiol and at least one polycarbonate macrodiol;
(b) about 70% to about 90% by weight of the soft segment of at least one polyisobutylene macrodiol and/or diamine; and
(c),
wherein the number average molecular weight of the elastomeric polymer is not less than 40 kilodaltons, and wherein the article of manufacture is a medical device or an implant, and wherein the at least one polyether macrodiol is selected from the group consisting of poly(propylene oxide) diol, poly(trimethylene oxide) diol, poly(tetramethylene oxide) diol, poly(hexamethylene oxide) diol, poly(heptamethylene oxide) diol, poly(octamethylene oxide) diol and poly(decamethylene oxide) diol.

24. The article of claim 23, wherein the number average molecular weight of the elastomeric polymer is not less than 50 kilodaltons.

25. The article of claim 23, wherein the medical device or implant is a fiber, film, engineering plastic, fabric, coating, and adhesive joint.

26. The article of claim 23, wherein the medical device or implant is a cardiac pacemaker, a defibrillator, a catheter, an implantable prosthesis, a cardiac assist device, an artificial organ, a pacemaker lead, a defibrillator lead, a blood pump, a balloon pump, an a-V shunt, a biosensor, a membrane for cell encapsulation, a drug delivery device, a wound dressing, an artificial joint, an orthopedic implant or a soft tissue replacement.

27. A process for preparing an elastomeric polymer, comprising the steps of:
a) forming a mixture that includes at least one polyisobutylene macrodiol and/or diamine, at least one polyether macrodiol and a chain extender; and
b) reacting the mixture with a diisocyanate to yield an elastomeric polymer, wherein the elastomeric polymer consists of:
(i) a hard segment in the amount of 32% to 36% by weight of the elastomeric polymer, wherein the hard segment includes a urethane, urea or urethaneurea;
(ii) a soft segment in the amount of 64% to 68% by weight of the elastomeric polymer, wherein the soft segment consists of:

at least 2% by weight of the soft segment of at least one polyether macrodiol, and at least one polycarbonate macrodiol, and at least 2% by weight of the soft segment of the at least one polyisobutylene macrodiol and/or diamine, wherein the number average molecular weight of the elastomeric polymer is not less than 40 kilodaltons, and wherein the at least one polyether macrodiol is selected from the group consisting of poly(propylene oxide) diol, poly(trimethylene oxide) diol, poly(tetramethylene oxide) diol, poly(hexamethylene oxide) diol, poly(heptamethylene oxide) diol, poly(octamethylene oxide) diol and poly(decamethylene oxide) diol; and (iii) optionally a catalyst.

28. The article of claim 27, wherein the number average molecular weight of the elastomeric polymer is not less than 50 kilodaltons.

29. The process of claim 27, wherein the at least one polyisobutylene macrodiol or diamine of the soft segment is of the formula:

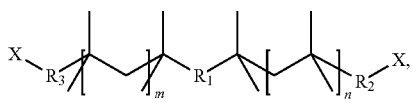

wherein:
each X is —OH, —NH$_2$ or —NHR$_4$;
R$_1$ is an initiator residue;
R$_2$ and R$_3$ and R$_4$ is each independently a C1—C16 alkyl, a C3—C16 cycloalkyl, a C2—C16 alkenyl, a C3—C16 cycloalkenyl, or a C2—C16 alkynyl, a C3—C16 cycloalkynyl, or a C6—C18 aryl, wherein, for each occurrence, R$_2$ or R$_3$ is, independently, optionally substituted with one or more groups selected from halo, cyano, nitro, dialkylamino, trialkylamino, C1—C16 alkoxy and C1—C16 haloalkyl; and
n and m are each independently integers from 1 to 500.

30. The process of claim 27 wherein mixture is formed at a temperature of about 45° C. to about 120° C.

31. The process of claim 27 wherein the mixture is formed in the presence of a catalyst.

32. The process of claim 31 wherein the catalyst is stannous octoate.

33. A process for preparing an elastomeric polymer, comprising the steps of:
a) reacting a diisocyanate with a mixture that includes at least one polyisobutylene macrodiol and/or diamine, at least one polycarbonate macrodiol, and at least one polyether macrodiol to form a prepolymer having terminally reactive diisocyanate groups; and
b) reacting the prepolymer with a chain extender to yield an elastomeric polymer, wherein the elastomeric polymer consists of:
(i) a hard segment in the amount of 32% to 36% by weight of the elastomeric polymer, wherein the hard segment includes a urethane, urea or urethaneurea; and
(ii) a soft segment in the amount of 64% to 68% by weight of the elastomeric polymer, wherein the soft segment consists of:

at least 2% by weight of the soft segment of the at least one polyether macrodiol, and the at least one polycarbonate macrodiol and at least 2% by weight of the soft segment of the at least one polyisobutylene macrodiol and/or diamine, wherein the number average molecular weight of the elastomeric polymer is not less than 40 kilodaltons, and wherein the at least one polyether macrodiol is selected from the group consisting of poly(propylene oxide) diol, poly(trimethylene oxide) diol, poly(tetramethylene oxide) diol, poly(hexamethylene oxide) diol, poly(heptamethylene oxide) diol, poly(octamethylene oxide) diol and poly(decamethylene oxide) diol.

34. The process of claim 33, wherein the number average molecular weight of the elastomeric polymer is not less than 50 kilodaltons.

35. The process of claim 33, wherein the at least one polyisobutylene macrodiol or diamine of the soft segment is of the formula:

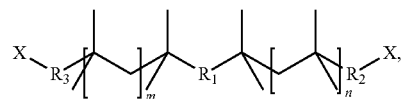

wherein:
each X is —OH, —NH$_2$ or —NHR$_4$;
R$_1$ is an initiator residue;
R$_2$ and R$_3$ and R$_4$ is each independently a C1—C16 alkyl, a C3—C16 cycloalkyl, a C2—C16 alkenyl, a C3—C16 cycloalkenyl, or a C2—C16 alkynyl, a C3—C16 cycloalkynyl, or a C6—C18 aryl, wherein, for each occurrence, R$_2$ or R$_3$ is, independently, optionally substituted with one or more groups selected from halo, cyano, nitro, dialkylamino, trialkylamino, C1—C16 alkoxy and C1—C16 haloalkyl; and
n and m are each independently integers from 1 to 500.

36. The process of claim 33 wherein the at least one polycarbonate macrodiol includes at least one poly(alkylene carbonate).

37. The process of claim 33 wherein the chain extender includes at least one member of the group consisting of 1,4-butanediol; 1,5-pentanediol; 1,6-hexanediol; 1,8-octanediol; 1,9-nonanediol; 1,10-decanediol, 1,12-dodecanediol; 1,4-cyclohexane dimethanol; p-xyleneglycol and 1,4-bis(2-hydroxyethoxy) benzene.

38. The process of claim 33 wherein the chain extender includes at least one member of the group consisting of 1,4-diaminobutane; 1,5-diaminopentane; 1,6-diaminohexane; 1,8-diaminooctane; 1,9-diaminononane; 1,10-diamonodecane, 1,12-diaminododacane; 1,4-diaminocyclohexane; 2,5-diaminoxylene and isophoronediamine and water.

39. A pacemaker lead comprising a polymer, the polymer consisting of:
(1) a hard segment in the amount of 32% to 36% by weight of the elastomeric polymer, wherein the hard segment includes a urethane, urea or urethane urea; and
(2) a soft segment in the amount of 64% to 68% by weight of the elastomeric polymer, wherein the soft segment consists of:
(a) from 10% to 30% by weight of the soft segment of a combination of at least one poly(tetramethylene oxide) diol and at least one polycarbonate macrodiol; and (b) from 70% to 90% by weight of the soft segment of at least one polyisobutylene macrodiol.

40. The pacemaker lead of claim 39 wherein the polymer has a Shore hardness of from 60A to 100A.

* * * * *